(12) United States Patent
Pullen

(10) Patent No.: US 7,935,794 B2
(45) Date of Patent: May 3, 2011

(54) MADCAM ANTIBODIES

(75) Inventor: Nicholas Pullen, Sandwich (GB)

(73) Assignee: Pfizer Ltd., Sandwich (GB)

( * ) Notice: Subject to any disclaimer, the term of this patent is extended or adjusted under 35 U.S.C. 154(b) by 0 days.

(21) Appl. No.: 12/429,154

(22) Filed: Apr. 23, 2009

(65) Prior Publication Data

US 2009/0214558 A1 Aug. 27, 2009

Related U.S. Application Data

(63) Continuation of application No. 11/484,456, filed on Jul. 10, 2006, now abandoned.

(60) Provisional application No. 60/697,453, filed on Jul. 8, 2005.

(51) Int. Cl.
*C07K 16/00* (2006.01)
*C12P 21/08* (2006.01)
*A61K 39/395* (2006.01)
*C12P 21/04* (2006.01)

(52) U.S. Cl. ............. 530/388.22; 530/387.1; 530/388.1; 530/388.15; 424/130.1; 424/141.1; 424/143.1; 435/69.6; 435/70.21

(58) Field of Classification Search ........................ None
See application file for complete search history.

(56) References Cited

U.S. PATENT DOCUMENTS

2004/0010810 A1 1/2004 Kucherlapati et al.

FOREIGN PATENT DOCUMENTS

| WO | WO 96/24673 | 8/1996 |
|---|---|---|
| WO | WO 99/58573 | 11/1999 |
| WO | WO 01/78779 | 10/2001 |
| WO | WO 2005/067620 | 7/2005 |

OTHER PUBLICATIONS

William E. Paul, Fundamental Immunology, 3rd Edition, 1993, pp. 292-295.*
Rudikoff et al. Proc. Natl. Acad. Sci. USA, 79(6):1979-1983, Mar. 1982.*
Colman P. M. Research in Immunology, 145:33-36, 1994.*
Bendig M. M. Methods: A Companion to Methods in Enzymology, 8:83-93, 1995.*
MacCallum et al. J. Mol. Biol., 262, 732-745, 1996.*
Casset et al. Biochemical and Biophysical Research Communications, 307:198-205, 2003.*
De Groot, A., et al., "De-immunization of Therapeutic Proteins by T-cell Epitope Modification," *Developments in Biologicals*, 2005, 171-194, vol. 122.
Leung, E., et al., "Bioassay Detects Soluble MAdCAM-1 in Body Fluids," *Immunology and Cell Biology*, 2004, 400-409, vol. 82, No. 4.
Tangri, S., et al., "Rationally Engineered Therapeutic Proteins with Reduced Immunogenicity," *The Journal of Immunology*, 2005, 3187-3196, vol. 174, No. 6.

* cited by examiner

*Primary Examiner* — David J. Blanchard

(57) ABSTRACT

The invention provides new, improved anti-MAdCAM antibodies. Uses of these antibodies in medicine are also included, in particular for the treatment of inflammatory conditions such as inflammatory bowel disease.

2 Claims, No Drawings

MADCAM ANTIBODIES

This application is a continuation of U.S. patent application Ser. No. 11/484,456, filed Jul. 10, 2006, abandoned, which claims priority, under 35 U.S.C. §119(e), from U.S. Provisional Application No. 60/697,453, filed Jul. 8, 2005.

FIELD OF THE INVENTION

The invention relates to an improved human antibody specific for Mucosal addressin cell adhesion molecule (MAdCAM).

BACKGROUND OF THE INVENTION

Mucosal addressin cell adhesion molecule (MAdCAM) is a member of the immunoglobulin superfamily of cell adhesion receptors. It is one of the adhesion molecules involved in the recruitment of lymphocytes to tissues when required, by means of interacting with an integrin molecule on the surface of the lymphocytes.

It has been shown that antibodies that inhibit binding of MAdCAM to its integrin binding partner, $\alpha_4\beta_7$, for example anti-MAdCAM antibodies (e.g. MECA-367; U.S. Pat. No. 5,403,919, U.S. Pat. No. 5,538,724) or anti-$\alpha_4\beta_7$ antibodies (e.g. Act-1; U.S. Pat. No. 6,551,593 or humanised Act-1, also called MLN02, described in WO 01/78779), can inhibit leukocyte extravasation into inflamed intestine, and can therefore be beneficial in the treatment of inflammatory bowel disease.

Anti-MAdCAM antibodies such as MECA-367, however, are not therapeutically useful in human patients; MECA-367 binds mouse MAdCAM, and does not show much affinity for the human MAdCAM molecule. In addition, being a rat antibody, it will lead to an immune response in human patients and therefore not be suitable for therapeutic use. Mouse monoclonal antibodies, directed against human MAdCAM have been described (WO 96/24673), but these are also likely to be immunogenic in humans. Recently, therapeutically useful, fully human anti-human MAdCAM antibodies with exquisite specificity and affinity to human and primate MAdCAM have been developed and disclosed in WO2005/067620.

It is known that even fully human antibodies can still lead to an immune response in some patients, which is likely to be due to sequences in the variable region of the antibody. The antibodies of the present invention are modifications of the human anti-MAdCAM antibodies disclosed in WO2005/067620, which are likely to be even less prone to any immunogenicity problems in human patients.

SUMMARY OF THE INVENTION

One aspect of the invention is a monoclonal antibody that specifically binds MAdCAM, comprising the variable region of the heavy chain of 6.22.2-mod_V (SEQ ID NO: 2).

Another aspect of the invention is a monoclonal antibody that specifically binds MAdCAM, comprising the variable region of the light chain of 6.34.2-mod_SSQ, 6.34.2-mod_QT, or 6.34.2-mod_SSQ,QT (SEQ ID NOs: 8, 10, 12).

Another aspect of the invention is a monoclonal antibody that specifically binds MAdCAM, comprising the variable region of the light chain of 6.67.1-mod_Y, 6.67.1-mod_TΔP, or 6.67.1-mod_Y,TΔP (SEQ ID NOs: 16, 18, 20).

Another aspect of the invention is a monoclonal antibody that specifically binds MAdCAM, comprising the variable region of the heavy chain of 6.77.1-mod_ΔS (SEQ ID NO: 22).

Another aspect of the invention is a monoclonal antibody that specifically binds MAdCAM, comprising the variable region of the light chain of 7.16.6_V, 7.16.6_S, or 7.16.6_VS (SEQ ID NOs: 30, 32, 34).

Another aspect of the invention is a monoclonal antibody that specifically binds MAdCAM, comprising the variable region of the heavy chain of 7.16.6_L (SEQ ID NO: 28).

Another aspect of the invention is a monoclonal antibody that specifically binds MAdCAM, comprising the variable region of the light chain of 7.16.6_V, 7.16.6_S, or 7.16.6_VS (SEQ ID NOs: 30, 32, 34) and the variable region of the heavy chain of 7.16.6_L (SEQ ID NO: 28).

Another aspect of the invention is a monoclonal antibody that specifically binds MAdCAM, comprising the variable region of the heavy chain of 9.8.2_ΔRGAYH,D (SEQ ID NO: 36).

Another aspect of the invention is a monoclonal antibody that specifically binds MAdCAM, comprising the variable region of the light chain of 9.8.2-mod (SEQ ID NO: 38).

Another aspect of the invention is a monoclonal antibody that specifically binds MAdCAM, wherein the antibody is selected from the group consisting of:
(a) an antibody comprising the variable regions encoded by the nucleic acid sequences set forth in SEQ ID NO: 1 and SEQ ID NO: 3;
(b) an antibody comprising the variable regions encoded by the nucleic acid sequences set forth in SEQ ID NO: 5 and SEQ ID NOs: 7, 9 or 11;
(c) an antibody comprising the variable regions encoded by the nucleic acid sequences set forth in SEQ ID NO: 13 and SEQ ID NOs: 15, 17, or 19;
(d) an antibody comprising the variable regions encoded by the nucleic acid sequences set forth in SEQ ID NO: 21 and SEQ ID NO: 23;
(e) an antibody comprising the variable regions encoded by the nucleic acid sequences set forth in SEQ ID NOs: 25 or 27 and SEQ ID NOs: 29, 31, or 33; or
(f) an antibody comprising the variable regions encoded by the nucleic acid sequences set forth in SEQ ID NO: 35 and SEQ ID NO: 37.

Another aspect of the invention is a monoclonal antibody that specifically binds MAdCAM, wherein the antibody is selected from the group consisting of:
(a) an antibody comprising the variable regions of the amino acid sequences set forth in SEQ ID NO: 2 and SEQ ID NO: 4, without the signal sequences;
(b) an antibody comprising the variable regions of the amino acid sequences set forth in SEQ ID NO: 6 and SEQ ID NOs: 8, 10, or 12, without the signal sequences;
(c) an antibody comprising the variable regions of the amino acid sequences set forth in SEQ ID NO: 14 and SEQ ID NOs: 16, 18, or 20, without the signal sequences;
(d) an antibody comprising the variable regions of the amino acid sequences set forth in SEQ ID NO: 22 and SEQ ID NO: 24, without the signal sequences;
(e) an antibody comprising the variable regions of the amino acid sequences set forth in SEQ ID NOs: 26 or 28 and SEQ ID NOs: 30, 32 or 34, without the signal sequences; or
(f) an antibody comprising the variable regions of the amino acid sequences set forth in SEQ ID NO: 36 and SEQ ID NO: 38, without the signal sequences.

Another aspect of the invention is a monoclonal antibody or antigen-binding portion thereof, wherein said antibody comprises:
(a) a heavy chain of amino acid sequence of SEQ ID NO: 2 and the light chain amino acid sequence of SEQ ID NO: 4, without the signal sequences.

(b) a heavy chain of amino acid sequence of SEQ ID NO: 6 and the light chain amino acid sequence of SEQ ID NOs: 8, 10, or 12, without the signal sequences.

(c) a heavy chain of amino acid sequence of SEQ ID NO: 14 and the light chain amino acid sequence of SEQ ID NOs: 16, 18, or 20, without the signal sequences.

(d) a heavy chain of amino acid sequence of SEQ ID NO: 22 and the light chain amino acid sequence of SEQ ID NO: 24, without the signal sequences.

(e) a heavy chain of amino acid sequence of SEQ ID NOs: 26 or 28 and the light chain amino acid sequence of SEQ ID NOs: 30, 32 or 34, without the signal sequences.

(f) a heavy chain of amino acid sequence of SEQ ID NO: 36 and the light chain amino acid sequence of SEQ ID NO: 38, without the signal sequences.

Another aspect of the invention is a human monoclonal antibody of the invention, wherein the heavy chain C-terminal lysine is cleaved.

Another aspect of the invention is a human monoclonal antibody of the invention, which is an $IgG_2$ isotype. A further aspect of the invention is a human monoclonal antibody of the invention, which is an $IgG_4$ isotype. A further aspect of the invention is a human monoclonal antibody of the invention which comprises a κ light chain. A further aspect of the invention is a human monoclonal antibody of the invention which comprises a λ light chain. A preferred aspect of the invention is a human monoclonal antibody of the invention which is an $IgG_2$ isotype with a κ light chain.

Another aspect of the invention is a vector comprising any of the sequences of the variable regions of SEQ ID NOs: 1, 7, 9, 11, 15, 17, 19, 21, 27, 29, 31, 33, 35, or 37 or any of the sequences encoding the variable regions of SEQ ID NOs: 2, 8, 10, 12, 16, 18, 20, 22, 28, 30, 32, 34, 36 or 38. A further aspect of the invention is a host cell comprising any of the sequences of the variable regions of SEQ ID NOs: 1, 7, 9, 11, 15, 17, 19, 21, 27, 29, 31, 33, 35 or 37, or any of the sequences encoding the variable regions of SEQ ID NOs: 2, 8, 10, 12, 16, 18, 20, 22, 28, 30, 32, 34, 36 or 38. The host cell can be a bacterium such as *E. coli*, a yeast such as *Saccharomyces cerevisiae* or *Pichia pistoris*, a plant cell, an insect cell, or a mammalian cell. More preferably, the host cell is a mammalian cell. Most preferably, the host cell is a CHO cell or NS0 cell.

Another aspect of the invention is a method of producing the antibody of the invention, comprising culturing a host cell comprising any of the sequences of the variable regions of SEQ ID NOs: 1, 7, 9, 11, 15, 17, 19, 21, 27, 29, 31, 33, 35 or 37, or any of the sequences encoding the variable regions of SEQ ID NOs: 2, 8, 10, 12, 16, 18, 20, 22, 28, 30, 32, 34, 36 or 38, under conditions in which the antibody is expressed, and recovering the antibody from the host cell or its culture supernatant.

Another aspect of the invention is a transgenic animal or a transgenic plant, comprising any of the sequences of the variable regions of SEQ ID NOs: 1, 7, 9, 11, 15, 17, 19, 21, 27, 29, 31, 33, 35 or 37, or any of the sequences encoding the variable regions of SEQ ID NOs: 2, 8, 10, 12, 16, 18, 20, 22, 28, 30, 32, 34, 36 or 38.

One aspect of the invention is the use of the antibodies of the invention or an antigen-binding portion thereof for use as a medicament. Another aspect of the invention is the use of the antibodies of the invention or an antigen-binding portion thereof for the manufacture of a medicament for the treatment of conditions involving MAdCAM-mediated adhesion of leukocytes. Another aspect of the invention is the use of the antibodies of the invention or an antigen-binding portion thereof for the treatment of inflammatory conditions, such as but not limited to inflammatory diseases of the gastrointestinal tract including inflammatory bowel disease such as Crohn's disease, ulcerative colitis; diverticula disease, gastritis, liver disease, primary sclerosis, sclerosing cholangitis. Inflammatory diseases also include but are not limited to abdominal disease (including peritonitis, appendicitis, biliary tract disease), acute transverse myelitis, allergic dermatitis (including allergic skin, allergic eczema, skin atopy, atopic eczema, atopic dermatitis, cutaneous inflammation, inflammatory eczema, inflammatory dermatitis, flea skin, miliary dermatitis, miliary eczema, house dust mite skin), ankylosing spondylitis (Reiters syndrome), asthma, airway inflammation, atherosclerosis, arteriosclerosis, biliary atresia, bladder inflammation, breast cancer, cardiovascular inflammation (including vasculitis, rheumatoid nail-fold infarcts, leg ulcers, polymyositis, chronic vascular inflammation, pericarditis, chronic obstructive pulmonary disease), pancreatitis, including chronic pancreatitis, perineural inflammation, coeliac disease, colitis (including amoebic colitis, infective colitis, bacterial colitis, Crohn's colitis, ischemic colitis, ulcerative colitis, idiopathic proctocolitis, inflammatory bowel disease, pseudomembranous colitis), chloroma, collagen vascular disorders (rheumatoid arthritis, SLE, progressive systemic sclerosis, mixed connective tissue disease, diabetes mellitus), Crohn's disease (regional enteritis, granulomatous ileitis, ileocolitis, digestive system inflammation), demyelinating disease (including myelitis, multiple sclerosis, disseminated sclerosis, acute disseminated encephalomyelitis, perivenous demyelination, vitamin B12 deficiency, Guillain-Barre syndrome, MS-associated retrovirus), dermatomyositis, diverticulitis, emphysema, exudative diarrhea, fever in immunocompromised patients, gastritis, granulomatous hepatitis, granulomatous inflammation, cholecystitis, insulin-dependent diabetes mellitus, liver inflammatory diseases (liver fibrosis including but not limited to Hepatitis C-induced liver damage, alcoholic liver disease, non-alcoholic steatohepatitis (NASH); primary biliary cirrhosis, hepatitis, sclerosing cholangitis), lung inflammation (idiopathic pulmonary fibrosis, eosinophilic granuloma of the lung, pulmonary histiocytosis X, peribronchiolar inflammation, acute bronchitis), lymphogranuloma venereum, malignant melanoma, mouth/tooth disease (including gingivitis, periodontal disease), metastatic cancers, mucositis, musculoskeletal system inflammation (myositis), nonalcoholic steatohepatitis (nonalcoholic fatty liver disease), ocular & orbital inflammation (including uveitis, optic neuritis, peripheral rheumatoid ulceration, peripheral corneal inflammation), osteoarthritis, osteomyelitis, pharyngeal inflammation, polyarthritis, proctitis, psoriasis, radiation injury, sarcoidosis, sickle cell necropathy, superficial thrombophlebitis, systemic inflammatory response syndrome, thyroiditis, systemic lupus erythematosus, tropical sprue, graft versus host disease, acute burn injury, Behçet's syndrome, Sjögren's syndrome, uterine disorders such as endometriosis, dysmenorrhea or pelvic inflammatory disease. Preferably, the antibodies of the invention are used for the treatment of inflammatory bowel disease such as Crohn's disease and ulcerative colitis, graft versus host disease, liver fibrosis, uveitis. Even more preferably, the antibodies of the invention are used for the treatment is of inflammatory bowel disease.

Another aspect of the invention is a method of treatment of a condition mentioned above, comprising administering to a patient in need of such treatment a therapeutically effective amount of an antibody of the invention.

Another aspect of the invention is a pharmaceutical composition comprising an antibody of the invention or an antigen-binding portion thereof and a pharmaceutically acceptable carrier or excipient.

DETAILED DESCRIPTION OF THE INVENTION

A nucleic acid molecule encoding the entire heavy chain of an anti-MAdCAM antibody of the invention may be constructed by fusing a nucleic acid molecule encoding the entire variable domain of a heavy chain or an antigen-binding domain thereof with a constant domain of a heavy chain. Similarly, a nucleic acid molecule encoding the light chain of an anti-MAdCAM antibody may be constructed by fusing a nucleic acid molecule encoding the variable domain of a light chain or an antigen-binding domain thereof with a constant domain of a light chain. Nucleic acid molecules encoding the VH and VL regions may be converted to full-length antibody genes by inserting them into expression vectors already encoding heavy chain constant and light chain constant regions, respectively, such that the VH segment is operatively linked to the heavy chain constant region (CH) segment(s) within the vector and the VL segment is operatively linked to the light chain constant region (CL) segment within the vector. Alternatively, the nucleic acid molecules encoding the VH or VL chains are converted into full-length antibody genes by linking, e.g., ligating, the nucleic acid molecule encoding a VH chain to a nucleic acid molecule encoding a CH chain using standard molecular biological techniques. The same may be achieved using nucleic acid molecules encoding VL and CL chains. The sequences of human heavy and light chain constant region genes are known in the art. See, e.g., Kabat et al., *Sequences of Proteins of Immunological Interest*, 5th Ed., NIH Publ. No. 91-3242 (1991). Nucleic acid molecules encoding the full-length heavy and/or light chains may then be expressed from a cell into which they have been introduced and the anti-MAdCAM antibody isolated.

A nucleic acid molecule encoding either the heavy chain of an anti-MAdCAM antibody of the invention or an antigen-binding portion thereof, or the light chain of an anti-MAdCAM antibody of the invention or an antigen-binding portion thereof may be prepared, for example, by synthesizing appropriate nucleic acids using the sequence information provided herein, and splicing them together with the desired constant regions of immunoglobulin genes. The skilled person will be well aware of the appropriate methods.

The nucleic acid molecules may be used to recombinantly express large quantities of anti-MAdCAM antibodies, as described below. The nucleic acid molecules may also be used to produce chimeric antibodies, single chain antibodies, immunoadhesins, diabodies, mutated antibodies and antibody derivatives, as described further below. If the nucleic acid molecules are derived from a non-human, non-transgenic animal, the nucleic acid molecules may be used for antibody humanization, also as described below.

The invention provides vectors comprising the nucleic acid molecules of the invention that encode the heavy chain or the antigen-binding portion thereof. The invention also provides vectors comprising the nucleic acid molecules of the invention that encode the light chain or antigen-binding portion thereof. The invention also provides vectors comprising nucleic acid molecules encoding fusion proteins, modified antibodies, antibody fragments, and probes thereof.

To express the antibodies, or antibody portions used in the invention, DNAs encoding partial or full-length light and heavy chains, obtained as described above, are inserted into expression vectors such that the genes are operatively linked to transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245, and 4,968,615, each of which is hereby incorporated by reference. Methods for expressing antibodies in plants, including a description of promoters and vectors, as well as transformation of plants are known in the art. See, e.g., U.S. Pat. No. 6,517,529. Methods of expressing polypeptides in bacterial cells or fungal cells, e.g., yeast cells, are also well known in the art.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection), and the glutamate synthetase gene.

Nucleic acid molecules encoding the heavy chain or an antigen-binding portion thereof and/or the light chain or an antigen-binding portion thereof of an anti-MAdCAM antibody, and vectors comprising these nucleic acid molecules, can be used for transformation of a suitable mammalian plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, e.g., U.S. Pat. Nos. 4,399,216, 4,912,040, 4,740,461, and 4,959,455 (which patents are hereby incorporated herein by reference). Methods of transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include many immortalized cell lines available from the American Type Culture Collection (ATCC). These include, inter alia, Chinese hamster ovary (CHO) cells, NS0, SP2 cells, HEK-293T cells, NIH-3T3 cells, HeLa cells, baby hamster kidney (BHK) cells, monkey kidney cells (COS), human hepatocellular carcinoma cells (e.g., Hep G2), A549 cells, 3T3 cells, and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion thereof, the light chain and/or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Plant host cells include, e.g., *Nicotiana, Arabidopsis*, duckweed, corn, wheat, potato, etc. Bacterial host cells include *E. coli* and *Streptomyces* species. Yeast host cells include *Schizosaccharomyces pombe, Saccharomyces cerevisiae* and *Pichia pastoris*.

Further, expression of antibodies used in the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 338 841 and 0 323 997.

It is likely that antibodies expressed by different cell lines or in transgenic animals will have different glycosylation from each other. However, all antibodies encoded by the nucleic acid molecules provided herein, or comprising the amino acid sequences provided herein are part of the instant invention, regardless of the glycosylation of the antibodies.

Transgenic non-human animals and transgenic plants comprising one or more nucleic acid molecules described above may be used to produce antibodies used in the invention. Antibodies can be produced in and recovered from tissue or bodily fluids, such as milk, blood or urine, of goats, cows, horses, pigs, rats, mice, rabbits, hamsters or other mammals. See, e.g., U.S. Pat. Nos. 5,827,690, 5,756,687, 5,750,172, and 5,741,957. As described above, non-human transgenic animals that comprise human immunoglobulin loci can be immunized with MAdCAM or a portion thereof. Methods for making antibodies in plants are described, e.g., in U.S. Pat. Nos. 6,046,037 and 5,959,177, incorporated herein by reference.

Non-human transgenic animals and transgenic plants are produced by introducing one or more nucleic acid molecules used in the invention into the animal or plant by standard transgenic techniques. See Hogan, supra. The transgenic cells used for making the transgenic animal can be embryonic stem cells, somatic cells or fertilized egg cells. The transgenic non-human organisms can be chimeric, nonchimeric heterozygotes, and nonchimeric homozygotes. See, e.g., Hogan et al., *Manipulating the Mouse Embryo: A Laboratory Manual* 2ed., Cold Spring Harbor Press (1999); Jackson et al., *Mouse Genetics and Transgenics: A Practical Approach*, Oxford University Press (2000); and Pinkert, *Transgenic Animal Technology: A Laboratory Handbook*, Academic Press (1999). The transgenic non-human organisms may have a targeted disruption and replacement that encodes a heavy chain and/or a light chain of interest. The transgenic animals or plants may comprise and express nucleic acid molecules encoding heavy and light chains that combine to bind specifically to MAdCAM, preferably human MAdCAM. The transgenic animals or plants may comprise nucleic acid molecules encoding a modified antibody such as a single-chain antibody, a chimeric antibody or a humanized antibody. The anti-MAdCAM antibodies may be made in any transgenic animal. The non-human animals include mice, rats, sheep, pigs, goats, cattle or horses. The non-human transgenic animal expresses said encoded polypeptides in blood, milk, urine, saliva, tears, mucus and other bodily fluids.

Treatment may involve administration of one or more inhibitory anti-MAdCAM monoclonal antibodies of the invention, or antigen-binding fragments thereof, alone or with a pharmaceutically acceptable carrier. Inhibitory anti-MAdCAM antibodies and compositions comprising them, can be administered in combination with one or more other therapeutic, diagnostic or prophylactic agents. Such additional agents may be included in the same composition or administered separately. Additional therapeutic agents include anti-inflammatory or immunomodulatory agents. These agents include, but are not limited to, the topical and oral corticosteroids such as prednisolone, methylprednisolone, NCX-1015 or budesonide; the aminosalicylates such as mesalazine, olsalazine, balsalazide or NCX-456; the class of immunomodulators such as azathioprine, 6-mercaptopurine, methotrexate, cyclosporin, FK506, IL-10 (Ilodecakin), IL-11 (Oprelevkin), IL-12, MIF/CD74 antagonists, CD40 antagonists, such as TNX-100/5-D12, OX40L antagonists, GM-CSF, pimecrolimus or rapamycin; the class of anti-TNFα agents such as infliximab, adalimumab, CDP-870, onercept, etanercept; the class of anti-inflammatory agents, such as PDE-4 inhibitors (roflumilast, etc), TACE inhibitors (DPC-333, RDP-58, etc) and ICE inhibitors (VX-740, etc) as well as IL-2 receptor antagonists, such as daclizumab, the class of selective adhesion molecule antagonists, such as natalizumab, MLN-02, or alicaforsen, classes of analgesic agents such as, but not limited to, COX-2 inhibitors, such as rofecoxib, valdecoxib, celecoxib, P/Q-type voltage sensitive channel (α2δ) modulators, such as gabapentin and pregabalin, NK-1 receptor antagonists, cannabinoid receptor modulators, and delta opioid receptor agonists, as well as anti-neoplastic, anti-tumor, anti-angiogenic chemotherapeutic agents, or anti-fibrotic agent including but not limited to protease inhibitors, preferably caspase inhibitors, more preferably the caspase inhibitor is a compound of formula I.

The compound of formula I

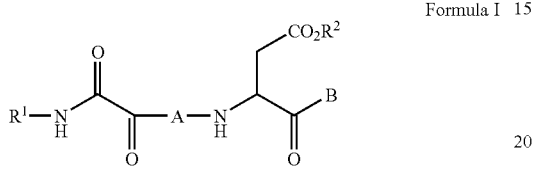

Formula I wherein A, B, R1 and R2 are as defined below.
wherein
A is a natural or unnatural amino acid of Formula IIa-i:

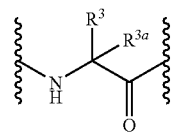

IIa

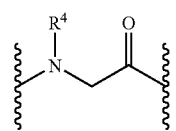

IIb

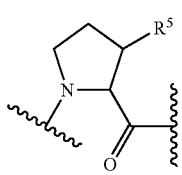

IIc

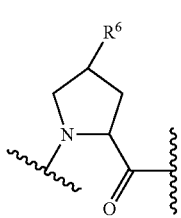

IId

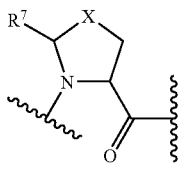

IIe

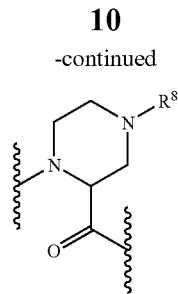

IIf

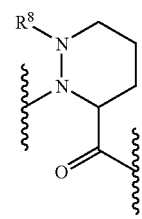

IIg

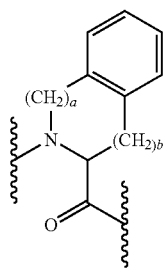

IIh

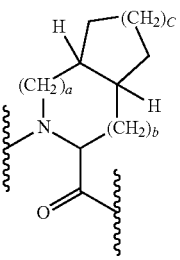

IIi

B is a hydrogen atom, a deuterium atom, alkyl, cycloalkyl, phenyl, substituted phenyl, naphthyl, substituted naphthyl, 2-benzoxazolyl, substituted 2-oxazolyl, $(CH_2)_n$-cycloalkyl, $(CH_2)_n$-phenyl, $(CH_2)_n$-(substituted phenyl), $(CH_2)_n$-(1 or 2-naphthyl), $(CH_2)_n$-(substituted 1 or 2-naphthyl), $(CH_2)_n$-(heteroaryl), $(CH_2)_n$-(substituted heteroaryl), halomethyl, $CO_2R^{12}$, $CONR^{13}R^{14}$, $CH_2ZR^{15}$, $CH_2OCO(aryl)$, $CH_2OCO(heteroaryl)$, or $CH_2OPO(R^{16})R^{17}$, where Z is an oxygen or a sulfur atom, or B is a group of the Formula IIIa-c:

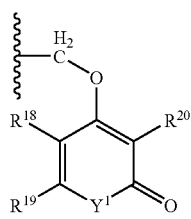

IIIa

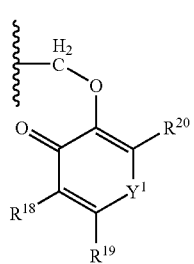

IIIb

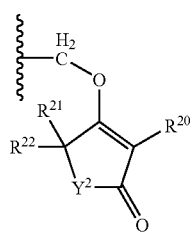

IIIc $R^1$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, substituted (heteroaryl)alkyl, $R^{1a}(R^{1b})$N, or $R^{1c}O$; and $R^2$ is hydrogen, lower alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, or substituted (1 or 2 naphthyl)alkyl;

And wherein:

$R^{1a}$ and $R^{1b}$ are independently hydrogen, alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, or substituted (heteroaryl)alkyl, with the proviso that $R^{1a}$ and $R^{1b}$ cannot both be hydrogen;

$R^{1c}$ is alkyl, cycloalkyl, (cycloalkyl)alkyl, phenyl, substituted phenyl, phenylalkyl, substituted phenylalkyl, naphthyl, substituted naphthyl, (1 or 2 naphthyl)alkyl, substituted (1 or 2 naphthyl)alkyl, heteroaryl, substituted heteroaryl, (heteroaryl)alkyl, or substituted (heteroaryl)alkyl;

$R^3$ is $C_{1-6}$ alkyl, cycloalkyl, phenyl, substituted phenyl, $(CH_2)_nNH_2$, $(CH_2)NHCOR^9$, $(CH_2)_nN(C=NH)NH_2$, $(CH_2)_mCO_2R^2$, $(CH_2)_mOR^{10}$, $(CH_2)_mSR^{11}$, $(CH_2)_n$cycloalkyl, $(CH_2)_n$phenyl, $(CH_2)_n$(substituted phenyl), $(CH_2)_n$(1 or 2-naphthyl) or $(CH_2)_n$(heteroaryl), wherein heteroaryl includes pyridyl, thienyl, furyl, thiazolyl, imidazolyl, pyrazolyl, isoxazolyl, pyrazinyl, pyrimidyl, triazinyl, tetrazolyl, and indolyl;

$R^{3a}$ is hydrogen or methyl, or $R^3$ and $R^{3a}$ taken together are —$(CH_2)_d$— where d is an integer from 2 to 6;

$R^4$ is phenyl, substituted phenyl, $(CH_2)_m$phenyl, $(CH_2)_m$(substituted phenyl), cycloalkyl, or benzofused cycloalkyl;

$R^5$ is hydrogen, lower alkyl, cycloalkyl, phenyl, substituted phenyl, $(CH_2)_n$cycloalkyl, $(CH_2)_n$phenyl, $(CH_2)_n$(substituted phenyl), or $(CH_2)_n$(1 or 2-naphthyl);

$R^6$ is hydrogen, fluorine, oxo, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{10}$, $SR^{11}$, or $NHCOR^9$;

$R^7$ is hydrogen, oxo (i.e. =O), lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^8$ is lower alkyl, cycloalkyl, $(CH_2)_n$cycloalkyl, $(CH_2)_n$phenyl, $(CH_2)_n$(substituted phenyl), $(CH_2)_n$(1 or 2-naphthyl), or $COR^9$;

$R^9$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), $(CH_2)_n$(1 or 2-naphthyl), $OR^{12}$, or $NR^{13}R^{14}$;

$R^{10}$ is hydrogen, lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^{11}$ is lower alkyl, cycloalkyl, phenyl, substituted phenyl, naphthyl, $(CH_2)_n$cycloalkyl, $(CH_2)_n$phenyl, $(CH_2)_n$(substituted phenyl), or $(CH_2)_n$(1 or 2-naphthyl);

$R^{12}$ is lower alkyl, cycloalkyl, $(CH_2)_n$cycloalkyl, $(CH_2)_n$phenyl, $(CH_2)_n$(substituted phenyl), or $(CH_2)_n$(1 or 2-naphthyl);

$R^{13}$ is hydrogen, lower alkyl, cycloalkyl, phenyl, substituted phenyl, naphthyl, substituted naphthyl, $(CH_2)_n$cycloalkyl, $(CH_2)_n$phenyl, $(CH_2)_n$(substituted phenyl), or $(CH_2)_n$(1 or 2-naphthyl);

$R^{14}$ is hydrogen or lower alkyl; or $R^{13}$ and $R^{14}$ taken together form a five to seven membered carbocyclic or heterocyclic ring, such as morpholine, or N-substituted piperazine;

$R^{15}$ is phenyl, substituted phenyl, naphthyl, substituted naphthyl, heteroaryl, $(CH_2)_n$phenyl, $(CH_2)_n$(substituted phenyl), $(CH_2)_n$(1 or 2-naphthyl), or $(CH_2)_n$(heteroaryl);

$R^{16}$ or $R^{17}$ are independently lower alkyl, cycloalkyl, phenyl, substituted phenyl, naphthyl, phenylalkyl, substituted phenylalkyl, or (cycloalkyl)alkyl;

$R^{18}$ and $R^{19}$ are independently hydrogen, alkyl, phenyl, substituted phenyl, $(CH_2)_n$phenyl, $(CH_2)_n$(substituted phenyl), or $R^{18}$ and $R^{19}$ taken together are —(CH=CH)$_2$;

$R^{20}$ is hydrogen, alkyl, phenyl, substituted phenyl, $(CH_2)_n$phenyl, $(CH_2)_n$(substituted phenyl);

$R^{21}$, $R^{22}$ and $R^{23}$ are independently hydrogen, or alkyl;

X is $CH_2$, $(CH_2)_2$, $(CH_2)_3$, or S;

$Y^1$ is O or $NR^{23}$;

$Y^2$ is $CH_2$, O, or $NR^{23}$;

a is 0 or 1 and b is 1 or 2, provided that when a is 1 then b is 1;

c is 1 or 2, provided that when c is 1 then a is 0 and b is 1;

m is 1 or 2; and n is 1, 2, 3, or 4;

or a pharmaceutically acceptable salt thereof.

As used herein, the term "alkyl" means a straight or branched $C_1$ to $C_{10}$ carbon chain, such as methyl, ethyl, tert-butyl, iso-propyl, n-octyl, and the like. The term "lower alkyl" means a straight chain or branched $C_1$ to $C_6$ carbon chain, such as methyl, ethyl, iso-propyl, and the like.

Depending on the choice of solvent and other conditions known to the skilled person, these compounds may also take the ketal or acetal form, and the use of these forms in the combination of the invention is included in the invention.

These compounds can be prepared as described in WO 00/01666 or in U.S. Pat. No. 6,544,951, hereby incorporated by reference in their entirety. Preferred subgroups are those listed in U.S. Pat. No. 6,544,951.

Preferred are compounds selected from:

(3S)-3-[N—(N'-(2-Fluoro-4-Iodophenyl)Oxamyl)Valinyl] Amino-5-(2',3',5',6'-Tetrafluorophenoxy)-4-Oxopentanoic acid;

(3S)-3-[N—(N'-(2-Chlorophenyl)Oxamyl)Valinyl]Amino-5-(2',3',5',6'-Tetrafluorophenoxy)-4-Oxopentanoic acid;

(3S)-3-[N—(N'-(2-Bromophenyl)Oxamyl)Valinyl]Amino-5-(2',3',5',6'-Tetrafluorophenoxy)-4-Oxopentanoic acid;

(3S)-3-[N—(N'-(2-Fluorophenyl)Oxamyl)Valinyl]Amino-5-(2',3',5',6'-Tetrafluorophenoxy)-4-Oxopentanoic acid;
(3S)-3-[N—(N'-(2-Trifluoromethylphenyl)Oxamyl)Valinyl]Amino-5-(2',3',5',6'-Tetrafluorophenoxy)-4-Oxopentanoic acid;
(3S)-3-[N—(N'-(1-Anthryl)Oxamyl)Valinyl]Amino-5-(2',3',5',6'-Tetrafluorophenoxy)-4-Oxopentanoic acid;
(3S)-3-[N—(N'-(2-Tert-Butylphenyl)Oxamyl)Alaninyl]Amino-5-(2',3',5',6'-Tetrafluorophenoxy)-4-Oxopentanoic acid;
(3S)-3-[N—(N'-(2-Trifluoromethylphenyl)Oxamyl)Alaninyl]Amino-5-(2',3',5',6'-Tetrafluorophenoxy)-4-Oxopentanoic acid;
(3S)-3-[N—(N'-(2,6-Difluorophenyl)Oxamyl)Alaninyl]Amino-5-(2',3',5',6'-Tetrafluorophenoxy)-4-Oxopentanoic acid;
(3S)-3-[N—(N'-(1-Naphthyl)Oxamyl)Alaninyl]Amino-5-(2',3',5',6'-Tetrafluorophenoxy)-4-Oxopentanoic acid;
(3S)-3-[N—(N'-(4-Methoxyphenyl)Oxamyl)Alaninyl]Amino-5-(2',3',5',6'-Tetrafluorophenoxy)-4-Oxopentanoic acid;
(3S)-3-[N—(N'-(2-Trifluoromethylphenyl)Oxamyl)Valinyl]Amino-4-Oxobutanoic acid;
(3S)-3-[N—(N'-(2-tert-Butylmethylphenyl)Oxamyl)Valinyl]Amino-4-Oxobutanoic acid;
(3S)-3-[N—(N'-(2-Benzylphenyl)Oxamyl)Valinyl]Amino-4-Oxobutanoic acid;
(3S)-3-[N—(N'-(2-Phenylphenyl)Oxamyl)Valinyl]Amino-4-Oxobutanoic acid.

Most preferably, the compound is (3S)-3-[N—(N'-(2-Tert-Butylphenyl)Oxamyl)Alaninyl]Amino-5-(2',3',5',6'-Tetrafluorophenoxy)-4-Oxopentanoic acid.

As used herein, "pharmaceutically acceptable carrier" means any and all solvents, dispersion media, coatings, antibacterial and antifungal agents, isotonic and absorption enhancing or delaying agents, and the like that are physiologically compatible. Some examples of pharmaceutically acceptable carriers are water, saline, phosphate buffered saline, acetate buffer with sodium chloride, dextrose, glycerol, Polyethylene glycol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are surfactants, wetting agents or minor amounts of auxiliary substances such as wetting or emulsifying agents, preservatives or buffers, which enhance the shelf life or effectiveness of the antibody.

The compositions used in this invention may be in a variety of forms, for example, liquid, semi-solid and solid dosage forms, such as liquid solutions (e.g., injectable and infusible solutions), dispersions or suspensions, tablets, pills, lyophilized cake, dry powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular, intradermal). In a preferred embodiment, the antibody is administered by intravenous infusion or injection. In another preferred embodiment, the antibody is administered by intramuscular, intradermal or subcutaneous injection. If desired, the antibody may be administered by using a pump, enema, suppository, or indwelling reservoir or such like.

Therapeutic compositions typically must be sterile and stable under the conditions of manufacture and storage. The composition can be formulated as a solution, lyophilized cake, dry powder, microemulsion, dispersion, liposome, or other ordered structure suitable to high drug concentration. Sterile injectable solutions can be prepared by incorporating the anti-MAdCAM antibody in the required amount in an appropriate solvent with one or a combination of ingredients enumerated above, as required, followed by sterilization. In the case of sterile powders for the preparation of sterile injectable solutions, the preferred methods of preparation are vacuum drying and freeze-drying that yields a powder of the active ingredient plus any additional desired ingredient from a previously sterile solution thereof. Generally, dispersions are prepared by incorporating the active compound into a sterile vehicle that contains a basic dispersion medium and the required other ingredients from those enumerated above. The desired characteristics of a solution can be maintained, for example, by the use of surfactants and the required particle size in the case of dispersion by the use of surfactants, phospholipids and polymers. Prolonged absorption of injectable compositions can be brought about by including in the composition an agent that delays absorption, for example, monostearate salts, polymeric materials, oils and gelatin.

The antibodies of the present invention can be administered by a variety of methods known in the art, although for many therapeutic applications, the preferred route/mode of administration is subcutaneous, intramuscular, intradermal or intravenous infusion. As will be appreciated by the skilled artisan, the route and/or mode of administration will vary depending upon the desired results.

In certain embodiments, the antibody compositions may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York (1978)).

In certain embodiments, an anti-MAdCAM antibody of the invention can be orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the anti-MAdCAM antibodies can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The compositions of the invention may include a "therapeutically effective amount" or a "prophylactically effective amount" of an antibody or antigen-binding portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a pre-determined quantity of active compound calculated to produce the desired therapeutic effect in association with the required pharmaceutical carrier. The specification for the dosage unit forms of the invention are dictated by and directly dependent on (a) the unique characteristics of the anti-MAdCAM antibody or portion thereof and the particular therapeutic or prophylactic effect to be achieved, and (b) the limitations inherent in the art of compounding such an antibody for the treatment of sensitivity in individuals.

An exemplary, non-limiting range for a therapeutically or prophylactically effective amount of an antibody or antibody portion of the invention is 0.025 to 50 mg/kg, more preferably 0.1 to 50 mg/kg, more preferably 0.1-25, 0.1 to 10 or 0.1 to 3 mg/kg. In some embodiments, a formulation contains 5 mg/mL of antibody in a buffer of 20 mM sodium acetate, pH 5.5, 140 mM NaCl, and 0.2 mg/mL polysorbate 80. In other embodiments, a formulation contains 10 mg/ml of antibody in 2.73 mg/ml of sodium acetate trihydrate, 45 mg/ml of mannitol, 0.02 mg/ml of disodium EDTA dihydrate, 0.2 mg/ml of polysorbate 80, adjusted to pH 5.5 with glacial acetic acid, e.g. for intravenous use. In other embodiments, a formulation contains 50 mg/ml of antibody, 2.73 mg/ml of sodium acetate trihydrate, 45 mg/ml of mannitol, 0.02 mg/ml of disodium EDTA dihydrate, 0.4 mg/ml of polysorbate 80, adjusted to pH 5.5 with glacial acetic acid, e.g. for subcutaneous or intradermal use. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In a preferred embodiment, the antibody is administered in a formulation as a sterile aqueous solution having a pH that ranges from about 5.0 to about 6.5 and comprising from about 1 mg/ml to about 200 mg/ml of antibody, from about 1 millimolar to about 100 millimolar of histidine buffer, from about 0.01 mg/ml to about 10 mg/ml of polysorbate 80, from about 100 millimolar to about 400 millimolar of trehalose, and from about 0.01 millimolar to about 1.0 millimolar of disodium EDTA dihydrate.

Another aspect of the present invention provides kits comprising an anti-MAdCAM antibody or antibody portion of the invention or a composition comprising such an antibody. A kit may include, in addition to the antibody or composition, diagnostic or therapeutic agents. A kit can also include instructions for use in a diagnostic or therapeutic method. In a preferred embodiment, the kit includes the antibody or a composition comprising it and a diagnostic agent that can be used in a method described below. In another preferred embodiment, the kit includes the antibody or a composition comprising it and one or more therapeutic agents that can be used in a method described below.

The nucleic acid molecules of the instant invention can be administered to a patient in need thereof via gene therapy. The therapy may be either in vivo or ex vivo. In a preferred embodiment, nucleic acid molecules encoding both a heavy chain and a light chain are administered to a patient. In a more preferred embodiment, the nucleic acid molecules are administered such that they are stably integrated into chromosomes of B cells because these cells are specialized for producing antibodies. In a preferred embodiment, precursor B cells are transfected or infected ex vivo and re-transplanted into a patient in need thereof. In another embodiment, precursor B cells or other cells are infected in vivo using a recombinant virus known to infect the cell type of interest. Typical vectors used for gene therapy include liposomes, plasmids and viral vectors. Exemplary viral vectors are retroviruses, adenoviruses and adeno-associated viruses. After infection either in vivo or ex vivo, levels of antibody expression can be monitored by taking a sample from the treated patient and using any immunoassay known in the art or discussed herein.

In a preferred embodiment, the gene therapy method comprises the steps of administering an isolated nucleic acid molecule encoding the heavy chain or an antigen-binding portion thereof of an anti-MAdCAM antibody and expressing the nucleic acid molecule. In another embodiment, the gene therapy method comprises the steps of administering an isolated nucleic acid molecule encoding the light chain or an antigen-binding portion thereof of an anti-MAdCAM antibody and expressing the nucleic acid molecule. In a more preferred method, the gene therapy method comprises the steps of administering of an isolated nucleic acid molecule encoding the heavy chain or an antigen-binding portion thereof and an isolated nucleic acid molecule encoding the light chain or the antigen-binding portion thereof of an anti-MAdCAM antibody of the invention and expressing the nucleic acid molecules. The gene therapy method may also comprise the step of administering another anti-inflammatory or immunomodulatory agent.

Another aspect of the invention is a method of diagnosis of a condition where the antibody of the invention will be useful as a medicament, by testing whether abnormal binding of an antibody of the invention occurs in the patient. This can be done using various imaging techniques well known to the skilled person, such as x-ray analysis, gamma scintigraphy, magnetic resonance imaging (MRI), positron emission tomography or computed tomography (CT) and others.

One or more inhibitory anti-MAdCAM antibodies of the invention can be used as a vaccine or as adjuvants to a vaccine, and this is another aspect of the invention. In particular, because MAdCAM is expressed in lymphoid tissue, vaccine antigens can be advantageously targeted to lymphoid tissue by conjugating the antigen to an anti-MAdCAM antibody of the invention.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics, protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual*, 2nd ed., Cold Spring Harbor Laboratory Press, Cold Spring Harbor, N.Y. (1989) and Ausubel et al., *Current Protocols in Molecular Biology*, Greene Publishing Associates (1992), and Harlow and Lane, *Antibodies: A Laboratory Manual*, Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. Standard techniques are used for chemical syntheses, chemical analyses, pharmaceutical preparation, formulation, and delivery, and treatment of patients.

The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation (1) is not associated with naturally associated components that accompany it in its native state, (2) is free of other proteins from the same species (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

A protein or polypeptide is "substantially pure," "substantially homogeneous" or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The term "polypeptide fragment" as used herein refers to a polypeptide that has an amino-terminal and/or carboxy-terminal deletion, but where the remaining amino acid sequence is identical to the corresponding positions in the naturally-occurring sequence. In some embodiments, fragments are at least 5, 6, 8 or 10 amino acids long. In other embodiments, the fragments are at least 14 amino acids long, more preferably at least 20 amino acids long, usually at least 50 amino acids long, even more preferably at least 70, 80, 90, 100, 150 or 200 amino acids long.

The term "polypeptide analog" as used herein refers to a polypeptide that comprises a segment of at least 25 amino acids that has substantial identity to a portion of an amino acid sequence and that has at least one of the following properties: (1) specific binding to MAdCAM under suitable binding conditions, (2) ability to inhibit $\alpha_4\beta_7$ integrin and/or L-selectin binding to MAdCAM, or (3) ability to reduce MAdCAM cell surface expression in vitro or in vivo. Typically, polypeptide analogs comprise a conservative amino acid substitution (or insertion or deletion) with respect to the naturally-occurring sequence. Analogs typically are at least 20 amino acids long, preferably at least 50, 60, 70, 80, 90, 100, 150 or 200 amino acids long or longer, and can often be as long as a full-length naturally-occurring polypeptide.

An "immunoglobulin" is a tetrameric molecule. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as $\kappa$ and $\lambda$ light chains. Heavy chains are classified as $\mu$, $\delta$, $\gamma$, $\alpha$, or $\epsilon$, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions to form an epitope-specific binding site. From N-terminus to C-terminus, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md. (1987 and 1991)), or Chothia & Lesk, *J. Mol. Biol.*, 196:901-917 (1987); Chothia et al., Nature, 342:878-883 (1989), each of which is incorporated herein by reference in their entirety.

The term "antibody" refers to an intact immunoglobulin or to an antigen-binding portion thereof that competes with the intact antibody for specific binding. In some embodiments, an antibody is an antigen-binding portion thereof. Antigen-binding portions may be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. A Fab fragment is a monovalent fragment consisting of the VL, VH, CL and CH1 domains; a F(ab)$_2$ fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., *Nature,* 341:544-546 (1989)) consists of a VH domain. The term is also intended to include modified versions of the antibody such as pegylated antibodies or antibodies conjugated to detectable moieties such as enzymes (e.g. horseradish peroxidase, alkaline phosphatase), radioisotopes, biotin, fluorescent labels, and others.

As used herein, an antibody that is referred to as, e.g., 1.7.2, 1.8.2, 6.14.2, 6.34.2, 6.67.1, 6.77.2, 7.16.6, 7.20.5, 7.26.4 or 9.8.2, is a monoclonal antibody that is produced by the hybridoma of the same name. For example, antibody 1.7.2 is produced by hybridoma 1.7.2. An antibody that is referred to as 6.22.2-mod, 6.34.2-mod, 6.67.1-mod, 6.77.1-mod or 7.26.4-mod is a monoclonal antibody whose sequence has been modified from its corresponding parent by site-directed mutagenesis.

A single-chain antibody (scFv) is an antibody in which VL and VH regions are paired to form a monovalent molecule via a synthetic linker that enables them to be made as a single protein chain (Bird et al., *Science*, 242:423-426 (1988) and Huston et al., *Proc. Natl. Acad. Sci. USA*, 85:5879-5883 (1988)). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al., *Proc. Natl. Acad. Sci. USA*, 90: 6444-6448 (1993) and Poljak, R. J., et al., *Structure*, 2:1121-1123 (1994)). One or more CDRs from an antibody of the invention may be incorporated into a molecule either covalently or noncovalently to make it an immunoadhesin that specifically binds to MAdCAM. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" or "bifunctional" antibody (diabody) has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. Examples of isolated antibodies include an anti-MAdCAM antibody that has been affinity purified using MAdCAM, an anti-MAdCAM antibody that has been produced by a hybridoma or other cell line in vitro, and a human anti-MAdCAM antibody derived from a transgenic mammal or plant.

As used herein, the term "human antibody" means an antibody in which the variable and constant region sequences are human sequences. The term encompasses antibodies with sequences derived from human genes, but which have been changed, e.g., to decrease possible immunogenicity, increase affinity, eliminate cysteines or glycosylation sites that might cause undesirable folding, etc. The term encompasses such antibodies produced recombinantly in non-human cells which might impart glycosylation not typical of human cells. The term also emcompasses antibodies which have been raised in a transgenic mouse which comprises some or all of the human immunoglobulin heavy and light chain loci.

In one aspect, the invention provides a humanized antibody. In some embodiments, the humanized antibody is an antibody that is derived from a non-human species, in which certain amino acids in the framework and constant domains of the heavy and light chains have been mutated so as to avoid or abrogate an immune response in humans. In some embodiments, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293. In some embodiments, a humanized anti-MAdCAM antibody of the invention comprises the amino acid sequence of one or more framework regions of one or more human anti-MAdCAM antibodies of the invention.

In another aspect, the invention includes the use of a "chimeric antibody". In some embodiments the chimeric antibody refers to an antibody that contains one or more regions from one antibody and one or more regions from one or more other antibodies. In a preferred embodiment, one or more of the CDRs are derived from a human anti-MAdCAM antibody of the invention. In a more preferred embodiment, all of the CDRs are derived from a human anti-MAdCAM antibody of the invention. In another preferred embodiment, the CDRs from more than one human anti-MAdCAM antibody of the invention are mixed and matched in a chimeric antibody. For instance, a chimeric antibody may comprise a CDR1 from the light chain of a first human anti-MAdCAM antibody may be combined with CDR2 and CDR3 from the light chain of a second human anti-MAdCAM antibody, and the CDRs from the heavy chain may be derived from a third anti-MAdCAM antibody. Further, the framework regions may be derived from one of the same anti-MAdCAM antibodies, from one or more different antibodies, such as a human antibody, or from a humanized antibody.

A "neutralizing antibody," "an inhibitory antibody" or antagonist antibody is an antibody that inhibits the binding of $\alpha_4\beta_7$ or $\alpha_4\beta_7$-expressing cells, or any other cognate ligand or cognate ligand-expressing cells, to MAdCAM by at least about 20%. In a preferred embodiment, the antibody reduces inhibits the binding of $\alpha_4\beta_7$ integrin or $\alpha_4\beta_7$-expressing cells to MAdCAM by at least 40%, more preferably by 60%, even more preferably by 80%, 85%, 90%, 95% or 100%. The binding reduction may be measured by any means known to one of ordinary skill in the art, for example, as measured in an in vitro competitive binding assay. An example of measuring the reduction in binding of $\alpha_4\beta_7$-expressing cells to MAdCAM is presented in Example I.

Fragments or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (Bowie et al., *Science*, 253:164 (1991)).

The term "$k_{off}$" refers to the off rate constant for dissociation of an antibody from the antibody/antigen complex.

The term "$K_d$" refers to the dissociation constant of a particular antibody-antigen interaction. An antibody is said to bind an antigen when the dissociation constant is $\leq 1$ µM, preferably $\leq 100$ nM and most preferably $\leq 10$ nM.

The term "epitope" includes any protein determinant capable of specific binding to an immunoglobulin or T-cell receptor or otherwise interacting with a molecule. Epitopic determinants usually consist of chemically active surface groupings of molecules such as amino acids or carbohydrate side chains and usually have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a gene mutant. Oligonucleotides of the invention can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., *Nucl. Acids Res.* 14:9081 (1986); Stec et al., *J. Am. Chem. Soc.* 106:6077 (1984); Stein et al., *Nucl. Acids Res.,* 16:3209 (1988); Zon et al., *Anti-Cancer Drug Design* 6:539 (1991); Zon et al., *Oligonucleotides and Analogues: A Practical Approach*, pp. 87-108 (F. Eckstein, Ed., Oxford University Press, Oxford England (1991)); Stec et al., U.S. Pat. No. 5,151,510; Uhlmann and Peyman, *Chemical Reviews,* 90:543 (1990), the disclosures of which are hereby incorporated by reference. An oligonucleotide can include a label for detection, if desired.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. An example of "high stringency" or "highly stringent" conditions is a method of incubating a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 μg/ml denatured, fragmented salmon sperm DNA at a hybridization temperature of 42° C. for 12-16 hours, followed by twice washing at 55° C. using a wash buffer of 1×SSC, 0.5% SDS. See also Sambrook et al., *supra*, pp. 9.50-9.55.

The term "percent sequence identity" in the context of nucleotide sequences refers to the residues in two sequences which are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.3, Accelrys, San Diego, Calif. FASTA, which includes, e.g., the programs FASTA2 and FASTA3, provides alignments and percent sequence identity of the regions of the best overlap between the query and search sequences (Pearson, *Methods Enzymol.*, 183: 63-98 (1990); Pearson, *Methods Mol. Biol.*, 132: 185-219 (2000); Pearson, *Methods Enzymol.*, 266: 227-258 (1996); Pearson, *J. Mol. Biol.*, 276: 71-84 (1998); herein incorporated by reference). Unless otherwise specified, default parameters for a particular program or algorithm are used. For instance, percent sequence identity between nucleotide sequences can be determined using FASTA with its default parameters (a word size of 6 and the NOPAM factor for the scoring matrix) or using Gap with its default parameters as provided in Wisconsin Package Version 10.3, herein incorporated by reference.

A reference to a nucleotide sequence encompasses its complement unless otherwise specified. Thus, a reference to a nucleic acid molecule having a particular sequence should be understood to encompass its complementary strand, with its complementary sequence.

In the molecular biology art, researchers use the terms "percent sequence identity", "percent sequence similarity" and "percent sequence homology" interchangeably. In this application, these terms shall have the same meaning with respect to nucleotide sequences only.

The term "substantial similarity" or "substantial sequence similarity," when referring to a nucleic acid or fragment thereof, indicates that, when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

As applied to polypeptides, the term "substantial identity" means that two peptide sequences, when optimally aligned, such as by the programs GAP or BESTFIT using default gap weights, share at least 75% or 80% sequence identity, preferably at least 90% or 95% sequence identity, even more preferably at least 98% or 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, *Methods Mol. Biol.*, 24: 307-31 (1994), herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; and 6) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., *Science*, 256: 1443-45 (1992), herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., Wisconsin package Version 10.3. Polypeptide sequences also can be compared using FASTA using default or recommended parameters, a program in Wisconsin package Version 10.3. FASTA (e.g., FASTA2 and FASTA3) provides alignments and percent sequence identity of the regions of the best overlap between the query and search sequences (Pearson (1990); Pearson (2000)). Another preferred algorithm when comparing a sequence of the invention to a database containing a large number of sequences from different organisms is the computer program BLAST, especially blastp or tblastn, using default parameters. See, e.g., Altschul et al., *J. Mol. Biol.* 215: 403-410 (1990); Altschul et al., Nucleic Acids Res. 25:3389-402 (1997); herein incorporated by reference.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences.

As used herein, the terms "label" or "labeled" refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The following examples are for purposes of illustration only and are not to be construed as limiting the scope of the invention in any manner.

EXAMPLES

Example 1

Identification of Potential Immunogenic Epitopes

CD4$^+$ T (helper) cell epitopes are critical in driving T cell dependent immune responses to protein antigens. During the initiation of a T-cell dependent immune response dendritic cells capture, process and present protein antigen in the form of linear peptides bound in the groove of MHC class II. Binding of the T-cell receptor to the peptide/MHC-II complex by naïve CD4$^+$ T cells can trigger a cascade in which T cells proliferate, differentiate and provide help by producing co-stimulatory cytokines (e.g. IL-4, IL-6) and by direct cell-cell contact (e.g. CD40) to B cells. The continued help from T cells is required during secondary B cell lymphopoiesis in which B cells rearrange their immunoglobulin chains to produce high affinity isotype switched immunoglobulin against the same antigen recognised by the T cells. It is the binding of the B cell produced immunoglobulins that can neutralise the effects of protein-based therapies. The identification of T cell epitopes contained within therapeutic antibodies is important in predicting immunogenicity in man. With their identification it may be desirable to engineer the MHC-II anchors out by site directed mutagenesis, generating non-immunogenic adducts that retain the therapeutic activity of the parent.

Six fully human anti-MAdCAM mAbs, 6.22.2-mod, 6.34.2-mod, 6.67.1-mod, 6.77.1-mod, 7.16.6 and 9.8.2 (previously described in WO2005/067620; hybridomas secreting 7.16.6 and 9.8.2 were deposited in the European Collection of Cell Cultures (ECACC), H.P.A at CAMR, Porton Down, Salisbury, Wiltshire SP4 0JG on 9$^{th}$ Sep. 2003 with the following deposit numbers: 7.16.6: Deposit No: 03090909; 9.8.2: Deposit No: 03090912), were subjected to an ex vivo assessment to identify potential T cell epitopes and determine their immunogenicity. Sequence overlapping peptides (15 mers of purity >90%) covering the framework (FR) and complementary determining regions (CDRs) of the heavy and kappa light chain counterparts of 6.22.2, 6.34.2, 6.67.1, 6.77.1, 7.16.6 and 9.8.2 were synthesised using standard methods. The peptides were screened against a panel of 40 human donors in multiple cultures of CD8$^+$ T-cell depleted PMSC, providing a source of CD4$^+$ cells and antigen presenting cells at physiological ratios. The 40 healthy donors were selected for screening on the basis of HLA-DR typing and represented >80% of the DR alleles expressed in the world's population. Individual peptides (1 and 5 µM) were screened in sextuplicate, in conjunction with two positive control peptides. Cells were treated with peptides for 7 days, then proliferation was measured by incorporation of $^3$H-thymidine (0.5 µCi/well; 18 hrs). The incorporation of radiolabel was determined by scintillation counting and expressed as a stimulation index (SI) as follows:

$$SI = \frac{cpm \text{ of test peptide}}{Cpm \text{ of untreated control}}$$

A T-cell epitope is defined as a peptide giving a SI>2 in two or more independent donors.

In addition to the peptide-induced proliferation response, peptides were tested on PBMC donors in an ELISPOT assay. This method captures released cytokines and enables quantification of activated cells within the whole population. The release of IL-2, the principle cytokine secreted by activated CD4$^+$ T cells, was selected to identify T-cell stimulated by the peptide epitope. As with the proliferation assay, donor samples were incubated with peptide for 7 days prior to assessment. On analysis each stimulated T cell was represented as a spot of IL-2 release. For each donor and peptide (1 and 5 µM) combination the number of spots/well were determined and a stimulation index calculated as a ratio:

$$SI = \frac{\text{spots/well of test peptide}}{\text{spots/well of untreated control}}$$

In general there should be good overlap in the responses observed between the proliferation and ELISPOT assays, though differences in the kinetics and magnitude of responses between the two assays can lead to some lack of correlation.

Table 1 describes the data from the T-cell proliferation and ELISPOT assays. Based on these analyses, T cell epitopes were identified in FR2/CDR2 region of the 6.22.2-mod heavy chain; CDR2, FR3/CDR3 and CDR3 of the kappa light chain of 6.34.2-mod light chain; FR3/CDR3 of the 6.67.1-mod kappa light chain; CDR3 of the 6.77.1-mod heavy chain; CDR2 of the 7.16.6 heavy chain and FR3/CDR3 of the 7.16.6 kappa light chain; and FR3/CDR3 of the 9.8.2 heavy chain.

Table 1. The induction of T cell proliferation and IL-2 production in PBMCs from 40 healthy volunteers incubated with different peptides derived from the anti-MAdCAM mAbs 6.22.2-mod, 6.34.2-mod, 6.67.1-mod, 6.77.1-mod, 7.16.6 and 9.8.2. The sequences of each peptide are indicated, residues which differ from the germine sequence are in bold.

TABLE 1

| Antibody | Chain | Sequence | Proliferation (SI >2) | ELIISPOT (SI >2) |
|---|---|---|---|---|
| 6.22.2 | Heavy | SGFTFSSDGMHWVRQ (SEQ ID NO: 39) | | 1 |
| | | EWVAIIWYDGSNKYY | 2 | |
| | Light | RASQRIGSSLHWYQQ | | 1 |

TABLE 1-continued

| Antibody | Chain | Sequence | Proliferation (SI >2) | ELIISPOT (SI >2) |
|---|---|---|---|---|
| 6.34.2 | Heavy | AVISNDGNNKYYADS | | 1 |
| | Light | ISSYLNWFQQKPGKA | 1 | |
| | | YLNWFQQKPGKAPKL | 1 | 1 |
| | | APKLLIYAASGLKRG | 3 | 1 |
| | | LLIYAASGLKRGVPS | 1 | 1 |
| | | SGLKRGVPSRFSGSG | 1 | |
| | | QPEDFATYYCHQSYS | 1 | |
| | | DFATYYCHQSYSLPF | 2 | |
| | | CHQSYSLPFTFGPGT | 1 | 3 |
| | | SYSLPFTFGPGTKVD | | 1 |
| 6.67.1 | Heavy | GRIYTSGGTNSNPSL | 1 | |
| | | RDRITIIRGLIPSFF | 1 | |
| | | ITIIRGLIPSFFDYW | 1 | |
| | | LIPSFFDYWGQGTLV | 1 | |
| | Light | PPKLLIYWASIREYG | 1 | |
| | | AEDVAVYFCQQYYSI | | 1 |
| | | VAVYFCQQYYSIPPL | | 3 |
| | | YFCQQYYSIPPLTFG | | 1 |
| | | YSIPPLTFGGGTKVE | 1 | |
| 6.77.1 | Heavy | AVYYCARDGYSSQWS | 1 | |
| | | RDGYSSGWSYYYYYG | 1 | |
| | | YSSGWSYYYYYGMDV | 3 | |
| | | GWSYYYYYGMDVWGQ | 4 | |
| | Light | ISCKSSQSLLLSDGK | 1 | |
| | | EAEDVGVYSCMQSIQ | 1 | |
| | | VYSCMQSIQLMSSFG | 1 | |
| | | SIQLMSSFGQGTKLE | 1 | 1 |
| 7.16.6 | Heavy | SVYSGNTNYAQKVQG | 2 | |
| | | AVYYCAREGSSSSGD | 1 | |
| | | SGDYYYGMDVWGQGT | 1 | |
| | Light | VEAEDVGIYYCMQNI | 1 | |
| | | EDVGIYYCMQNIQLP | 4 | 4 |
| | | GIYYCMQNIQLPWTF | 1 | 1 |
| 9.8.2 | heavy | VAVIWYDGSNEYYAD | | 1 |
| | | IWYDGSNEYYADSVK | 1 | 1 |
| | | AEDTAVYYCARGAYH | 1 | 1 |
| | | TAVYYCARGAYHFAY | 3 | |
| | | ARGAYHFAYWGQGTL | 1 | |
| | Light | SLQPEDIATYSCQHS | 1 | |
| | | PEDIATYSCQHSDNL | 1 | |
| | | IATYSCQHSDNLTFG | 1 | |
| | | YSCQHSDNLTFGQGT | 1 | |

Example 2

Characterisation of Modified Variants of 7.16.6

The T-cell proliferation and ELISPOT analysis identified a number of potential T-cell epitopes in the MAdCAM mAbs 6.22.2-mod, 6.34.2-mod, 6.67.1-mod, 6.77.1-mod, 7.16.6 and 9.8.2. The major T-cell epitope in the kappa light chain of 7.16.6 was reverted to germline by site directed mutagenesis (QuikChange, Stratagene) according to manufacturer's instructions. The sequences of the oligonucleotides used to generate the modified forms are indicated below: primer pairs 7.16.6_V5 and 7.16.6_V3 were used to generate the 7.16.6_V adduct (VH=wild type; VL=190V); 7.16.6_S5 and 7.16.6_S3 were used to generate the 7.16.6_S adduct (VH=wild type; VL=N96S); 7.16.6_VS5 and 7.16.6_VS3 were used to generate the 7.16.6_VS adduct (VH=wild type; VL=190V, N96S). The pEE12.1 vector containing the 7.16.6 heavy chain cDNA (described in WO2005/067620). Briefly, a functional eukaryotic expression vector containing the respective heavy and light chain sequences were assembled as follows: The heavy chain cDNA inserts were excised from the required pEE6.1 with NotI/SalI, and the purified fragments were cloned into identical sites into the corresponding pEE12.1 vector containing the required versions of the kappa light chain sequences.) was used as a template for the QuikChange PCR.

```
7.16.6_V5    GGCTGAGGATGTTGGGGTTTATTACTGCATGC              (SEQ ID NO: 84)

7.16.6_V3    GCATGCAGTAATAAACCCCAACATCCTCAGCC              (SEQ ID NO: 85)

7.16.6_S5    CTGCATGCAAAGTATACAGCTTCCGTGGAC                (SEQ ID NO: 86)

7.16.6_S3    GTCCACGGAAGCTGTATACTTTGCATGCAG                (SEQ ID NO: 87)

7.16.6_VS5   GGATGTTGGGGTTTATTACTGCATGCAAAGTATACAGCTTCCG   (SEQ ID NO: 88)

7.16.6_VS3   CGGAAGCTGTATACTTTGCATGCAGTAATAAACCCCAACATCC   (SEQ ID NO: 89)
``` pEE12.1 constructs containing the modified kappa light chains of 7.16.6_V, 7.16.6__5 and 7.16.6_VS along with the parent 7.16.6 heavy chain were generated from the QuikChange PCR products and fully sequence verified. A similar PCR approach was used to generate the 7.16.6_L variant (VH=V64L, VL=wild type), using the following oligonucleotides and QuikChange PCR:

```
7.16.6_L5
CTATGCACAGAAGCTTCAGGGCAGAGTCAC                (SEQ ID NO: 90)

7.16.6_L3
GTGACTCTGCCCTGAAGCTTCTGTGCATAG                (SEQ ID NO: 91)
```

Parent kappa light chain and 7.16.6_VS variant were used to generate the 7.16.6_L and 7.16.6_LVS (VH=V64L; VL=190V, N96S) variant as described in WO2005/067620. Recombinant material was purified by affinity chromatography from FreeStyle HEK293 cells (Invitrogen) transiently transfected with the appropriate construct.

The purified antibodies were assessed for activity in an adhesion assay using MAdCAM-IgG$_1$ Fc fusion protein:

An EcoRI/BglII cDNA fragment encoding the mature extracellular, immunoglobulin-like domain of MAdCAM was excised from a pINCY Incyte clone (3279276) and cloned into EcoRI/BamHI sites of the pIG1 vector (Simmons, D. L. (1993) in *Cellular Interactions in Development: A Practical Approach*, ed. Hartley, D. A. (Oxford Univ. Press, Oxford), pp. 93-127.)) to generate an in frame IgG$_1$ Fc fusion. The resulting insert was excised with EcoRI/NotI and cloned into pcDNA3.1+ (Invitrogen). The MAdCAM-IgG$_1$ Fc cDNA in the vector was sequence confirmed. The amino acid sequence of the MAdCAM-IgG$_1$ Fc fusion protein is shown below:

```
MDFGLALLLAGLLGLLLGQSLQVKPLQVEPPEPVVAVALGASRQLTCRLACADRGASVQWRGLDT  (SEQ ID NO: 92)

SLGAVQSDTGRSVLTVRNASLSAAGTRVCVGSCGGRTFQHTVQLLVYAFPDQLTVSPAALVPGDP

EVACTAHKVTPVDPNALSFSLLVGGQELEGAQALGPEVQEEEEEPQGDEDVLFRVTERWRLPPLG

TPVPPALYCQATMRLPGLELSHRQAIPVLHSPTSPEPPDTTSPESPDTTSPESPDTTSQEPPDTT

SQEPPDTTSQEPPDTTSPEPPDKTSPEPAPQQGSTHTPRSPGSTRTRRPEIQPKSCDKTHTCPPC

PAPELLGGPSVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYTLPPSRDELT

KNQVSLTCLVKGFYPSDIAVEWESNGQPENNYKATPPVLDSDGSFFLYSKLTVDKSRWQQGNVFS

CSVMHEALHNHYTQKSLSLSPGK
Underlined: signal peptide
Bold: MAdCAM extracellular domain
```

CHO-DHFR cells were transfected with pcDNA3.1+ vector containing MAdCAM-IgG$_1$ Fc fusion protein cDNA and stable clones expressing MAdCAM-IgG$_1$ Fc fusion protein selected in Iscove's media containing 600 µg/mL G418 and 100 ng/mL methotrexate. For protein expression, a hollow fibre bioreactor was seeded with stably expressing MAdCAM-IgG$_1$ Fc CHO cells in Iscove's media containing 10% low IgG fetal bovine serum (Gibco), non essential amino acids (Gibco), 2 mM glutamine (Gibco), sodium pyruvate (Gibco), 100 µg/mL G418 and 100 ng/mL methotrexate, and used to generate concentrated media supernatant. The MAdCAM-IgG$_1$ Fc fusion protein was purified from the harvested supernatant by affinity chromatography. Briefly, supernatant was applied to a HiTrap Protein G Sepharose (5 mL, Pharmacia) column (2 mL/min), washed with 25 mM Tris pH 8, 150 mM NaCl (5 column volumes) and eluted with 100 mM glycine pH 2.5 (1 mL/min), immediately neutralising fractions to pH 7.5 with 1 M Tris pH 8. Fractions containing MAdCAM-IgG$_1$ Fc fusion protein were identified by SDS-PAGE, pooled together and applied to a Sephacryl S100 column (Pharmacia), pre-equilibrated with 35 mM BisTris pH 6.5, 150 mM NaCl. The gel filtration was performed at 0.35 mL/min, collecting a peak of MAdCAM-IgG$_1$ Fc fusion protein in ca. 3×5 mL fractions. These samples were pooled and applied to a Resource Q (6 mL, Pharmacia) column, pre-equilibrated in 35 mM BisTris pH6.5. The column was washed with 5 column volumes of 35 mM Bis Tris pH 6.5, 150 mM NaCl (6 mL/min) and MAdCAM-IgG$_1$ Fc fusion protein eluted into a 4-6 mL fraction with 35 mM Bis Tris pH 6.5, 400 mM NaCl. At this stage the protein was 90% pure and migrating as a single band at approximately 68 kD by SDS-PAGE. For use as an immunogen and all subsequent assays, the material was buffer exchanged into 25 mM HEPES pH 7.5, 1 mM EDTA, 1 mM DTT, 100 mM NaCl, 50% glycerol and stored as aliquots at −80° C.

100 µL of a 4.5 µg/mL solution of purified MAdCAM-IgG$_1$ Fc fusion protein in Dulbecco's PBS was adsorbed to 96 well Black Microfluor "B" u-bottom (Dynex #7805) plates overnight at 4° C. The MAdCAM coated plates were then inverted and excess liquid blotted off, prior to blocking at 37° C. for at least 1 hour in 10% BSA/PBS. During this time cultured JY cells were counted using tryptan blue exclusion (should be approximately 8×10$^5$ cells/mL) and 20×10$^6$ cells/assay plate pipetted into a 50 mL centrifuge tube. JY cells were cultured in RPMI1640 media (Gibco), containing 2 mM L-glutamine and 10% heat-inactivated fetal bovine serum (Life Technologies #10108-165) and seeded at 1–2×10$^5$/mL every 2-3 days to prevent the culture from differentiating. The cells were washed twice with RPMI 1640 media (Gibco) containing 2 mM L-glutamine (Gibco) by centrifugation (240 g), resuspending the final cell pellet at 2×10$^6$ cells/mL in RPMI 1640 for Calcein AM loading. Calcein AM (Molecular Probes #C-3099) was added to the cells as a 1:200 dilution in DMSO (ca. final concentration 5 µM) and the cells protected from light during the course of the incubation (37° C. for 30 min). During this cell incubation step the antibodies to be tested, were diluted as follows: for single dose testing, the antibodies were made up to 3 µg/mL (1 µg/mL final) in 0.1 mg/mL BSA (Sigma#A3059) in PBS; for full IC$_{50}$ curves, the antibodies were diluted in 0.1 mg/mL BSA/PBS, with 3 µg/mL (1 µg/mL final) being the top concentration, then doubling dilutions (1:2 ratio) across the plate. The final well of the row was used for determining total binding, so 0.1 mg/ml BSA in PBS was used.

After blocking, the plate contents were flicked out and 50 µL of antibodies/controls were added to each well and the plate incubated at 37° C. for 20 min. During this time, Calcein-loaded JY cells were washed once with RPMI 1640 media containing 10% fetal bovine serum and once with 1 mg/mL BSA/PBS by centrifugation, resuspending the final cell pellet to 1×10$^6$/mL in 1 mg/mL BSA/PBS. 100 µL of cells were added to each well of the U bottomed plate, the plate sealed, briefly centrifuged (1000 rpm for 2 min) and the plate then incubated at 37° C. for 45 min. At the end of this time, the plates were washed with a Skatron plate washer and fluorescence measured using a Wallac Victor$^2$ 1420 Multilabel Reader (excitation λ485 nm, emission λ535 nm count from top, 8 mm from bottom of plate, for 0.1 sec with normal emission aperture). For each antibody concentration, percent adhesion was expressed as a percentage of maximal fluorescence response in the absence of any antibody minus fluorescence associated with non-specific binding. The $IC_{50}$ value is defined as the anti-MAdCAM antibody concentration at which the adhesion response is decreased to 50% of the response in the absence of anti-MAdCAM antibody. Antibodies that were able to inhibit the binding of JY cells to MAdCAM-IgG$_1$ Fc fusion with an $IC_{50}$ value <0.1 μg/mL, were considered to have potent antagonist activity and were progressed to the MAdCAM-CHO adhesion assay.

The $IC_{50}$ values are summarised in Table 2 (all datapoints given in μg/mL):

TABLE 2

Kd, $k_a$, and $k_d$ values for the interaction of MAdCAM with the anti-MAdCAM antibody 7.16.6 and 5 clones derived from it.

|  | Kd (pM) | $k_a$ ($M^{-1}s^{-1}$) | $k_d$ ($s^{-1}$) | $IC_{50}$ (ng/mL) | s.d | n |
|---|---|---|---|---|---|---|
| 7.16.6 | 7.3 | $3.3 \times 10^5$ | $2.42 \times 10^{-6}$ * | 24.7 | 7.6 | 6 |
| 7.16.6_S | 23.2 | $1.83 \times 10^5$ | $4.27 \times 10^{-6}$ * | 34.2 | 7.4 | 5 |
| 7.16.6_V | 162 | $1.53 \times 10^5$ | $2.49 \times 10^{-5}$ | 41.2 | 20.9 | 5 |
| 7.16.6_VS | 90.8 | $2.40 \times 10^5$ | $2.18 \times 10^{-5}$ | 58.2 | 51.2 | 5 |
| 7.16.6_L | 79.5 | $1.52 \times 10^5$ | $1.21 \times 10^{-5}$ | 35.6 | 10 | 5 |
| 7.16.6_LVS | 119 | $1.94 \times 10^5$ | $2.31 \times 10^{-5}$ | 45.8 | 16.4 | 5 |

* Indicates that these off rate values are just below the lower limit ($5 \times 10^{-6} s^{-1}$) for BIAcore.
The affinity (KD) values should therefore more accurately be quoted as:
<15 pM (=$5 \times 10^{-6}/3.3 \times 10^5$) for 7.16.6 and
<27.3 pM (=$5 \times 10^{-6}/1.83 \times 10^5$) for 7.16.6_V
The off rates for the other four antibodies are within the limits of the instrument.

The results show that the variants still bind MAdCAM with high affinity, sufficiently high for therapeutic use.

7.16.6, 7.16.6_V, 7.16.6_S, 7.16.6_VS, 7.16.6_L and 7.16.6_LVS also bound to CHO cells expressing MAdCAM, as detected by flow cytometry.

The Kd values shown in Table 2 were determined by BIAcore, essentially as described in Example II in WO 2005/067620, with the following modifications:

Sample Injections

Flow cells used: Either 2 with 1 as a reference, or 4 with 3 as a reference

Flow rate: 100 μL/min

Injection time: 2 minutes

Wait after injection: 60 minutes (=dissociation time)

Injection cycles: Triplicate of all concentrations, plus six injections of buffer blank Regeneration Method Solution/flow rate/injection time:

| Immobilised antibody | Regeneration solution | Regeneration flow rate, μL/min | Injection time (vol) |
|---|---|---|---|
| 7.16.6 | 50 mM Phosphoric Acid | 50 | 12 seconds (10 μL) |
| 7.16.6_V | 60 mM Phosphoric Acid | 50 | 54 seconds (45 μL) |
| 7.16.6_S | 4M Magnesium Chloride | 100 | 15 seconds (25 μL) |
| 7.16.6_VS | 50 mM Phosphoric Acid | 50 | 12 seconds (10 μL) |
| 7.16.6_L | 7.5 mM Sodium Hydroxide | 50 | 6 seconds (5 μL) |
| 7.16.6_LVS | 5 mM Sodium Hydroxide | 50 | 6 seconds (5 μL) |

Stabilisation time after regeneration: 5 minutes

Example 3

Immunohistochemistry Staining of Cynomolgus Tissues with Variants of 7.16.6

Immunohistochemistry was essentially performed as described in Example III in WO 2005/067620. The results are summarized in Table 3 below.

TABLE 3

Summary of staining of normal cynomolgus tissues with anti-hMAdCAM 1/500 dilution (ca. 0.3 μg/mL), 1 hour incubation at room temperature).

| | | | 7.16.6_LVS | 7.16.6_L | 7.16.6_ | 7.16.6_S | 7.16.6_VS | Neg. Control Tissue |
|---|---|---|---|---|---|---|---|---|
| | | | Positive staining | | | | | |
| Ileum/Peyer's Patch (PP) | 2-3+ | HEV (PP), Vasc. endothelium (lamina propria-LP) | = | > | = | = | = | <<< |
| Cecum | 3+ | vasc. endothelium (LP) | = | = | = | = | = | <<< |
| Spleen | 2-4+ | Sinus-lining cells (marginal zone of white pulp) | < | = | = | < | < | <<< |
| Mesenteric LN | 4+ | HEV | = | = | = | = | = | <<< |
| Axillary LN | trace | Dendritic-like cells around lymphoid follicles | = | = | = | = | = | <<< |
| Pancreas | 1+ | Vas endothelium (venules of exocrine lobules) | = | = | < | = | = | <<< |

TABLE 3-continued

Summary of staining of normal cynomolgus tissues with anti-hMAdCAM 1/500 dilution (ca. 0.3 µg/mL), 1 hour incubation at room temperature).

|  |  |  | 7.16.6_LVS | 7.16.6_L | 7.16.6_ | 7.16.6_S | 7.16.6_VS | Neg. Control Tissue |
|---|---|---|---|---|---|---|---|---|
| Negative Staining |
| Kidney* | 0 | — | = | = | = | = | = | = |
| Heart (ventricle) | 0 | — | = | = | = | = | = | = |
| Thyroid | 0 | — | = | = | = | = | = | = |

Strong staining in tubules attributable to non-specific binding of the secondary antibody and interpreted as background noise.

Example 4

Characterisation of Modified Variants of 6.22.2, 6.34.2, 6.67.1, 6.77.1 and 9.8.2

Using similar methods as described here in Example 2 and referred to in WO2005/067620, some of the significant potential T cell epitopes in 6.22.2, 6.34.2, 6.67.1, 6.77.1 and 9.8.2 described in Table 1 were modified to germlne by substitution or deletion to generate purified recombinant 6.22.2-mod_V (SEQ ID No. 2), 6.34.2_mod_SSQ (SEQ ID No. 8), 6.67.1-mod_Y (SEQ ID No. 14), 6.77.1-mod_ΔAS (SEQ ID No. 22) and 9.8.2-mod_ΔRGAYH,D (SEQ ID No. 36) chain variants. The $IC_{50}$ potencies of the following mAbs referred to as 6.22.2-mod_V (SEQ ID Nos. 2 and 4), 6.34.2_mod_SSQ (SEQ ID Nos. 6 and 8), 6.67.1-mod_Y (SEQ ID Nos. 14 and 20), 6.77.1-mod_ΔAS (SEQ ID Nos. 22 and 24) and 9.8.2-mod_ΔRGAYH,D (SEQ ID Nos. 36 and 38) in the MAdCAM-$IgG_1$ Fc fusion: JY cell binding assay are represented in Table 4 compared with their parental counterpart 6.22.2, 6.34.2, 6.67.1, 6.77.1 and 9.8.2 mAbs. All modified variants maintained similar antagonist potency to their parental mAbs.

TABLE 4

Comparison of $IC_{50}$ potencies of the 6.22.2, 6.34.2, 6.67.1, 6.77.1 and 9.8.2 modified mAbs, 6.22.2-mod_V, 6.34.2_mod_SSQ, 6.67.1-mod_Y, 6.77.1-mod_ΔAS and 9.8.2-mod_ΔRGAYH,D respectively in the MAdCAM-$IgG_1$ Fc fusion: JY cell binding assay

| | $IC_{50}$ (μg/mL) | S.D | n | | $IC_{50}$ (μg/mL) | S.D | n |
|---|---|---|---|---|---|---|---|
| 6.22.2 | 0.018 | 0.0109 | 4 | 6.22.2-mod_V | 0.076 | 0.033 | 7 |
| 6.34.2 | 0.013 | 0.0079 | 4 | 6.34.2-mod_SSQ | 0.086 | 0.04 | 11 |
| 6.67.1 | 0.013 | 0.0071 | 4 | 6.67.1-mod_Y | 0.063 | 0.025 | 6 |
| 6.77.1 | 0.022 | 0.0045 | 4 | 6.77.1-mod_ΔAS | 0.0485 | 0.0135 | 7 |
| 9.8.2 | 0.02 | 0.0047 | 4 | 9.8.2_ΔRGAYH,D | 0.072 | 0.03 | 6 |

Sequences:

The sequences of the signal peptide sequence (or the bases encoding the same) are indicated in lower case and underlined. The variable regions are in upper case. The constant regions are in upper case and underlined in the protein sequences. Bold are residues modified from the originally disclosed sequences (WO2005/067620).

```
SEQ ID NO: 1
6.22.2-mod_V Heavy Chain Nucleotide Sequence
  1   atggagtttg ggctgagctg ggttttcctc gttgctcttt taagaggtgt 51   ccagtgtCAG GTGCAGCTGG TGGAGTCTGG GGGAGGCGTG GTCCAGCCTG

101   GGAGGTCCCT GAGACTCTCC TGTGCAGCGT CTGGATTCAC CTTCAGTAGC

151   GATGGCATGC ACTGGGTCCG CCAGGCTCCA GGCAAGGGGC TGGAGTGGGT

201   GGCAGTGATA TGGTATGATG GAAGTAATAA ATATTATGCA GACTCCGTGA

251   AGGGCCGATT CACCATCTCC AGAGACAATT CCAAGAACAC GCTGTATCTG

301   CAAATGAACA GCCTGAGAGC CGAGGACACG GCTGTATATT ACTGTGCGAG

351   AGATCCCGGC TACTATTACG GTATGGACGT CTGGGGCCAA GGGACCACGG

401   TCACCGTCTC CTCAGCTTCC ACCAAGGGCC CATCCGTCTT CCCCCTGGCG

451   CCCTGCTCTA GAAGCACCTC CGAGAGCACA GCGGCCCTGG GCTGCCTGGT
```

-continued

```
 501 CAAGGACTAC TTCCCCGAAC CGGTGACGGT GTCGTGGAAC TCAGGCGCTC
 551 TGACCAGCGG CGTGCACACC TTCCCAGCTG TCCTACAGTC CTCAGGACTC
 601 TACTCCCTCA GCAGCGTGGT GACCGTGCCC TCCAGCAACT TCGGCACCCA
 651 GACCTACACC TGCAACGTAG ATCACAAGCC CAGCAACACC AAGGTGGACA
 701 AGACAGTTGA GCGCAAATGT TGTGTCGAGT GCCCACCGTG CCCAGCACCA
 751 CCTGTGGCAG GACCGTCAGT CTTCCTCTTC CCCCCAAAAC CCAAGGACAC
 801 CCTCATGATC TCCCGGACCC CTGAGGTCAC GTGCGTGGTG GTGGACGTGA
 851 GCCACGAAGA CCCCGAGGTC CAGTTCAACT GGTACGTGGA CGGCGTGGAG
 901 GTGCATAATG CCAAGACAAA GCCACGGGAG GAGCAGTTCA ACAGCACGTT
 951 CCGTGTGGTC AGCGTCCTCA CCGTTGTGCA CCAGGACTGG CTGAACGGCA
1001 AGGAGTACAA GTGCAAGGTC TCCAACAAAG GCCTCCCAGC CCCCATCGAG
1051 AAAACCATCT CCAAAACCAA AGGGCAGCCC CGAGAACCAC AGGTGTACAC
1101 CCTGCCCCCA TCCCGGGAGG AGATGACCAA GAACCAGGTC AGCCTGACCT
1151 GCCTGGTCAA AGGCTTCTAC CCCAGCGACA TCGCCGTGGA GTGGGAGAGC
1201 AATGGGCAGC CGGAGAACAA CTACAAGACC ACACCTCCCA TGCTGGACTC
1251 CGACGGCTCC TTCTTCCTCT ACAGCAAGCT CACCGTGGAC AAGAGCAGGT
1301 GGCAGCAGGG GAACGTCTTC TCATGCTCCG TGATGCATGA GGCTCTGCAC
1351 AACCACTACA CGCAGAAGAG CCTCTCCCTG TCTCCGGGTA AATGATAG
```

SEQ ID NO: 2  
6.22.2-mod_V Predicted Heavy Chain Protein Sequence

```
   1 mefglswvfl vallrqvqcQ VQLVESGGGV VQPGRSLRLS CAASGFTFSS
  51 DGMHWVRQAP GKGLEWVAVI WYDGSNKYYA DSVKGRFTIS RDNSKNTLYL
 101 QMNSLRAEDT AVYYCARDPG YYYGMDVWGQ GTTVTVSSAS TKGPSVFPLA
 151 PCSRSTSEST AALGCLVKDY FPEPVTVSWN SGALTSGVHT FPAVLQSSGL
 201 YSLSSVVTVP SSNFGTQTYT CNVDHKPSNT KVDKTVERKC CVECPPCPAP
 251 PVAGPSVFLF PPKPKDTLMI SRTPEVTCVV VDVSHEDPEV QFNWYVDGVE
 301 VHNAKTKPRE EQFNSTFRVV SVLTVVHQDW LNGKEYKCKV SNKGLPAPIE
 351 KTISKTKGQP REPQVYTLPP SREEMTKNQV SLTCLVKGFY PSDIAVEWES
 401 NGQPENNYKT TPPMLDSDGS FFLYSKLTVD KSRWQQGNVF SCSVMHEALH
 451 NHYTQKSLSL SPGK
```

SEQ ID NO: 3  
6.22.2-mod Kappa Light Chain Nucleotide Sequence

```
   1 atgttgccat cacaactcat tgggtttctg ctgctctggg ttccagcttc
  51 cagggqtGAA ATTGTGCTGA CTCAGTCTCC AGACTTTCAG TCTGTGACTC
 101 CAAAAGAGAA AGTCACCATC ACCTGCCGGG CCAGTCAGAG AATTGGTAGT
 151 AGCTTACACT GGTACCAGCA GAAACCAGAT CAGTCTCCAA AACTCCTCAT
 201 CAAGTATGCT TCCCAGTCCT TCTCAGGGGT CCCCTCGAGG TTCAGTGGCA
 251 GTGGATCTGG GACAGATTTC ACCCTCACCA TCAATAGCCT GGAAGCTGAA
 301 GATGCTGCAA CTTATTACTG TCATCAGAGT GGTCGTTTAC CGCTCACTTT
 351 CGGCGGAGGG ACCAAGGTGG AGATCAAACG AACTGTGGCT GCACCATCTG
 401 TCTTCATCTT CCCGCCATCT GATGAGCAGT TGAAATCTGG AACTGCCTCT
 451 GTTGTGTGCC TGCTGAATAA CTTCTATCCC AGAGAGGCCA AGTACAGTG
 501 GAAGGTGGAT AACGCCCTCC AATCGGGTAA CTCCCAGGAG AGTGTCACAG
```

-continued

```
551   AGCAGGACAG CAAGGACAGC ACCTACAGCC TCAGCAGCAC CCTGACGCTG

601   AGCAAAGCAG ACTACGAGAA ACACAAAGTC TACGCCTGCG AAGTCACCCA

651   TCAGGGCCTG AGCTCGCCCG TCACAAAGAG CTTCAACAGG GGAGAGTGTT

701   AGTGA
```

SEQ ID NO: 4
6.22.2-mod Predicted Kappa Light Chain Amino Acid Sequence
```
  1   mlpsqliqfl llwvpasrgE IVLTQSPDFQ SVTPKEKVTI TCRASQRIGS

51   SLHWYQQKPD QSPKLLIKYA SQSFSGVPSR FSGSGSGTDF TLTINSLEAE

101   DAATYYCHQS GRLPLTFGGG TKVEIKRTVA APSVFIFPPS DEQLKSGTAS

151   VVCLLNNFYP REAKVQWKVD NALQSGNSQE SVTEQDSKDS TYSLSSTLTL

201   SKADYEKHKV YACEVTHQGL SSPVTKSFNR GEC
```

SEQ ID NO. 5
6.34.2-mod Heavy Chain Nucleotide Sequence
```
  1   atggagtttg ggctgagctg ggttttcctc gttgctcttt taagaggtgt 51   ccagtgtCAG GTGCAGCTGG TGGAGTCTGG GGGAGGCGTG GTCCAGCCTG

101   GGAGGTCCCT GAGACTCTCC TGTGCAGCCT CTGGATTCAC CTTCAGTAGC

151   TATGGCATGC ACTGGGTCCG CCAGGCTCCA GGCAAGGGGC TGGAGTGGGT

201   GGCAGTTATA TCAAATGATG GAAATAATAA ATACTATGCA GACTCCGTGA

251   AGGGCCGATT CACCATCTCC AGAGACAATT CCAAAAACAC GCTGTATCTG

301   CAAATGAACA GCCTGCGCGC TGAGGACACG GCTGTGTATT ACTGTGCGAG

351   AGATAGTACG GCGATAACCT ACTACTACTA CGGAATGGAC GTCTGGGGCC

401   AAGGGACCAC GGTCACCGTC TCCTCAGCTT CCACCAAGGG CCCATCCGTC

451   TTCCCCCTGG CGCCCTGCTC TAGAAGCACC TCCGAGAGCA CAGCGGCCCT

501   GGGCTGCCTG GTCAAGGACT ACTTCCCCGA ACCGGTGACG GTGTCGTGGA

551   ACTCAGGCGC TCTGACCAGC GGCGTGCACA CCTTCCCAGC TGTCCTACAG

601   TCCTCAGGAC TCTACTCCCT CAGCAGCGTG GTGACCGTGC CCTCCAGCAA

651   CTTCGGCACC CAGACCTACA CCTGCAACGT AGATCACAAG CCCAGCAACA

701   CCAAGGTGGA CAAGACAGTT GAGCGCAAAT GTTGTGTCGA GTGCCCACCG

751   TGCCCAGCAC CACCTGTGGC AGGACCGTCA GTCTTCCTCT TCCCCCCAAA

801   ACCCAAGGAC ACCCTCATGA TCTCCCGGAC CCCTGAGGTC ACGTGCGTGG

851   TGGTGGACGT GAGCCACGAA GACCCCGAGG TCCAGTTCAA CTGGTACGTG

901   GACGGCGTGG AGGTGCATAA TGCCAAGACA AAGCCACGGG AGGAGCAGTT

951   CAACAGCACG TTCCGTGTGG TCAGCGTCCT CACCGTTGTG CACCAGGACT

1001  GGCTGAACGG CAAGGAGTAC AAGTGCAAGG TCTCCAACAA AGGCCTCCCA

1051  GCCCCCATCG AGAAAACCAT CTCCAAAACC AAAGGGCAGC CCGAGAACC

1101  ACAGGTGTAC ACCCTGCCCC CATCCCGGGA GGAGATGACC AAGAACCAGG

1151  TCAGCCTGAC CTGCCTGGTC AAAGGCTTCT ACCCCAGCGA CATCGCCGTG

1201  GAGTGGGAGA GCAATGGGCA GCCGGAGAAC AACTACAAGA CCACACCTCC

1251  CATGCTGGAC TCCGACGGCT CCTTCTTCCT CTACAGCAAG CTCACCGTGG

1301  ACAAGAGCAG GTGGCAGCAG GGGAACGTCT TCTCATGCTC CGTGATGCAT

1351  GAGGCTCTGC ACAACCACTA CACGCAGAAG AGCCTCTCCC TGTCTCCGGG

1401  TAAATGATAG
```

```
SEQ ID NO. 6
6.34.2-mod Predicted Heavy Chain Amino Acid Sequence
    1   mefqlswvfl vallrgvqcQ VQLVESGGGV VQPGRSLRLS CAASGFTFSS

51   YGMHWVRQAP GKGLEWVAVI SNDGNNKYYA DSVKGRFTIS RDNSKNTLYL

101   QMNSLRAEDT AVYYCARDST AITYYYGMD  VWGQGTTVTV SSASTKGPSV

151   FPLAPCSRST SESTAALGCL VKDYFPEPVT VSWNSGALTS GVHTFPAVLQ

201   SSGLYSLSSV VTVPSSNFGT QTYTCNVDHK PSNTKVDKTV ERKCCVECPP

251   CPAPPVAGPS VFLFPPKPKD TLMISRTPEV TCVVVDVSHE DPEVQFNWYV

301   DGVEVHNAKT KPREEQFNST FRVVSVLTVV HQDWLNGKEY KCKVSNKGLP

351   APIEKTISKT KGQPREPQVY TLPPSREEMT KNQVSLTCLV KGFYPSDIAV

401   EWESNGQPEN NYKTTPPMLD SDGSFFLYSK LTVDKSRWQQ GNVFSCSVMH

451   EALHNHYTQK SLSLSPGK

SEQ ID NO: 7
6.34.2-mod_SSQ Kappa Light Chain Nucleotide Sequence
    1   atggacatga gggtccccgc tcagctcctg gggctcctgc tactctggct 51   ccgaggtgcc agatgtGACA TCCAGATGAC CCAGTCTCCA TCCTCCCTGT

101   CTGCATCTGT CGGAGACAGA GTCACCATCA CTTGCCGGGC AAGTCAGAGT

151   ATTAGTAGCT ATTTAAATTG GTATCAGCAG AAACCAGGGA AAGCCCCTAA

201   GCTCCTGATC TATGCTGCAT CCAGTTTGAG TCAGGGGGTC CCATCACGGT

251   TCAGTGGTAG TGGATCTGGG ACAGATTTCA CTCTCACCAT CAGTTCTCTG

301   CAACCTGAGG ATTTTGCAAC TTACTACTGT CACCAGAGTT ACAGTCTCCC

351   ATTCACTTTC GGCCCTGGGA CCAAAGTGGA TATCAAACGA ACTGTGGCTG

401   CACCATCTGT CTTCATCTTC CCGCCATCTG ATGAGCAGTT GAAATCTGGA

451   ACTGCCTCTG TTGTGTGCCT GCTGAATAAC TTCTATCCCA GAGAGGCCAA

501   AGTACAGTGG AAGGTGGATA ACGCCCTCCA ATCGGGTAAC TCCCAGGAGA

551   GTGTCACAGA GCAGGACAGC AAGGACAGCA CCTACAGCCT CAGCAGCACC

601   CTGACGCTGA GCAAAGCAGA CTACGAGAAA CACAAAGTCT ACGCCTGCGA

651   AGTCACCCAT CAGGGCCTGA GCTCGCCCGT CACAAAGAGC TTCAACAGGG

701   GAGAGTGTTA GTGA

SEQ ID NO: 8
6.34.2-mod_SSQ Predicted Kappa Light Chain Protein Sequence
    1   mdmrvpaqll qlllwlrga rcDIQMTQSP SSLSASVGDR VTITCRASQS

51   ISSYLNWYQQ KPGKAPKLLI YAASSLSQGV PSRFSGSGSG TDFTLTISSL

101   QPEDFATYYC HQSYSLPFTF GPGTKVDIKR TVAAPSVFIF PPSDEQLKSG

151   TASVVCLLNN FYPREAKVQW KVDNALQSGN SQESVTEQDS KDSTYSLSST

201   LTLSKADYEK HKVYACEVTH QGLSSPVTKS FNRGEC

SEQ ID NO: 9
6.34.2-mod_QT Kappa Light Chain Nucleotide Sequence
    1   atggacatga gggtccccgc tcagctcctg gggctcctgc tactctggct 51   ccgaggtgcc agatgtGACA TCCAGATGAC CCAGTCTCCA TCCTCCCTGT

101   CTGCATCTGT CGGAGACAGA GTCACCATCA CTTGCCGGGC AAGTCAGAGT

151   ATTAGTAGCT ATTTAAATTG GTATCAGCAG AAACCAGGGA AAGCCCCTAA

201   GCTCCTGATC TATGCTGCAT CCGGTTTGAA GCGTGGGGTC CCATCACGGT

251   TCAGTGGTAG TGGATCTGGG ACAGATTTCA CTCTCACCAT CAGTTCTCTG

301   CAACCTGAGG ATTTTGCAAC TTACTACTGT CAGCAGAGTT ACAGTACTCC
```

```
351 ATTCACTTTC GGCCCTGGGA CCAAAGTGGA TATCAAACGA ACTGTGGCTG

401 CACCATCTGT CTTCATCTTC CCGCCATCTG ATGAGCAGTT GAAATCTGGA

451 ACTGCCTCTG TTGTGTGCCT GCTGAATAAC TTCTATCCCA GAGAGGCCAA

501 AGTACAGTGG AAGGTGGATA ACGCCCTCCA ATCGGGTAAC TCCCAGGAGA

551 GTGTCACAGA GCAGGACAGC AAGGACAGCA CCTACAGCCT CAGCAGCACC

601 CTGACGCTGA GCAAAGCAGA CTACGAGAAA CACAAAGTCT ACGCCTGCGA

651 AGTCACCCAT CAGGGCCTGA GCTCGCCCGT CACAAAGAGC TTCAACAGGG

701 GAGAGTGTTA GTGA

SEQ ID NO: 10
6.34.2-mod_QT Predicted Kappa Light Chain Protein Sequence
  1 mdmrvpaqll qlLlLwLrga rcDIQMTQSP SSLSASVGDR VTITCRASQS

51 ISSYLNWYQQ KPGKAPKLLI YAASGLKRGV PSRFSGSGSG TDFTLTISSL

101 QPEDFATYYC QQSYSTPFTF GPGTKVDIKR TVAAPSVFIF PPSDEQLKSG

151 TASVVCLLNN FYPREAKVQW KVDNALQSGN SQESVTEQDS KDSTYSLSST

201 LTLSKADYEK HKVYACEVTH QGLSSPVTKS FNRGEC

SEQ ID NO: 11
6.34.2-mod_SSQ,QT Kappa Light Chain Nucleotide Sequence
  1 atggacatga gggtccccgc tcagctcctg gggctcctgc tactctggct 51 ccgaggtgcc agatgtGACA TCCAGATGAC CCAGTCTCCA TCCTCCCTGT

101 CTGCATCTGT CGGAGACAGA GTCACCATCA CTTGCCGGGC AAGTCAGAGT

151 ATTAGTAGCT ATTTAAATTG GTATCAGCAG AAACCAGGGA AAGCCCCTAA

201 GCTCCTGATC TATGCTGCAT CCAGTTTGAG TCAGGGGGTC CCATCACGGT

251 TCAGTGGTAG TGGATCTGGG ACAGATTTCA CTCTCACCAT CAGTTCTCTG

301 CAACCTGAGG ATTTTGCAAC TTACTACTGT CAGCAGAGTT ACAGTACTCC

351 ATTCACTTTC GGCCCTGGGA CCAAAGTGGA TATCAAACGA ACTGTGGCTG

401 CACCATCTGT CTTCATCTTC CCGCCATCTG ATGAGCAGTT GAAATCTGGA

451 ACTGCCTCTG TTGTGTGCCT GCTGAATAAC TTCTATCCCA GAGAGGCCAA

501 AGTACAGTGG AAGGTGGATA ACGCCCTCCA ATCGGGTAAC TCCCAGGAGA

551 GTGTCACAGA GCAGGACAGC AAGGACAGCA CCTACAGCCT CAGCAGCACC

601 CTGACGCTGA GCAAAGCAGA CTACGAGAAA CACAAAGTCT ACGCCTGCGA

651 AGTCACCCAT CAGGGCCTGA GCTCGCCCGT CACAAAGAGC TTCAACAGGG

701 GAGAGTGTTA GTGA

SEQ ID NO: 12
6.34.2-mod_SSQ, QT Predicted Kappa Light Chain Protein
Sequence
  1 mdmrvpaqll qllllwlrga rcDIQMTQSP SSLSASVGDR VTITCRASQS

51 ISSYLNWYQQ KPGKAPKLLI YAASSLSQGV PSRFSGSGSG TDFTLTISSL

101 QPEDFATYYC QQSYSTPFTF GPGTKVDIKR TVAAPSVFIF PPSDEQLKSG

151 TASVVCLLNN FYPREAKVQW KVDNALQSGN SQESVTEQDS KDSTYSLSST

201 LTLSKADYEK HKVYACEVTH QGLSSPVTKS FNRGEC

SEQ ID NO: 13
6.67.1-mod Heavy Chain Nucleotide Sequence
  1 atgaaacacc tgtggttctt cctcctgctg gtggcagctc ccagatgggt 51 cctgtccCAG GTGCAGCTGC AGGAGTCGGG CCCAGGACTG GTGAAGCCTT

101 CGGAGACCCT GTCCCTCACC TGCACTGTCT CTGGTGACTC CATCAGTAGT
```

```
151   AACTATTGGA GCTGGATCCG GCAGCCCGCC GGGAAGGGAC TGGAGTGGAT
201   TGGGCGTATC TATACCAGTG GGGGCACCAA CTCCAACCCC TCCCTCAGGG
251   GTCGAGTCAC CATGTCAGTA GACACGTCCA AGAACCAGTT CTCTCTGAAA
301   CTGAGTTCTG TGACCGCCGC GGACACGGCC GTGTATTACT GTGCGAGAGA
351   TCGTATTACT ATAATTCGGG GACTTATTCC ATCCTTCTTT GACTACTGGG
401   GCCAGGGAAC CCTGGTCACC GTCTCCTCAG CTTCCACCAA GGGCCCATCC
451   GTCTTCCCCC TGGCGCCCTG CTCTAGAAGC ACCTCCGAGA GCACAGCGGC
501   CCTGGGCTGC CTGGTCAAGG ACTACTTCCC CGAACCGGTG ACGGTGTCGT
551   GGAACTCAGG CGCTCTGACC AGCGGCGTGC ACACCTTCCC AGCTGTCCTA
601   CAGTCCTCAG GACTCTACTC CCTCAGCAGC GTGGTGACCG TGCCCTCCAG
651   CAACTTCGGC ACCCAGACCT ACACCTGCAA CGTAGATCAC AAGCCCAGCA
701   ACACCAAGGT GGACAAGACA GTTGAGCGCA AATGTTGTGT CGAGTGCCCA
751   CCGTGCCCAG CACCACCTGT GGCAGGACCG TCAGTCTTCC TCTTCCCCCC
801   AAAACCCAAG GACACCCTCA TGATCTCCCG GACCCCTGAG GTCACGTGCG
851   TGGTGGTGGA CGTGAGCCAC GAAGACCCCG AGGTCCAGTT CAACTGGTAC
901   GTGGACGGCG TGGAGGTGCA TAATGCCAAG ACAAAGCCAC GGGAGGAGCA
951   GTTCAACAGC ACGTTCCGTG TGGTCAGCGT CCTCACCGTT GTGCACCAGG
1001  ACTGGCTGAA CGGCAAGGAG TACAAGTGCA AGGTCTCCAA CAAAGGCCTC
1051  CCAGCCCCCA TCGAGAAAAC CATCTCCAAA ACCAAAGGGC AGCCCCGAGA
1101  ACCACAGGTG TACACCCTGC CCCCATCCCG GGAGGAGATG ACCAAGAACC
1151  AGGTCAGCCT GACCTGCCTG GTCAAAGGCT TCTACCCCAG CGACATCGCC
1201  GTGGAGTGGG AGAGCAATGG GCAGCCGGAG AACAACTACA GACCACACC
1251  TCCCATGCTG GACTCCGACG GCTCCTTCTT CCTCTACAGC AAGCTCACCG
1301  TGGACAAGAG CAGGTGGCAG CAGGGGAACG TCTTCTCATG CTCCGTGATG
1351  CATGAGGCTC TGCACAACCA CTACACGCAG AAGAGCCTCT CCCTGTCTCC
1401  GGGTAAATGA TAG

SEQ ID NO. 14
6.67.1-mod Predicted Heavy Chain Amino Acid Sequence
   1   mkhlwfflll vaaprwvlsQ VQLQESGPGL VKPSETLSLT CTVSGDSISS
  51   NYWSWIRQPA GKGLEWIGRI YTSGGTNSNP SLRGRVTMSV DTSKNQFSLK
 101   LSSVTAADTA VYYCARDRIT IIRGLIPSFF DYWGQGTLVT VSSASTKGPS
 151   VFPLAPCSRS TSESTAALGC LVKDYFPEPV TVSWNSGALT SGVHTFPAVL
 201   QSSGLYSLSS VVTVPSSNFG TQTYTCNVDH KPSNTKVDKT VERKCCVECP
 251   PCPAPPVAGP SVFLFPPKPK DTLMISRTPE VTCVVVDVSH EDPEVQFNWY
 301   VDGVEVHNAK TKPREEQFNS TFRVVSVLTV VHQDWLNGKE YKCKVSNKGL
 351   PAPIEKTISK TKGQPREPQV YTLPPSREEM TKNQVSLTCL VKGFYPSDIA
 401   VEWESNGQPE NNYKTTPPML DSDGSFFLYS KLTVDKSRWQ QGNVFSCSVM
 451   HEALHNHYTQ KSLSLSPGK SEQ ID NO. 15
6.67.1-mod_Y Kappa Light Chain Nucleotide Sequence
   1   atgqtgttgc agacccagqt cttcatttct ctqttqctct qqatctctqq
  51   tgcctacggg GACATCGTGA TGACCCAGTC TCCAGACTCC CTGGCTGTGT
 101   CTCTGGGCGA GAGGGCCACC ATCAACTGCA AGTCCAGCCA GAGTGTTTTA
```

```
151   TACAGCTCCA ACAATAAGAA CTACTTAGCT TGGTACCAAC AGAAACCAGG

201   ACAGCCTCCT AAATTGCTCA TTTACTGGGC ATCTATACGG AATATGGGG

251   TCCCTGACCG ATTCAGTGGC AGCGGGTCTG GGACAGATTT CACTCTCACC

301   ATCAGCAGCC TGCAGGCTGA AGATGTGGCA GTTTATTATT GTCAACAATA

351   TTATAGTATT CCTCCCCTCA CTTTCGGCGG AGGGACCAAG GTGGAGATCA

401   AACGAACTGT GGCTGCACCA TCTGTCTTCA TCTTCCCGCC ATCTGATGAG

451   CAGTTGAAAT CTGGAACTGC CTCTGTTGTG TGCCTGCTGA ATAACTTCTA

501   TCCCAGAGAG GCCAAAGTAC AGTGGAAGGT GGATAACGCC CTCCAATCGG

551   GTAACTCCCA GGAGAGTGTC ACAGAGCAGG ACAGCAAGGA CAGCACCTAC

601   AGCCTCAGCA GCACCCTGAC GCTGAGCAAA GCAGACTACG AGAAACACAA

651   AGTCTACGCC TGCGAAGTCA CCCATCAGGG CCTGAGCTCG CCCGTCACAA

701   AGAGCTTCAA CAGGGGAGAG TGTTAGTGA

SEQ ID NO: 16
6.67.1-mod_Y Predicted Kappa Light Chain Amino Acid Sequence
  1   mvlqtqvfis lllwlsgayg DIVMTQSPDS LAVSLGERAT INCKSSQSVL

51   YSSNNKNYLA WYQQKPGQPP KLLIYWASIR EYGVPDRFSG SGSGTDFTLT

101   ISSLQAEDVA VYYCQQYYSI PPLTFGGGTK VEIKRTVAAP SVFIFPPSDE

151   QLKSGTASVV CLLNNFYPRE AKVQWKVDNA LQSGNSQESV TEQDSKDSTY

201   SLSSTLTLSK ADYEKHKVYA CEVTHQGLSS PVTKSFNRGE C

SEQ ID NO: 17
6.67.1-mod_TΔP Kappa Light Chain Nucleotide Sequence
  1   atggtgttgc agacccaggt cttcatttct ctgttgctct ggatctctgg 51   tgcctacggg GACATCGTGA TGACCCAGTC TCCAGACTCC CTGGCTGTGT

101   CTCTGGGCGA GAGGGCCACC ATCAACTGCA AGTCCAGCCA GAGTGTTTTA

151   TACAGCTCCA ACAATAAGAA CTACTTAGCT TGGTACCAAC AGAAACCAGG

201   ACAGCCTCCT AAATTGCTCA TTTACTGGGC ATCTATACGG AATATGGGG

251   TCCCTGACCG ATTCAGTGGC AGCGGGTCTG GGACAGATTT CACTCTCACC

301   ATCAGCAGCC TGCAGGCTGA AGATGTGGCA GTTTATTTCT GTCAACAATA

351   TTATAGTACC CCT---CTCA CTTTCGGCGG AGGGACCAAG GTGGAGATCA

401   AACGAACTGT GGCTGCACCA TCTGTCTTCA TCTTCCCGCC ATCTGATGAG

451   CAGTTGAAAT CTGGAACTGC CTCTGTTGTG TGCCTGCTGA ATAACTTCTA

501   TCCCAGAGAG GCCAAAGTAC AGTGGAAGGT GGATAACGCC CTCCAATCGG

551   GTAACTCCCA GGAGAGTGTC ACAGAGCAGG ACAGCAAGGA CAGCACCTAC

601   AGCCTCAGCA GCACCCTGAC GCTGAGCAAA GCAGACTACG AGAAACACAA

651   AGTCTACGCC TGCGAAGTCA CCCATCAGGG CCTGAGCTCG CCCGTCACAA

701   AGAGCTTCAA CAGGGGAGAG TGTTAGTGA

SEQ ID NO: 18
6.67.1-mod_TΔP Predicted Kappa Light Chain Amino Acid
Sequence
  1   mvlqtqvfis lllwlsgayg DIVMTQSPDS LAVSLGERAT INCKSSQSVL

51   YSSNNKNYLA WYQQKPGQPP KLLIYWASIR EYGVPDRFSG SGSGTDFTLT

101   ISSLQAEDVA VYFCQQYYST P-LTFGGGTK VEIKRTVAAP SVFIFPPSDE

151   QLKSGTASVV CLLNNFYPRE AKVQWKVDNA LQSGNSQESV TEQDSKDSTY

201   SLSSTLTLSK ADYEKHKVYA CEVTHQGLSS PVTKSFNRGE C
```

-continued

SEQ ID NO: 19
6.67.1-mod_Y, TΔP Kappa Light Chain Nucleotide Sequence
  1   atggtgttgc agacccaggt cttcatttct ctgttgctct ggatctctgg 51   tgcctacggg GACATCGTGA TGACCCAGTC TCCAGACTCC CTGGCTGTGT

101   CTCTGGGCGA GAGGGCCACC ATCAACTGCA AGTCCAGCCA GAGTGTTTTA

151   TACAGCTCCA ACAATAAGAA CTACTTAGCT TGGTACCAAC AGAAACCAGG

201   ACAGCCTCCT AAATTGCTCA TTTACTGGGC ATCTATACGG AATATGGGG

251   TCCCTGACCG ATTCAGTGGC AGCGGGTCTG GGACAGATTT CACTCTCACC

301   ATCAGCAGCC TGCAGGCTGA AGATGTGGCA GTTTATTATT GTCAACAATA

351   TTATAGTACC CCT---CTCA CTTTCGGCGG AGGGACCAAG GTGGAGATCA

401   AACGAACTGT GGCTGCACCA TCTGTCTTCA TCTTCCCGCC ATCTGATGAG

451   CAGTTGAAAT CTGGAACTGC CTCTGTTGTG TGCCTGCTGA ATAACTTCTA

501   TCCCAGAGAG GCCAAAGTAC AGTGGAAGGT GGATAACGCC CTCCAATCGG

551   GTAACTCCCA GGAGAGTGTC ACAGAGCAGG ACAGCAAGGA CAGCACCTAC

601   AGCCTCAGCA GCACCCTGAC GCTGAGCAAA GCAGACTACG AGAAACACAA

651   AGTCTACGCC TGCGAAGTCA CCCATCAGGG CCTGAGCTCG CCCGTCACAA

701   AGAGCTTCAA CAGGGGAGAG TGTTAGTGA

SEQ ID NO: 20
6.67.1-mod_Y, TΔP Predicted Kappa Light Chain Amino Acid
Sequence
  1   mvlqtqvfis lllwlsgayg DIVMTQSPDS LAVSLGERAT INCKSSQSVL

51   YSSNNKNYLA WYQQKPGQPP KLLIYWASIR EYGVPDRFSG SGSGTDFTLT

101   ISSLQAEDVA VYYCQQYYST P-LTFGGGTK VEIKRTVAAP SVFIFPPSDE

151   QLKSGTASVV CLLNNFYPRE AKVQWKVDNA LQSGNSQESV TEQDSKDSTY

201   SLSSTLTLSK ADYEKHKVYA CEVTHQGLSS PVTKSFNRGE C

SEQ ID NO: 21
6.77.1-modΔS Heavy Chain Nucleotide Sequence
  1   atggaactgg ggctccgctg ggttttcctt gttgctattt tagaaggtgt 51   ccagtgtGAG GTGCAGCTGG TGGAGTCTGG GGGAGGCCTG GTCAAGCCTG

101   GGGGGTCCCT GAGACTCTCC TGTGCAGCCT CTGGATTCAC CTTCAGTAGC

151   TATAGCATGA ACTGGGTCCG CCAGGCTCCA GGGAAGGGGC TGGAGTGGGT

201   CTCATCCATT AGTAGTAGTA GTAGTTACAT ATACTACGCA GACTCAGTGA

251   AGGGCCGATT CACCATCTCC AGAGACAACG CCAAGAACTC ACTGTATCTG

301   CAAATGAACA GCCTGAGAGC CGAGGACACG GCTGTGTATT ACTGTGCGAG

351   AGATGGGTAT AGCAGTGGCT GG---TACTA CTACTACTAC GGTATGGACG

401   TCTGGGGCCA AGGGACCACG GTCACCGTCT CCTCAGCTTC CACCAAGGGC

451   CCATCCGTCT TCCCCCTGGC GCCCTGCTCT AGAAGCACCT CCGAGAGCAC

501   AGCGGCCCTG GGCTGCCTGG TCAAGGACTA CTTCCCCGAA CCGGTGACGG

551   TGTCGTGGAA CTCAGGCGCT CTGACCAGCG GCGTGCACAC CTTCCCAGCT

601   GTCCTACAGT CCTCAGGACT CTACTCCCTC AGCAGCGTGG TGACCGTGCC

651   CTCCAGCAAC TTCGGCACCC AGACCTACAC CTGCAACGTA GATCACAAGC

701   CCAGCAACAC CAAGGTGGAC AAGACAGTTG AGCGCAAATG TTGTGTCGAG

751   TGCCCACCGT GCCCAGCACC ACCTGTGGCA GGACCGTCAG TCTTCCTCTT

801   CCCCCCAAAA CCCAAGGACA CCCTCATGAT CTCCCGGACC CCTGAGGTCA

```
 851   CGTGCGTGGT GGTGGACGTG AGCCACGAAG ACCCCGAGGT CCAGTTCAAC

901   TGGTACGTGG ACGGCGTGGA GGTGCATAAT GCCAAGACAA AGCCACGGGA

951   GGAGCAGTTC AACAGCACGT TCCGTGTGGT CAGCGTCCTC ACCGTTGTGC

1001   ACCAGGACTG GCTGAACGGC AAGGAGTACA AGTGCAAGGT CTCCAACAAA

1051   GGCCTCCCAG CCCCCATCGA GAAAACCATC TCCAAAACCA AAGGGCAGCC

1101   CCGAGAACCA CAGGTGTACA CCCTGCCCCC ATCCCGGGAG GAGATGACCA

1151   AGAACCAGGT CAGCCTGACC TGCCTGGTCA AAGGCTTCTA CCCCAGCGAC

1201   ATCGCCGTGG AGTGGGAGAG CAATGGGCAG CCGGAGAACA ACTACAAGAC

1251   CACACCTCCC ATGCTGGACT CCGACGGCTC CTTCTTCCTC TACAGCAAGC

1301   TCACCGTGGA CAAGAGCAGG TGGCAGCAGG GAACGTCTT CTCATGCTCC

1351   GTGATGCATG AGGCTCTGCA CAACCACTAC ACGCAGAAGA GCCTCTCCCT

1401   GTCTCCGGGT AAATGATAG

SEQ ID NO: 22
6.77.1-modΔS Predicted Heavy Chain Protein Sequence
   1   melglrwvfl vailegvqcE VQLVESGGGL VKPGGSLRLS CAASGFTFSS

51   YSMNWVRQAP GKGLEWVSSI SSSSSYIYYA DSVKGRFTIS RDNAKNSLYL

101   QMNSLRAEDT AVYYCARDGY SSGW-YYYYY GMDVWGQGTT VTVSSASTKG

151   PSVFPLAPCS RSTSESTAAL GCLVKDYFPE PVTVSWNSGA LTSGVHTFPA

201   VLQSSGLYSL SSVVTVPSSN FGTQTYTCNV DHKPSNTKVD KTVERKCCVE

251   CPPCPAPPVA GPSVFLFPPK PKDTLMISRT PEVTCVVVDV SHEDPEVQFN

301   WYVDGVEVHN AKTKPREEQF NSTFRVVSVL TVVHQDWLNG KEYKCKVSNK

351   GLPAPIEKTI SKTKGQPREP QVYTLPPSRE EMTKNQVSLT CLVKGFYPSD

401   IAVEWESNGQ PENNYKTTPP MLDSDGSFFL YSKLTVDKSR WQQGNVFSCS

451   VMHEALHNHY TQKSLSLSPG K

SEQ ID NO: 23
6.77.1-mod Kappa Light Chain Nucleotide Sequence
   1   atgaggctcc ctgctcagct cctggggctg ctaatgctct ggatacctgg 51   atccagtgca GATATTGTGA TGACCCAGAC TCCACTCTCT CTGTCCGTCA

101   CTCCTGGACA GCCGGCCTCC ATCTCCTGCA AGTCTAGTCA GAGCCTCCTG

151   CTTAGTGATG GAAAGACCTA TTTGAATTGG TACCTGCAGA AGCCCGGCCA

201   GCCTCCACAG CTCCTGATCT ATGAAGTTTC CAACCGGTTC TCTGGAGTGC

251   CAGACAGGTT CAGTGGCAGC GGGTCAGGGA CAGATTTCAC ACTGAAAATC

301   AGCCGGGTGG AGGCTGAGGA TGTTGGGGTT TATTACTGCA TGCAAAGTAT

351   ACAGCTTATG TGCAGTTTTG GCCAGGGGAC CAAGCTGGAG ATCAAACGAA

401   CTGTGGCTGC ACCATCTGTC TTCATCTTCC CGCCATCTGA TGAGCAGTTG

451   AAATCTGGAA CTGCCTCTGT TGTGTGCCTG CTGAATAACT TCTATCCCAG

501   AGAGGCCAAA GTACAGTGGA AGGTGGATAA CGCCCTCCAA TCGGGTAACT

551   CCCAGGAGAG TGTCACAGAG CAGGACAGCA AGGACAGCAC CTACAGCCTC

601   AGCAGCACCC TGACGCTGAG CAAAGCAGAC TACGAGAAAC ACAAAGTCTA

651   CGCCTGCGAA GTCACCCATC AGGGCCTGAG CTCGCCCGTC ACAAAGAGCT

701   TCAACAGGGG AGAGTGTTAG TGA
```

-continued

SEQ ID NO. 24
6.77.1-mod Predicted Kappa Light Chain Amino Acid Sequence
  1    mrlpaqllgl lmlwipgssa DIVMTQTPLS SVTPGQPAS ISCKSSQSLL

51    LSDGKTYLNW YLQKPGQPPQ LLIYEVSNRF SGVPDRFSGS GSGTDFTLKI

101    SRVEAEDVGV YSCMQSIQLM SSFGQGTKLE IKRTVAAPSV FIFPPSDEQL

151    KSGTASVVCL LNNFYPREAK VQWKVDNALQ SGNSQESVTE QDSKDSTYSL

201    SSTLTLSKAD YEKHKVYACE VTHQGLSSPV TKSFNRGEC

SEQ ID NO. 25
7.16.6 Heavy Chain Nucleotide Sequence
   1   atggactgga cctggagcat ccttttcttg gtggcagcag caacaggtgc 51   ccactccCAG GTTCAGCTGG TGCAGTCTGG AGCTGAGGTG AAGAAGCCTG

101   GGGCCTCAGT GAAGGTCTCC TGCAAGGCTT CTGGTTACAC CTTTACCAGC

151   TATGGTATCA ACTGGGTGCG ACAGGCCCCT GGACAAGGGC TTGAGTGGAT

201   GGGATGGATC AGCGTTTACA GTGGTAACAC AAACTATGCA CAGAAGGTCC

251   AGGGCAGAGT CACCATGACC GCAGACACAT CCACGAGCAC AGCCTACATG

301   GACCTGAGGA GCCTGAGATC TGACGACACG GCCGTGTATT ACTGTGCGAG

351   AGAGGGTAGC AGCTCGTCCG GAGACTACTA TTACGGTATG GACGTCTGGG

401   GCCAAGGGAC CACGGTCACC GTCTCCTCAG CCTCCACCAA GGGCCCATCG

451   GTCTTCCCCC TGGCGCCCTG CTCCAGGAGC ACCTCCGAGA GCACAGCGGC

501   CCTGGGCTGC CTGGTCAAGG ACTACTTCCC CGAACCGGTG ACGGTGTCGT

551   GGAACTCAGG CGCTCTGACC AGCGGCGTGC ACACCTTCCC AGCTGTCCTA

601   CAGTCCTCAG GACTCTACTC CCTCAGCAGC GTGGTGACCG TGCCCTCCAG

651   CAACTTCGGC ACCCAGACCT ACACCTGCAA CGTAGATCAC AAGCCCAGCA

701   ACACCAAGGT GGACAAGACA GTTGAGCGCA AATGTTGTGT CGAGTGCCCA

751   CCGTGCCCAG CACCACCTGT GGCAGGACCG TCAGTCTTCC TCTTCCCCCC

801   AAAACCCAAG GACACCCTCA TGATCTCCCG GACCCCTGAG GTCACGTGCG

851   TGGTGGTGGA CGTGAGCCAC GAAGACCCCG AGGTCCAGTT CAACTGGTAC

901   GTGGACGGCG TGGAGGTGCA TAATGCCAAG ACAAAGCCAC GGGAGGAGCA

951   GTTCAACAGC ACGTTCCGTG TGGTCAGCGT CCTCACCGTT GTGCACCAGG

1001   ACTGGCTGAA CGGCAAGGAG TACAAGTGCA AGGTCTCCAA CAAAGGCCTC

1051   CCAGCCCCCA TCGAGAAAAC CATCTCCAAA ACCAAAGGGC AGCCCCGAGA

1101   ACCACAGGTG TACACCCTGC CCCCATCCCG GGAGGAGATG ACCAAGAACC

1151   AGGTCAGCCT GACCTGCCTG GTCAAAGGCT TCTACCCCAG CGACATCGCC

1201   GTGGAGTGGG AGAGCAATGG GCAGCCGGAG AACAACTACA AGACCACACC

1251   TCCCATGCTG GACTCCGACG GCTCCTTCTT CCTCTACAGC AAGCTCACCG

1301   TGGACAAGAG CAGGTGGCAG CAGGGGAACG TCTTCTCATG CTCCGTGATG

1351   CATGAGGCTC TGCACAACCA CTACACGCAG AAGAGCCTCT CCCTGTCTCC

1401   GGGTAAATGA

SEQ ID NO. 26
7.16.6 Predicted Heavy Chain Protein Sequence
  1    mdwtwsilfl vaaatgahsQ VQLVQSGAEV KKPGASVKVS CKASGYTFTS

51    YGINWVRQAP GQGLEWMGWI SVYSGNTNYA QKVQGRVTMT ADTSTSTAYM

101    DLRSLRSDDT AVYYCAREGS SSSGDYYYGM DVWGQGTTVT VSSASTKGPS

151    VFPLAPCSRS TSESTAALGC LVKDYFPEPV TVSWNSGALT SGVHTFPAVL

```
201    QSSGLYSLSS VVTVPSSNFG TQTYTCNVDH KPSNTKVDKT VERKCCVECP

251    PCPAPPVAGP SVFLFPPKPK DTLMISRTPE VTCVVVDVSH EDPEVQFNWY

301    VDGVEVHNAK TKPREEQFNS TFRVVSVLTV VHQDWLNGKE YKCKVSNKGL

351    PAPIEKTISK TKGQPREPQV YTLPPSREEM TKNQVSLTCL VKGFYPSDIA

401    VEWESNGQPE NNYKTTPPML DSDGSFFLYS KLTVDKSRWQ QGNVFSCSVM

451    HEALHNHYTQ KSLSLSPGK

SEQ ID NO: 27
7.16.6_L Heavy Chain Nucleotide Sequence
  1    atggactgga cctggagcat cctttcttg gtggcagcag caacaggtgc 51    ccactccCAG GTTCAGCTGG TGCAGTCTGG AGCTGAGGTG AAGAAGCCTG

101    GGGCCTCAGT GAAGGTCTCC TGCAAGGCTT CTGGTTACAC CTTTACCAGC

151    TATGGTATCA ACTGGGTGCG ACAGGCCCCT GGACAAGGGC TTGAGTGGAT

201    GGGATGGATC AGCGTTTACA GTGGTAACAC AAACTATGCA CAGAAGCTTC

251    AGGGCAGAGT CACCATGACC GCAGACACAT CCACGAGCAC AGCCTACATG

301    GACCTGAGGA GCCTGAGATC TGACGACACG GCCGTGTATT ACTGTGCGAG

351    AGAGGGTAGC AGCTCGTCCG GAGACTACTA TTACGGTATG GACGTCTGGG

401    GCCAAGGGAC CACGGTCACC GTCTCCTCAG CCTCCACCAA GGGCCCATCG

451    GTCTTCCCCC TGGCGCCCTG CTCCAGGAGC ACCTCCGAGA GCACAGCGGC

501    CCTGGGCTGC CTGGTCAAGG ACTACTTCCC CGAACCGGTG ACGGTGTCGT

551    GGAACTCAGG CGCTCTGACC AGCGGCGTGC ACACCTTCCC AGCTGTCCTA

601    CAGTCCTCAG GACTCTACTC CCTCAGCAGC GTGGTGACCG TGCCCTCCAG

651    CAACTTCGGC ACCCAGACCT ACACCTGCAA CGTAGATCAC AAGCCCAGCA

701    ACACCAAGGT GGACAAGACA GTTGAGCGCA ATGTTGTGT CGAGTGCCCA

751    CCGTGCCCAG CACCACCTGT GGCAGGACCG TCAGTCTTCC TCTTCCCCCC

801    AAAACCCAAG GACACCCTCA TGATCTCCCG GACCCCTGAG GTCACGTGCG

851    TGGTGGTGGA CGTGAGCCAC GAAGACCCCG AGGTCCAGTT CAACTGGTAC

901    GTGGACGGCG TGGAGGTGCA TAATGCCAAG ACAAAGCCAC GGGAGGAGCA

951    GTTCAACAGC ACGTTCCGTG TGGTCAGCGT CCTCACCGTT GTGCACCAGG

1001    ACTGGCTGAA CGGCAAGGAG TACAAGTGCA AGGTCTCCAA CAAAGGCCTC

1051    CCAGCCCCCA TCGAGAAAAC CATCTCCAAA ACCAAAGGGC AGCCCCGAGA

1101    ACCACAGGTG TACACCCTGC CCCCATCCCG GGAGGAGATG ACCAAGAACC

1151    AGGTCAGCCT GACCTGCCTG GTCAAAGGCT TCTACCCCAG CGACATCGCC

1201    GTGGAGTGGG AGAGCAATGG GCAGCCGGAG AACAACTACA AGACCACACC

1251    TCCCATGCTG GACTCCGACG GCTCCTTCTT CCTCTACAGC AAGCTCACCG

1301    TGGACAAGAG CAGGTGGCAG CAGGGGAACG TCTTCTCATG CTCCGTGATG

1352    CATGAGGCTC TGCACAACCA CTACACGCAG AAGAGCCTCT CCCTGTCTCC

1401    GGGTAAATGA

SEQ ID NO. 28
7.16.6_L Predicted Heavy Chain Protein Sequence
  1    mdwtwsilfl vaaatgahsQ VQLVQSGAEV KKPGASVKVS CKASGYTFTS

51    YGINWVRQAP GQGLEWMGWI SVYSGNTNYA QKLQGRVTMT ADTSTSTAYM

101    DLRSLRSDDT AVYYCAREGS SSGDYYYGM DVWGQGTTVT VSSASTKGPS

151    VFPLAPCSRS TSESTAALGC LVKDYFPEPV TVSWNSGALT SGVHTFPAVL
```

```
201  QSSGLYSLSS VVTVPSSNFG TQTYTCNVDH KPSNTKVDKT VERKCCVECP

251  PCPAPPVAGP SVFLFPPKPK DTLMISRTPE VTCVVVDVSH EDPEVQFNWY

301  VDGVEVHNAK TKPREEQFNS TFRVVSVLTV VHQDWLNGKE YKCKVSNKGL

351  PAPIEKTISK TKGQPREPQV YTLPPSREEM TKNQVSLTCL VKGFYPSDIA

401  VEWESNGQPE NNYKTTPPML DSDGSFFLYS KLTVDKSRWQ QGNVFSCSVM

452  HEALHNHYTQ KSLSLSPGK
```

SEQ ID NO: 29
7.16.6_V Kappa Light Chain Nucleotide Sequence
```
  1  atgaggctcc ctgctcagct cctggggctg ctaatgctct ggataccctgg 51  atccagtgca GATATTGTGA TGACCCAGAC TCCACTCTCT CTGTCCGTCA

101  CCCCTGGACA GCCGGCCTCC ATCTCCTGCA AGTCTAGTCA GAGCCTCCTG

151  CATACTGATG GAACGACCTA TTTGTATTGG TACCTGCAGA AGCCAGGCCA

201  GCCTCCACAG CTCCTGATCT ATGAAGTTTC CAACCGGTTC TCTGGAGTGC

251  CAGATAGGTT CAGTGGCAGC GGGTCAGGGA CAGATTTCAC ACTGAAAATC

301  AGCCGGGTGG AGGCTGAGGA TGTTGGGGTT TATTACTGCA TGCAAAATAT

351  ACAGCTTCCG TGGACGTTCG GCCAAGGGAC CAAGGTGGAA ATCAAACGAA

401  CTGTGGCTGC ACCATCTGTC TTCATCTTCC CGCCATCTGA TGAGCAGTTG

451  AAATCTGGAA CTGCCTCTGT TGTGTGCCTG CTGAATAACT TCTATCCCAG

501  AGAGGCCAAA GTACAGTGGA AGGTGGATAA CGCCCTCCAA TCGGGTAACT

551  CCCAGGAGAG TGTCACAGAG CAGGACAGCA AGGACAGCAC CTACAGCCTC

601  AGCAGCACCC TGACGCTGAG CAAAGCAGAC TACGAGAAAC ACAAAGTCTA

651  CGCCTGCGAA GTCACCCATC AGGGCCTGAG CTCGCCCGTC ACAAAGAGCT

701  TCAACAGGGG AGAGTGTTAG TGA
```

SEQ ID NO: 30
7.16.6_V Predicted Kappa Light Chain Protein Sequence
```
  1  mrlpaqllql lmlwipqssa DIVMTQTPLS LSVTPGQPAS ISCKSSQSLL

51  HTDGTTYLYW YLQKPGQPPQ LLIYEVSNRF SGVPDRFSGS GSGTDFTLKI

101  SRVEAEDVGV YYCMQNIQLP WTFGQGTKVE IKRTVAAPSV FIFPPSDEQL

151  KSGTASVVCL LNNFYPREAK VQWKVDNALQ SGNSQESVTE QDSKDSTYSL

201  SSTLTLSKAD YEKHKVYACE VTHQGLSSPV TKSFNRGEC
```

SEQ ID NO: 31
7.16.6_S Kappa Light Chain Nucleotide Sequence
```
  1  atgaggctcc ctgctcagct cctggggctg ctaatgctct ggataccctgg 51  atccagtgca GATATTGTGA TGACCCAGAC TCCACTCTCT CTGTCCGTCA

101  CCCCTGGACA GCCGGCCTCC ATCTCCTGCA AGTCTAGTCA GAGCCTCCTG

151  CATACTGATG GAACGACCTA TTTGTATTGG TACCTGCAGA AGCCAGGCCA

201  GCCTCCACAG CTCCTGATCT ATGAAGTTTC CAACCGGTTC TCTGGAGTGC

251  CAGATAGGTT CAGTGGCAGC GGGTCAGGGA CAGATTTCAC ACTGAAAATC

301  AGCCGGGTGG AGGCTGAGGA TGTTGGGATT TATTACTGCA TGCAAAGTAT

351  ACAGCTTCCG TGGACGTTCG GCCAAGGGAC CAAGGTGGAA ATCAAACGAA

401  CTGTGGCTGC ACCATCTGTC TTCATCTTCC CGCCATCTGA TGAGCAGTTG

451  AAATCTGGAA CTGCCTCTGT TGTGTGCCTG CTGAATAACT TCTATCCCAG

501  AGAGGCCAAA GTACAGTGGA AGGTGGATAA CGCCCTCCAA TCGGGTAACT

551  CCCAGGAGAG TGTCACAGAG CAGGACAGCA AGGACAGCAC CTACAGCCTC
```

```
601 AGCAGCACCC TGACGCTGAG CAAAGCAGAC TACGAGAAAC ACAAAGTCTA

651 CGCCTGCGAA GTCACCCATC AGGGCCTGAG CTCGCCCGTC ACAAAGAGCT

701 TCAACAGGGG AGAGTGTTAG TGA
```

SEQ ID NO: 32
7.16.6_5 Predicted Kappa Light Chain Protein Sequence
```
  1 mrlpaqllgl lmlwipgssa DIVMTQTPLS LSVTPGQPAS ISCKSSQSLL

51 HTDGTTYLYW YLQKPGQPPQ LLIYEVSNRF SGVPDRFSGS GSGTDFTLKI

101 SRVEAEDVGI YYCMQSIQLP WTFGQGTKVE IKRTVAAPSV FIFPPSDEQL

151 KSGTASVVCL LNNFYPREAK VQWKVDNALQ SGNSQESVTE QDSKDSTYSL

201 SSTLTLSKAD YEKHKVYACE VTHQGLSSPV TKSFNRGEC
```

SEQ ID NO: 33
7.16.6_VS Kappa Light Chain Nucleotide Sequence
```
  1 atgaggctcc ctgctcagct cctggggctg ctaatgctct ggatacctgg 51 atccagtgca GATATTGTGA TGACCCAGAC TCCACTCTCT CTGTCCGTCA

101 CCCCTGGACA GCCGGCCTCC ATCTCCTGCA AGTCTAGTCA GAGCCTCCTG

151 CATACTGATG GAACGACCTA TTTGTATTGG TACCTGCAGA AGCCAGGCCA

201 GCCTCCACAG CTCCTGATCT ATGAAGTTTC CAACCGGTTC TCTGGAGTGC

251 CAGATAGGTT CAGTGGCAGC GGGTCAGGGA CAGATTTCAC ACTGAAAATC

301 AGCCGGGTGG AGGCTGAGGA TGTTGGGGTT TATTACTGCA TGCAAAGTAT

351 ACAGCTTCCG TGGACGTTCG GCCAAGGGAC CAAGGTGGAA ATCAAACGAA

401 CTGTGGCTGC ACCATCTGTC TTCATCTTCC CGCCATCTGA TGAGCAGTTG

451 AAATCTGGAA CTGCCTCTGT TGTGTGCCTG CTGAATAACT TCTATCCCAG

501 AGAGGCCAAA GTACAGTGGA AGGTGGATAA CGCCCTCCAA TCGGGTAACT

551 CCCAGGAGAG TGTCACAGAG CAGGACAGCA AGGACAGCAC CTACAGCCTC

601 AGCAGCACCC TGACGCTGAG CAAAGCAGAC TACGAGAAAC ACAAAGTCTA

651 CGCCTGCGAA GTCACCCATC AGGGCCTGAG CTCGCCCGTC ACAAAGAGCT

701 TCAACAGGGG AGAGTGTTAG TGA
```

SEQ ID NO: 34
7.16.6_VS Predicted Kappa Light Chain Protein Sequence
```
  1 mrlpaqllgl lmlwipgssa DIVMTQTPLS LSVTPGQPAS ISCKSSQSLL

51 HTDGTTYLYW YLQKPGQPPQ LLIYEVSNRF SGVPDRFSGS GSGTDFTLKI

101 SRVEAEDVGV YYCMQSIQLP WTFGQGTKVE IKRTVAAPSV FIFPPSDEQL

151 KSGTASVVCL LNNFYPREAK VQWKVDNALQ SGNSQESVTE QDSKDSTYSL

201 SSTLTLSKAD YEKHKVYACE VTHQGLSSPV TKSFNRGEC
```

SEQ ID NO: 35
9.8.2_ΔRGAYH, D Heavy Chain Nucleotide Sequence
```
  1 atggagtttg ggctgagctg ggttttcctc gttgctcttt taagaggtgt 51 ccagtgtCAG GTGCAGCTGG TGGAGTCTGG GGGAGGCGTG GTCCAGCCTG

101 GGAGGTCCCT GAGACTCTCC TGTGCAGCGT CTGGATTCAC CTTCAGTAGC

151 TATGGCATGC ACTGGGTCCG CCAGGCTCCA GGCAAGGGGC TGGAGTGGGT

201 GGCAGTTATA TGGTATGATG GAAGTAATAA ATACTATGCA GACTCCGTGA

251 AGGGCCGATT CACCATCTCC AGAGACAATT CCAAGAACAC GCTGTATCTG

301 CAAATGAACA GCCTGAGAGC CGAGGACACG GCTGTGTATT ACTGTGCG--

351 ---------- ---TTTGACT ACTGGGGCCA GGGAACCCTG GTCACCGTCT

401 CCTCAGCTTC CACCAAGGGC CCATCCGTCT TCCCCCTGGC GCCCTGCTCC
```

```
 451 AGGAGCACCT CCGAGAGCAC AGCCGCCCTG GGCTGCCTGG TCAAGGACTA
 501 CTTCCCCGAA CCGGTGACGG TGTCGTGGAA CTCAGGCGCC CTGACCAGCG
 551 GCGTGCACAC CTTCCCGGCT GTCCTACAGT CCTCAGGACT CTACTCCCTC
 601 AGCAGCGTGG TGACCGTGCC CTCCAGCAGC TTGGGCACGA AGACCTACAC
 651 CTGCAACGTA GATCACAAGC CCAGCAACAC CAAGGTGGAC AAGAGAGTTG
 701 AGTCCAAATA TGGTCCCCCA TGCCCATCAT GCCCAGCACC TGAGTTCCTG
 751 GGGGGACCAT CAGTCTTCCT GTTCCCCCCA AAACCCAAGG ACACTCTCAT
 801 GATCTCCCGG ACCCCTGAGG TCACGTGCGT GGTGGTGGAC GTGAGCCAGG
 851 AAGACCCCGA GGTCCAGTTC AACTGGTACG TGGATGGCGT GGAGGTGCAT
 901 AATGCCAAGA CAAAGCCGCG GGAGGAGCAG TTCAACAGCA CGTACCGTGT
 951 GGTCAGCGTC CTCACCGTCC TGCACCAGGA CTGGCTGAAC GGCAAGGAGT
1001 ACAAGTGCAA GGTCTCCAAC AAAGGCCTCC CGTCCTCCAT CGAGAAAACC
1051 ATCTCCAAAG CCAAAGGGCA GCCCCGAGAG CCACAGGTGT ACACCCTGCC
1101 CCCATCCCAG GAGGAGATGA CCAAGAACCA GGTCAGCCTG ACCTGCCTGG
1151 TCAAAGGCTT CTACCCCAGC GACATCGCCG TGGAGTGGGA GAGCAATGGG
1201 CAGCCGGAGA ACAACTACAA GACCACGCCT CCCGTGCTGG ACTCCGACGG
1251 CTCCTTCTTC CTCTACAGCA GGCTAACCGT GGACAAGAGC AGGTGGCAGG
1301 AGGGGAATGT CTTCTCATGC TCCGTGATGC ATGAGGCTCT GCACAACCAC
1351 TACACACAGA AGAGCCTCTC CCTGTCTCTG GGTAAATGA

SEQ ID NO: 36
9.8.2_ΔRGAYH, D Predicted Heavy Chain Protein Sequence
   1 mefqlswvfl vallrqvqcQ VQLVESGGGV VQPGRSLRLS CAASGFTFSS
  51 YGMHWVRQAP GKGLEWVAVI WYDGSNEYYA DSVKGRFTIS RDNSKNTLYL
 101 QMNSLRAEDT AVYYCA---- -FDYWGQGTL VTVSSASTKG PSVFPLAPCS
 151 RSTSESTAAL GCLVKDYFPE PVTVSWNSGA LTSGVHTFPA VLQSSGLYSL
 201 SSVVTVPSSS LGTKTYTCNV DHKPSNTKVD KRVESKYGPP CPSCPAPEFL
 251 GGPSVFLFPP KPKDTLMISR TPEVTCVVVD VSQEDPEVQF NWYVDGVEVH
 301 NAKTKPREEQ FNSTYRVVSV LTVLHQDWLN GKEYKCKVSN KGLPSSIEKT
 351 ISKAKGQPRE PQVYTLPPSQ EEMTKNQVSL TCLVKGFYPS DIAVEWESNG
 401 QPENNYKTTP PVLDSDGSFF LYSRLTVDKS RWQEGNVFSC SVMHEALHNH
 451 YTQKSLSLSL GK SEQ ID NO: 37
9.8.2-mod Kappa Light Chain Nucleotide Sequence
   1 atggacatga gggtccctgc tcagctcctg gggctcctgc tgctctggct
  51 ctcagtcgca ggtgccagat gtGACATCCA GATGACCCAG TCTCCATCCT
 101 CCCTGTCTGC ATCTGTAGGA GACAGAGTCA CCATCACTTG CCAGGCGAGT
 151 CAGGACATTA GCAACTATTT AAATTGGTAT CAGCAGAAAC CAGGGAAAGC
 201 CCCTAAGCTC CTGATCTACG ATGCATCCAA TTTGGAAACA GGGGTCCCAT
 251 CAAGGTTCAG TGGAAGTGGA TCTGGGACAG ATTTTACTTT CACCATCAGC
 301 AGCCTGCAGC CTGAAGATAT TGCAACATAT TCCTGTCAAC ACTCTGATAA
 351 TCTCATCACC TTCGGCCAGG GGACACGACT GGAGATTAAA CGAACTGTGG
 401 CTGCACCATC TGTCTTCATC TTCCCGCCAT CTGATGAGCA GTTGAAATCT
 451 GGAACTGCCT CTGTTGTGTG CCTGCTGAAT AACTTCTATC CCAGAGAGGC
```

```
501  CAAAGTACAG TGGAAGGTGG ATAACGCCCT CCAATCGGGT AACTCCCAGG

551  AGAGTGTCAC AGAGCAGGAC AGCAAGGACA GCACCTACAG CCTCAGCAGC

601  ACCCTGACGC TGAGCAAGGC AGACTACGAG AAACACAAAG TCTACGCCTG

651  CGAAGTCACC CATCAGGGCC TGAGCTCGCC CGTCACAAAG AGCTTCAACA

701  GGGGAGAGTG TTAGTGA
```

SEQ ID NO: 38
9.8.2-mod Predicted Kappa Light Chain Protein Sequence

```
  1  mdmrvpaqll qllllwlsva qarcDIQMTQ SPSSLSASVG DRVTITCQAS

51  QDISNYLNWY QQKPGKAPKL LIYDASNLET GVPSRFSGSG SGTDFTFTIS

101  SLQPEDIATY SCQHSDNLIT FGQGTRLEIK RTVAAPSVFI FPPSDEQLKS

151  GTASVVCLLN NFYPREAKVQ WKVDNALQSG NSQESVTEQD SKDSTYSLSS

201  TLTLSKADYE KHKVYACEVT HQGLSSPVTK SFNRGEC
```

The invention claimed is:

1. A monoclonal antibody, or antigen-binding portion thereof, that specifically binds MAdCAM comprising the variable region of the light chain of SEQ ID NO:30, 32 or 34 (7.16.6_V, 7.16.6_S, or 7.16.6_VS) without signal sequences and the variable region of the heavy chain of SEQ ID NO:26 (7.16.6) or SEQ ID NO:28 (7.16.6_L) without signal sequence.

2. A pharmaceutical composition comprising a therapeutically effective amount of a monoclonal antibody, or antigen-binding portion thereof, that specifically binds MAdCAM comprising the variable region of the light chain of SEQ ID NO:30, 32 or 34 (7.16.6_V, 7.16.6_S, or 7.16.6_VS) without signal sequences and the variable region of the heavy chain of SEQ ID NO:26 (7.16.6) or SEQ ID NO:28 (7.16.6_L) without signal sequence.

* * * * *

SEQUENCE LISTING

<160> NUMBER OF SEQ ID NOS: 92

<210> SEQ ID NO 1
<211> LENGTH: 1398
<212> TYPE: DNA
<213> ORGANISM: Homo sapiens

<400> SEQUENCE: 1

```
atggagtttg ggctgagctg ggttttcctc gttgctcttt taagaggtgt ccagtgtcag    60
gtgcagctgg tggagtctgg gggaggcgtg gtccagcctg gaggtccct  gagactctcc   120 tgtgcagcgt ctggattcac cttcagtagc gatggcatgc actgggtccg ccaggctcca   180
ggcaaggggc tggagtgggt ggcagtgata tggtatgatg aagtaataa  atattatgca   240 gactccgtga agggccgatt caccatctcc agagacaatt ccaagaacac gctgtatctg   300
caaatgaaca gcctgagagc cgaggacacg gctgtatatt actgtgcgag agatcccggc   360
tactattacg gtatggacgt ctggggccaa gggaccacgg tcaccgtctc ctcagcttcc   420
accaagggcc catccgtctt ccccctggcg ccctgctcta aagcacctc  cgagagcaca   480 gcggccctgg gctgcctggt caaggactac ttccccgaac cggtgacggt gtcgtggaac   540
tcaggcgctc tgaccagcgg cgtgcacacc ttcccagctg tcctacagtc ctcaggactc   600
tactccctca gcagcgtggt gaccgtgccc tccagcaact tcggcaccca gacctacacc   660
tgcaacgtag atcacaagcc cagcaacacc aaggtggaca agacagttga gcgcaaatgt   720
tgtgtcgagt gcccaccgtg cccagcacca cctgtgcag  accgtcagt  cttcctcttc   780 cccccaaaac ccaaggacac cctcatgatc tcccggaccc ctgaggtcac gtgcgtggtg   840
gtggacgtga gccacgaaga ccccgaggtc cagttcaact ggtacgtgga cggcgtggag   900
gtgcataatg ccaagacaaa gccacgggag gagcagttca acagcacgtt ccgtgtggtc   960
agcgtcctca ccgttgtgca ccaggactgg ctgaacggca aggagtacaa gtgcaaggtc  1020
tccaacaaag gcctcccagc ccccatcgag aaaaccatct ccaaaaccaa agggcagccc  1080
cgagaaccac aggtgtacac cctgccccca tcccgggagg agatgaccaa gaaccaggtc  1140
agcctgacct gcctggtcaa aggcttctac cccagcgaca tcgccgtgga gtgggagagc  1200
aatgggcagc cggagaacaa ctacaagacc acacctccca tgctggactc cgacggctcc  1260
ttcttcctct acagcaagct caccgtggac aagagcaggt ggcagcaggg gaacgtcttc  1320
```

```
tcatgctccg tgatgcatga ggctctgcac aaccactaca cgcagaagag cctctccctg    1380
tctccgggta aatgatag                                                  1398
```

<210> SEQ ID NO 2
<211> LENGTH: 464
<212> TYPE: PRT
<213> ORGANISM: Homo sapiens

<400> SEQUENCE: 2

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Asp Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Pro Gly Tyr Tyr Gly Met Asp Val Trp
        115                 120                 125

Gly Gln Gly Thr Thr Val Thr Val Ser Ser Ala Ser Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365
```

```
Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly Lys
            450                 455                 460

<210> SEQ ID NO 3
<211> LENGTH: 705
<212> TYPE: DNA
<213> ORGANISM: Homo sapiens

<400> SEQUENCE: 3
atgttgccat cacaactcat tgggtttctg ctgctctggg ttccagcttc caggggtgaa    60
attgtgctga ctcagtctcc agactttcag tctgtgactc caaaagagaa agtcaccatc   120
acctgccggg ccagtcagag aattggtagt agcttacact ggtaccagca gaaaccagat   180
cagtctccaa aactcctcat caagtatgct tcccagtcct tctcaggggt cccctcgagg   240
ttcagtggca gtggatctgg gacagatttc accctcacca tcaatagcct ggaagctgaa   300
gatgctgcaa cttattactg tcatcagagt ggtcgtttac cgctcacttt cggcggaggg   360
accaaggtgg agatcaaacg aactgtggct gcaccatctg tcttcatctt cccgccatct   420
gatgagcagt tgaaatctgg aactgcctct gttgtgtgcc tgctgaataa cttctatccc   480
agagaggcca agtacagtg gaaggtggat aacgccctcc aatcgggtaa ctcccaggag   540
agtgtcacag agcaggacag caaggacagc acctacagcc tcagcagcac cctgacgctg   600
agcaaagcag actacgagaa acacaaagtc tacgcctgcg aagtcaccca tcagggcctg   660
agctcgcccg tcacaaagag cttcaacagg ggagagtgtt agtga                   705

<210> SEQ ID NO 4
<211> LENGTH: 233
<212> TYPE: PRT
<213> ORGANISM: Homo sapiens

<400> SEQUENCE: 4

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Arg Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Thr Tyr Tyr Cys His Gln Ser Gly Arg
            100                 105                 110
```

```
Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 5
<211> LENGTH: 1410
<212> TYPE: DNA
<213> ORGANISM: Homo sapiens

<400> SEQUENCE: 5
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120 tgtgcagcct ctggattcac cttcagtagc tatggcatgc actgggtccg ccaggctcca    180
ggcaaggggc tggagtgggt ggcagttata tcaaatgatg gaaataataa atactatgca    240
gactccgtga agggccgatt caccatctcc agagacaatt ccaaaaacac gctgtatctg    300
caaatgaaca gcctgcgcgc tgaggacacg gctgtgtatt actgtgcgag agatagtacg    360 gcgataaccct actactacta cggaatggac gtctggggcc aagggaccac ggtcaccgtc    420
tcctcagctt ccaccaaggg cccatccgtc ttccccctgg cgccctgctc tagaagcacc    480
tccgagagca cagcggccct gggctgcctg gtcaaggact acttccccga accggtgacg    540
gtgtcgtgga actcaggcgc tctgaccagc ggcgtgcaca ccttcccagc tgtcctacag    600
tcctcaggac tctactccct cagcagcgtg gtgaccgtgc cctccagcaa cttcggcacc    660
cagacctaca cctgcaacgt agatcacaag cccagcaaca ccaaggtgga caagacagtt    720
gagcgcaaat gttgtgtcga gtgcccaccg tgcccagcac cacctgtggc aggaccgtca    780
gtcttcctct tccccccaaa acccaaggac accctcatga tctcccggac ccctgaggtc    840
acgtgcgtgg tggtggacgt gagccacgaa gaccccgagg tccagttcaa ctggtacgtg    900
gacggcgtgg aggtgcataa tgccaagaca aagccacggg aggagcagtt caacagcacg    960
ttccgtgtgg tcagcgtcct caccgttgtg caccaggact ggctgaacgg caaggagtac   1020
aagtgcaagg tctccaacaa aggcctccca gcccccatcg agaaaaccat ctccaaaacc   1080
aaagggcagc cccgagaacc acaggtgtac accctgcccc catcccggga ggagatgacc   1140
aagaaccagg tcagcctgac ctgcctggtc aaaggcttct accccagcga catcgccgtg   1200
gagtgggaga gcaatgggca gccggagaac aactacaaga ccacacctcc catgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatgatag                                     1410
```

<210> SEQ ID NO 6
<211> LENGTH: 468
<212> TYPE: PRT
<213> ORGANISM: Homo sapiens

<400> SEQUENCE: 6

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Asn Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Ser Thr Ala Ile Thr Tyr Tyr Tyr Tyr Gly
        115                 120                 125

Met Asp Val Trp Gly Gln Gly Thr Thr Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Phe Arg Val Val Ser Val Leu Thr Val Val His Gln Asp Trp Leu Asn
                325                 330                 335

Gly Lys Glu Tyr Lys Cys Lys Val Ser Asn Lys Gly Leu Pro Ala Pro
            340                 345                 350

Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

```
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Met Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 7
<211> LENGTH: 714
<212> TYPE: DNA
<213> ORGANISM: Homo sapiens

<400> SEQUENCE: 7
atggacatga gggtccccgc tcagctcctg gggctcctgc tactctggct ccgaggtgcc    60
agatgtgaca tccagatgac ccagtctcca tcctccctgt ctgcatctgt cggagacaga   120
gtcaccatca cttgccgggc aagtcagagt attagtagct atttaaattg gtatcagcag   180
aaaccaggga agcccctaa gctcctgatc tatgctgcat ccagtttgag tcaggggtc    240 ccatcacggt tcagtggtag tggatctggg acagatttca ctctcaccat cagttctctg   300
caacctgagg attttgcaac ttactactgt caccagagtt acagtctccc attcactttc   360
ggccctggga ccaaagtgga tatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta gtga          714

<210> SEQ ID NO 8
<211> LENGTH: 236
<212> TYPE: PRT
<213> ORGANISM: Homo sapiens

<400> SEQUENCE: 8

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Ser Gln Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys His Gln
            100                 105                 110
```

```
Ser Tyr Ser Leu Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 9
<211> LENGTH: 714
<212> TYPE: DNA
<213> ORGANISM: Homo sapiens

<400> SEQUENCE: 9

```
atggacatga gggtccccgc tcagctcctg gggctcctgc tactctggct ccgaggtgcc    60
agatgtgaca tccagatgac ccagtctcca tcctccctgt ctgcatctgt cggagacaga   120
gtcaccatca cttgccgggc aagtcagagt attagtagct atttaaattg gtatcagcag   180
aaaccaggga agcccctaa gctcctgatc tatgctgcat ccggtttgaa gcgtggggtc   240
ccatcacggt tcagtggtag tggatctggg acagatttca ctctcaccat cagttctctg   300
caacctgagg attttgcaac ttactactgt cagcagagtt acagtactcc attcactttc   360
ggccctggga ccaaagtgga tatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta gtga          714
```

<210> SEQ ID NO 10
<211> LENGTH: 236
<212> TYPE: PRT
<213> ORGANISM: Homo sapiens

<400> SEQUENCE: 10

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Gly Leu Lys Arg Gly Val
65                  70                  75                  80
```

```
Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ser Tyr Ser Thr Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 11
<211> LENGTH: 714
<212> TYPE: DNA
<213> ORGANISM: Homo sapiens

<400> SEQUENCE: 11
atggacatga gggtccccgc tcagctcctg gggctcctgc tactctggct ccgaggtgcc    60
agatgtgaca tccagatgac ccagtctcca tcctccctgt ctgcatctgt cggagacaga   120
gtcaccatca cttgccgggc aagtcagagt attagtagct atttaaattg gtatcagcag   180
aaaccaggga aagcccctaa gctcctgatc tatgctgcat ccagtttgag tcaggggtc   240 ccatcacggt tcagtggtag tggatctggg acagatttca ctctcaccat cagttctctg   300
caacctgagg attttgcaac ttactactgt cagcagagtt acagtactcc attcactttc   360
ggccctggga ccaaagtgga tatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgtta gtga          714

<210> SEQ ID NO 12
<211> LENGTH: 236
<212> TYPE: PRT
<213> ORGANISM: Homo sapiens

<400> SEQUENCE: 12

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45
```

```
Gln Ser Ile Ser Ser Tyr Leu Asn Trp Tyr Gln Gln Lys Pro Gly Lys
         50                  55                  60

Ala Pro Lys Leu Leu Ile Tyr Ala Ala Ser Ser Leu Ser Gln Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
                100                 105                 110

Ser Tyr Ser Thr Pro Phe Thr Phe Gly Pro Gly Thr Lys Val Asp Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 13
<211> LENGTH: 1413
<212> TYPE: DNA
<213> ORGANISM: Homo sapiens

<400> SEQUENCE: 13
atgaaacacc tgtggttctt cctcctgctg gtggcagctc ccagatgggt cctgtcccag      60
gtgcagctgc aggagtcggg cccaggactg gtgaagcctt cggagaccct gtccctcacc     120
tgcactgtct ctggtgactc catcagtagt aactattgga gctggatccg gcagcccgcc     180
gggaagggac tggagtggat tgggcgtatc tataccagtg ggggcaccaa ctccaacccc     240
tccctcaggg tcgagtcac catgtcagta gacacgtcca agaaccagtt ctctctgaaa     300
ctgagttctg tgaccgccgc ggacacggcc gtgtattact gtgcgagaga tcgtattact     360
ataattcggg gacttattcc atccttcttt gactactggg gccagggaac cctggtcacc     420
gtctcctcag cttccaccaa gggcccatcc gtcttccccc tggcgccctg ctctagaagc     480
acctccgaga gcacagcggc cctgggctgc ctggtcaagg actacttccc cgaaccggtg     540
acggtgtcgt ggaactcagg cgctctgacc agcggcgtgc acaccttccc agctgtccta     600
cagtcctcag gactctactc cctcagcagc gtggtgaccg tgccctccag caacttcggc     660
acccagacct acacctgcaa cgtagatcac aagcccagca caccaaggt ggacaagaca     720 gttgagcgca aatgttgtgt cgagtgccca ccgtgcccag caccacctgt ggcaggaccg     780
tcagtcttcc tcttcccccc aaaacccaag gacaccctca tgatctcccg gacccctgag     840
gtcacgtgcg tggtggtgga cgtgagccac gaagacccg aggtccagtt caactggtac     900
gtggacggcg tggaggtgca taatgccaag acaaagccac gggaggagca gttcaacagc     960
acgttccgtg tggtcagcgt cctcaccgtt gtgcaccagg actggctgaa cggcaaggag    1020
tacaagtgca aggtctccaa caaaggcctc ccagccccca tcgagaaaac catctccaaa    1080
```

```
accaaagggc agccccgaga accacaggtg tacaccctgc ccccatcccg ggaggagatg    1140
accaagaacc aggtcagcct gacctgcctg gtcaaaggct tctacccag cgacatcgcc    1200 gtggagtggg agagcaatgg gcagccggag aacaactaca agaccacacc tcccatgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga tag                                 1413
```

<210> SEQ ID NO 14
<211> LENGTH: 469
<212> TYPE: PRT
<213> ORGANISM: Homo sapiens

<400> SEQUENCE: 14

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Asp Ser Ile
        35                  40                  45

Ser Ser Asn Tyr Trp Ser Trp Ile Arg Gln Pro Ala Gly Lys Gly Leu
    50                  55                  60

Glu Trp Ile Gly Arg Ile Tyr Thr Ser Gly Thr Asn Ser Asn Pro
65                  70                  75                  80

Ser Leu Arg Gly Arg Val Thr Met Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Arg Ile Thr Ile Ile Arg Gly Leu Ile Pro Ser
        115                 120                 125

Phe Phe Asp Tyr Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320
```

```
Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 15
<211> LENGTH: 729
<212> TYPE: DNA
<213> ORGANISM: Homo sapiens

<400> SEQUENCE: 15
atggtgttgc agacccaggt cttcatttct ctgttgctct ggatctctgg tgcctacggg      60
gacatcgtga tgacccagtc tccagactcc ctggctgtgt ctctgggcga gagggccacc     120
atcaactgca gtccagcca gagtgtttta tacagctcca acaataagaa ctacttagct      180
tggtaccaac agaaaccagg acagcctcct aaattgctca tttactgggc atctatacgg     240
gaatatgggg tccctgaccg attcagtggc agcgggtctg ggacagattt cactctcacc     300
atcagcagcc tgcaggctga agatgtggca gtttattatt gtcaacaata ttatagtatt     360
cctcccctca ctttcggcgg agggaccaag gtggagatca aacgaactgt ggctgcacca     420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa agagcttcaa caggggagag     720
tgttagtga                                                             729

<210> SEQ ID NO 16
<211> LENGTH: 241
<212> TYPE: PRT
<213> ORGANISM: Homo sapiens

<400> SEQUENCE: 16

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45
```

-continued

| | | | | | | | | | | | | |
|---|---|---|---|---|---|---|---|---|---|---|---|---|
| Val | Leu | Tyr | Ser | Ser | Asn | Asn | Lys | Asn | Tyr | Leu | Ala | Trp | Tyr | Gln | Gln |
| | 50 | | | | 55 | | | | 60 | | | | | | |
| Lys | Pro | Gly | Gln | Pro | Lys | Leu | Leu | Ile | Tyr | Trp | Ala | Ser | Ile | Arg |
| 65 | | | | 70 | | | | | 75 | | | | | 80 |
| Glu | Tyr | Gly | Val | Pro | Asp | Arg | Phe | Ser | Gly | Ser | Gly | Ser | Gly | Thr | Asp |
| | | | | 85 | | | | | 90 | | | | | 95 | |
| Phe | Thr | Leu | Thr | Ile | Ser | Ser | Leu | Gln | Ala | Glu | Asp | Val | Ala | Val | Tyr |
| | | | 100 | | | | | 105 | | | | | 110 | | |
| Tyr | Cys | Gln | Gln | Tyr | Tyr | Ser | Ile | Pro | Pro | Leu | Thr | Phe | Gly | Gly | Gly |
| | | | 115 | | | | | 120 | | | | | 125 | | |
| Thr | Lys | Val | Glu | Ile | Lys | Arg | Thr | Val | Ala | Ala | Pro | Ser | Val | Phe | Ile |
| | 130 | | | | | 135 | | | | | 140 | | | | |
| Phe | Pro | Pro | Ser | Asp | Glu | Gln | Leu | Lys | Ser | Gly | Thr | Ala | Ser | Val | Val |
| 145 | | | | | 150 | | | | | 155 | | | | | 160 |
| Cys | Leu | Leu | Asn | Asn | Phe | Tyr | Pro | Arg | Glu | Ala | Lys | Val | Gln | Trp | Lys |
| | | | | 165 | | | | | 170 | | | | | 175 | |
| Val | Asp | Asn | Ala | Leu | Gln | Ser | Gly | Asn | Ser | Gln | Glu | Ser | Val | Thr | Glu |
| | | | 180 | | | | | 185 | | | | | 190 | | |
| Gln | Asp | Ser | Lys | Asp | Ser | Thr | Tyr | Ser | Leu | Ser | Ser | Thr | Leu | Thr | Leu |
| | | | 195 | | | | | 200 | | | | | 205 | | |
| Ser | Lys | Ala | Asp | Tyr | Glu | Lys | His | Lys | Val | Tyr | Ala | Cys | Glu | Val | Thr |
| | 210 | | | | | 215 | | | | | 220 | | | | |
| His | Gln | Gly | Leu | Ser | Ser | Pro | Val | Thr | Lys | Ser | Phe | Asn | Arg | Gly | Glu |
| 225 | | | | | 230 | | | | | 235 | | | | | 240 |
| Cys | | | | | | | | | | | | | | | |

<210> SEQ ID NO 17
<211> LENGTH: 726
<212> TYPE: DNA
<213> ORGANISM: Homo sapiens

<400> SEQUENCE: 17

```
atggtgttgc agacccaggt cttcatttct ctgttgctct ggatctctgg tgcctacggg      60
gacatcgtga tgacccagtc tccagactcc ctggctgtgt ctctgggcga gagggccacc     120
atcaactgca agtccagcca gagtgtttta tacagctcca acaataagaa ctacttagct     180
tggtaccaac agaaaccagg acagcctcct aaattgctca tttactgggc atctatacgg     240
gaatatgggg tccctgaccg attcagtggc agcgggtctg ggacagattt cactctcacc     300
atcagcagcc tgcaggctga agatgtggca gtttatttct gtcaacaata ttatagtacc     360
cctctcactt tcggcggagg gaccaaggtg gagatcaaac gaactgtggc tgcaccatct     420
gtcttcatct tcccgccatc tgatgagcag ttgaaatctg gaactgcctc tgttgtgtgc     480
ctgctgaata acttctatcc cagagaggcc aaagtacagt ggaaggtgga taacgccctc     540
caatcgggta actcccagga gagtgtcaca gagcaggaca gcaaggacag cacctacagc     600
ctcagcagca ccctgacgct gagcaaagca gactacgaga aacacaaagt ctacgcctgc     660
gaagtcaccc atcagggcct gagctcgccc gtcacaaaga gcttcaacag gggagagtgt     720
tagtga                                                                726
```

<210> SEQ ID NO 18
<211> LENGTH: 240
<212> TYPE: PRT
<213> ORGANISM: Homo sapiens

<400> SEQUENCE: 18

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Tyr Ser Ser Asn Asn Lys Asn Tyr Leu Ala Trp Tyr Gln Gln
    50                  55                  60

Lys Pro Gly Gln Pro Pro Lys Leu Leu Ile Tyr Trp Ala Ser Ile Arg
65                  70                  75                  80

Glu Tyr Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Phe Cys Gln Gln Tyr Tyr Ser Thr Pro Leu Thr Phe Gly Gly Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 19
<211> LENGTH: 726
<212> TYPE: DNA
<213> ORGANISM: Homo sapiens

<400> SEQUENCE: 19

```
atggtgttgc agacccaggt cttcatttct ctgttgctct ggatctctgg tgcctacggg    60
gacatcgtga tgacccagtc tccagactcc ctggctgtgt ctctgggcga gagggccacc   120
atcaactgca agtccagcca gagtgtttta tacagctcca acaataagaa ctacttagct   180
tggtaccaac agaaaccagg acagcctcct aaattgctca tttactgggc atctatacgg   240
gaatatgggg tccctgaccg attcagtggc agcgggtctg ggacagattt cactctcacc   300
atcagcagcc tgcaggctga agatgtggca gtttattatt gtcaacaata ttatagtacc   360
cctctcactt tcggcggagg gaccaaggtg gagatcaaac gaactgtggc tgcaccatct   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga aacacaaagt ctacgcctgc   660
gaagtcaccc atcagggcct gagctcgccc gtcacaaaga gcttcaacag gggagagtgt   720
tagtga                                                              726
```

<210> SEQ ID NO 20
<211> LENGTH: 240
<212> TYPE: PRT
<213> ORGANISM: Homo sapiens

<400> SEQUENCE: 20

Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Ser Gln Ser
            35                  40                  45

Val Leu Tyr Ser Ser Asn Asn Lys Asn Tyr Leu Ala Trp Tyr Gln Gln
        50                  55                  60

Lys Pro Gly Gln Pro Pro Lys Leu Leu Ile Tyr Trp Ala Ser Ile Arg
65                  70                  75                  80

Glu Tyr Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
                100                 105                 110

Tyr Cys Gln Gln Tyr Tyr Ser Thr Pro Leu Thr Phe Gly Gly Gly Thr
            115                 120                 125

Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
                180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 21
<211> LENGTH: 1416
<212> TYPE: DNA
<213> ORGANISM: Homo sapiens

<400> SEQUENCE: 21
atggaactgg ggctccgctg gttttccctt gttgctattt tagaaggtgt ccagtgtgag      60
gtgcagctgg tggagtctgg gggaggcctg gtcaagcctg gggggtccct gagactctcc     120
tgtgcagcct ctggattcac cttcagtagc tatagcatga actgggtccg ccaggctcca     180
gggaaggggc tggagtgggt ctcatccatt agtagtagta gtagttacat atactacgca     240
gactcagtga agggccgatt caccatctcc agagacaacg ccaagaactc actgtatctg     300
caaatgaaca gcctgagagc cgaggacacg gctgtgtatt actgtgcgag agatgggtat     360
agcagtggct ggtactacta ctactacggt atggacgtct ggggccaagg gaccacggtc     420
accgtctcct cagcttccac caagggccca tccgtcttcc ccctggcgcc ctgctctaga     480
agcacctccg agagcacagc ggccctgggc tgcctggtca aggactactt ccccgaaccg     540
gtgacggtgt cgtggaactc aggcgctctg accagcggcg tgcacacctt cccagctgtc     600

```
ctacagtcct caggactcta ctccctcagc agcgtggtga ccgtgccctc cagcaacttc    660
ggcacccaga cctacacctg caacgtagat cacaagccca gcaacaccaa ggtggacaag    720
acagttgagc gcaaatgttg tgtcgagtgc ccaccgtgcc cagcaccacc tgtggcagga    780
ccgtcagtct tcctcttccc cccaaaaccc aaggacaccc tcatgatctc ccggaccect    840 gaggtcacgt gcgtggtggt ggacgtgagc cacgaagacc ccgaggtcca gttcaactgg    900
tacgtggacg gcgtggaggt gcataatgcc aagacaaagc cacgggagga gcagttcaac    960
agcacgttcc gtgtggtcag cgtcctcacc gttgtgcacc aggactggct gaacggcaag   1020
gagtacaagt gcaaggtctc caacaaaggc ctcccagccc ccatcgagaa aaccatctcc   1080
aaaaccaaag ggcagccccg agaaccacag gtgtacaccc tgcccccatc ccgggaggag   1140
atgaccaaga accaggtcag cctgacctgc ctggtcaaag gcttctaccc cagcgacatc   1200
gccgtggagt gggagagcaa tgggcagccg gagaacaact acaagaccac acctcccatg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tgatag                             1416
```

<210> SEQ ID NO 22
<211> LENGTH: 470
<212> TYPE: PRT
<213> ORGANISM: Homo sapiens

<400> SEQUENCE: 22

```
Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Ser Ile Ser Ser Ser Ser Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Gly Tyr Ser Ser Gly Trp Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240
```

```
Thr Val Glu Arg Lys Cys Cys Val Glu Cys Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 23
<211> LENGTH: 723
<212> TYPE: DNA
<213> ORGANISM: Homo sapiens

<400> SEQUENCE: 23
atgaggctcc ctgctcagct cctggggctg ctaatgctct ggataccagg atccagtgca      60
gatattgtga tgacccagac tccactctct ctgtccgtca ctcctggaca gccggcctcc     120
atctcctgca gtctagtca  gagcctcctg cttagtgatg aaagaccta  tttgaattgg     180 tacctgcaga agcccggcca gcctccacag ctcctgatct atgaagtttc caaccgcttc    240
tctggagtgc cagacaggtt cagtggcagc gggtcaggga cagatttcac actgaaaatc    300
agccgggtgg aggctgagga tgttggggtt tattactgca tgcaaagtat acagcttatg    360
tgcagttttg gccaggggac caagctggag atcaaacgaa ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720
tga                                                                  723
```

```
<210> SEQ ID NO 24
<211> LENGTH: 239
<212> TYPE: PRT
<213> ORGANISM: Homo sapiens

<400> SEQUENCE: 24

Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu Leu Ser Asp Gly Lys Thr Tyr Leu Asn Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Ser
            100                 105                 110

Cys Met Gln Ser Ile Gln Leu Met Ser Ser Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 25
<211> LENGTH: 1410
<212> TYPE: DNA
<213> ORGANISM: Homo sapiens

<400> SEQUENCE: 25
atggactgga cctggagcat ccttttcttg gtggcagcag caacaggtgc ccactcccag      60
gttcagctgg tgcagtctgg agctgaggtg aagaagcctg ggcctcagt gaaggtctcc     120 tgcaaggctt ctggttacac ctttaccagc tatggtatca ctgggtgcg acaggcccct     180 ggacaagggc ttgagtggat gggatggatc agcgtttaca gtggtaacac aaactatgca     240
cagaaggtcc agggcagagt caccatgacc gcagacacat ccacgagcac agcctacatg     300
gacctgagga gcctgagatc tgacgacacg gccgtgtatt actgtgcgag agagggtagc     360
agctcgtccg agactactat ttacggtatg gacgtctggg gccaagggac cacggtcacc     420
gtctcctcag cctccaccaa gggcccatcg gtcttccccc tggcgccctg ctccaggagc     480
acctccgaga gcacagcggc cctgggctgc ctggtcaagg actacttccc cgaaccggtg     540
acggtgtcgt ggaactcagg cgctctgacc agcggcgtgc acaccttccc agctgtccta     600
```

-continued

```
cagtcctcag gactctactc cctcagcagc gtggtgaccg tgccctccag caacttcggc      660
acccagacct acacctgcaa cgtagatcac aagcccagca acaccaaggt ggacaagaca      720
gttgagcgca aatgttgtgt cgagtgccca ccgtgcccag caccacctgt ggcaggaccg      780
tcagtcttcc tcttcccccc aaaacccaag gacaccctca tgatctcccg gacccctgag      840
gtcacgtgcg tggtggtgga cgtgagccac gaagacccga ggtccagtt caactggtac      900 gtggacggcg tggaggtgca taatgccaag acaaagccac gggaggagca gttcaacagc      960
acgttccgtg tggtcagcgt cctcaccgtt gtgcaccagg actggctgaa cggcaaggag     1020
tacaagtgca aggtctccaa caaaggcctc ccagccccca tcgagaaaac catctccaaa     1080
accaaagggc agccccgaga accacaggtg tacaccctgc ccccatcccg ggaggagatg     1140
accaagaacc aggtcagcct gacctgcctg gtcaaaggct tctacccag cgacatcgcc      1200 gtggagtggg agagcaatgg gcagccggag aacaactaca agaccacacc tcccatgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga                                       1410
```

<210> SEQ ID NO 26
<211> LENGTH: 469
<212> TYPE: PRT
<213> ORGANISM: Homo sapiens

<400> SEQUENCE: 26

```
Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Asn Trp Val Arg Gln Ala Pro Gly Gln Gly Leu
    50                  55                  60

Glu Trp Met Gly Trp Ile Ser Val Tyr Ser Gly Asn Thr Asn Tyr Ala
65                  70                  75                  80

Gln Lys Val Gln Gly Arg Val Thr Met Thr Ala Asp Thr Ser Thr Ser
                85                  90                  95

Thr Ala Tyr Met Asp Leu Arg Ser Leu Arg Ser Asp Asp Thr Ala Val
            100                 105                 110

Tyr Tyr Cys Ala Arg Glu Gly Ser Ser Ser Gly Asp Tyr Tyr Tyr
        115                 120                 125

Gly Met Asp Val Trp Gly Gln Gly Thr Thr Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240
```

Val Glu Arg Lys Cys Cys Val Glu Cys Pro Pro Cys Pro Ala Pro Pro
            245                 250                 255

Val Ala Gly Pro Ser Val Phe Leu Phe Pro Pro Lys Pro Lys Asp Thr
        260                 265                 270

Leu Met Ile Ser Arg Thr Pro Glu Val Thr Cys Val Val Val Asp Val
    275                 280                 285

Ser His Glu Asp Pro Glu Val Gln Phe Asn Trp Tyr Val Asp Gly Val
290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 27
<211> LENGTH: 1410
<212> TYPE: DNA
<213> ORGANISM: Homo sapiens

<400> SEQUENCE: 27
atggactgga cctggagcat ccttttcttg gtggcagcag caacaggtgc ccactcccag      60
gttcagctgg tgcagtctgg agctgaggtg aagaagcctg ggcctcagt gaaggtctcc     120 tgcaaggctt ctggttacac ctttaccagc tatggtatca ctgggtgcg acaggcccct     180 ggacaagggc ttgagtggat gggatggatc agcgtttaca gtggtaacac aaactatgca     240
cagaagcttc agggcagagt caccatgacc gcagacacat ccacgagcac agcctacatg     300
gacctgagga gcctgagatc tgacgacacg gccgtgtatt actgtgcgag agagggtagc     360
agctcgtccg gagactacta ttacggtatg gacgtctggg gccaagggac cacggtcacc     420
gtctcctcag cctccaccaa gggcccatcg gtcttccccc tggcgccctg ctccaggagc     480
acctccgaga gcacagcggc cctgggctgc ctggtcaagg actacttccc cgaaccggtg     540
acggtgtcgt ggaactcagg cgctctgacc agcggcgtgc acaccttccc agctgtccta     600
cagtcctcag gactctactc cctcagcagc gtggtgaccg tgccctccag caacttcggc     660
acccagacct acacctgcaa cgtagatcac aagcccagca acaccaaggt ggacaagaca     720
gttgagcgca aatgttgtgt cgagtgccca ccgtgcccag caccacctgt ggcaggaccg     780
tcagtcttcc tcttcccccc aaaacccaag gacaccctca tgatctcccg gacccctgag     840

-continued

```
gtcacgtgcg tggtggtgga cgtgagccac gaagacccccg aggtccagtt caactggtac    900
gtggacggcg tggaggtgca taatgccaag acaaagccac gggaggagca gttcaacagc    960
acgttccgtg tggtcagcgt cctcaccgtt gtgcaccagg actggctgaa cggcaaggag   1020
tacaagtgca aggtctccaa caaaggcctc ccagccccca tcgagaaaac catctccaaa   1080
accaaagggc agccccgaga accacaggtg tacaccctgc ccccatcccg ggaggagatg   1140
accaagaacc aggtcagcct gacctgcctg gtcaaaggct tctacccag cgacatcgcc    1200
gtggagtggg agagcaatgg gcagccggag aacaactaca agaccacacc tcccatgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga                                     1410
```

```
<210> SEQ ID NO 28
<211> LENGTH: 469
<212> TYPE: PRT
<213> ORGANISM: Homo sapiens

<400> SEQUENCE: 28
```

| | | | | | | | | | | | | | | |
|---|---|---|---|---|---|---|---|---|---|---|---|---|---|---|
| Met | Asp | Trp | Thr | Trp | Ser | Ile | Leu | Phe | Leu | Val | Ala | Ala | Thr | Gly |
| 1 | | | | 5 | | | | | 10 | | | | | 15 |
| Ala | His | Ser | Gln | Val | Gln | Leu | Val | Gln | Ser | Gly | Ala | Glu | Val | Lys | Lys |
| | | | 20 | | | | | 25 | | | | | 30 | |
| Pro | Gly | Ala | Ser | Val | Lys | Val | Ser | Cys | Lys | Ala | Ser | Gly | Tyr | Thr | Phe |
| | | 35 | | | | | 40 | | | | | 45 | | |
| Thr | Ser | Tyr | Gly | Ile | Asn | Trp | Val | Arg | Gln | Ala | Pro | Gly | Gln | Gly | Leu |
| | 50 | | | | | 55 | | | | | 60 | | | |
| Glu | Trp | Met | Gly | Trp | Ile | Ser | Val | Tyr | Ser | Gly | Asn | Thr | Asn | Tyr | Ala |
| 65 | | | | | 70 | | | | | 75 | | | | | 80 |
| Gln | Lys | Leu | Gln | Gly | Arg | Val | Thr | Met | Thr | Ala | Asp | Thr | Ser | Thr | Ser |
| | | | | 85 | | | | | 90 | | | | | 95 |
| Thr | Ala | Tyr | Met | Asp | Leu | Arg | Ser | Leu | Arg | Ser | Asp | Asp | Thr | Ala | Val |
| | | | 100 | | | | | 105 | | | | | 110 | |
| Tyr | Tyr | Cys | Ala | Arg | Glu | Gly | Ser | Ser | Ser | Gly | Asp | Tyr | Tyr | Tyr |
| | | 115 | | | | | 120 | | | | | 125 | | |
| Gly | Met | Asp | Val | Trp | Gly | Gln | Gly | Thr | Thr | Val | Thr | Val | Ser | Ser | Ala |
| | 130 | | | | | 135 | | | | | 140 | | | |
| Ser | Thr | Lys | Gly | Pro | Ser | Val | Phe | Pro | Leu | Ala | Pro | Cys | Ser | Arg | Ser |
| 145 | | | | | 150 | | | | | 155 | | | | | 160 |
| Thr | Ser | Glu | Ser | Thr | Ala | Ala | Leu | Gly | Cys | Leu | Val | Lys | Asp | Tyr | Phe |
| | | | | 165 | | | | | 170 | | | | | 175 |
| Pro | Glu | Pro | Val | Thr | Val | Ser | Trp | Asn | Ser | Gly | Ala | Leu | Thr | Ser | Gly |
| | | | 180 | | | | | 185 | | | | | 190 | |
| Val | His | Thr | Phe | Pro | Ala | Val | Leu | Gln | Ser | Ser | Gly | Leu | Tyr | Ser | Leu |
| | | 195 | | | | | 200 | | | | | 205 | | |
| Ser | Ser | Val | Val | Thr | Val | Pro | Ser | Ser | Asn | Phe | Gly | Thr | Gln | Thr | Tyr |
| | 210 | | | | | 215 | | | | | 220 | | | |
| Thr | Cys | Asn | Val | Asp | His | Lys | Pro | Ser | Asn | Thr | Lys | Val | Asp | Lys | Thr |
| 225 | | | | | 230 | | | | | 235 | | | | | 240 |
| Val | Glu | Arg | Lys | Cys | Cys | Val | Glu | Cys | Pro | Pro | Cys | Pro | Ala | Pro | Pro |
| | | | | 245 | | | | | 250 | | | | | 255 |
| Val | Ala | Gly | Pro | Ser | Val | Phe | Leu | Phe | Pro | Pro | Lys | Pro | Lys | Asp | Thr |
| | | | 260 | | | | | 265 | | | | | 270 | |

| | | | | | | | | | | | | |
|---|---|---|---|---|---|---|---|---|---|---|---|---|
|Leu|Met|Ile|Ser|Arg|Thr|Pro|Glu|Val|Thr|Cys|Val|Val|Val|Asp|Val|
| |275| | | |280| | | |285| | | | | | |

Ser His Glu Asp Pro Glu Val Gln Phe Asn Trp Tyr Val Asp Gly Val
    290             295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
                340                 345                 350

Pro Ile Glu Lys Thr Ile Ser Lys Thr Lys Gly Gln Pro Arg Glu Pro
            355                 360                 365

Gln Val Tyr Thr Leu Pro Pro Ser Arg Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
450                 455                 460

Leu Ser Pro Gly Lys
465

<210> SEQ ID NO 29
<211> LENGTH: 723
<212> TYPE: DNA
<213> ORGANISM: Homo sapiens

<400> SEQUENCE: 29

```
atgaggctcc ctgctcagct cctggggctg ctaatgctct ggataccttgg atccagtgca      60
gatattgtga tgacccagac tccactctct ctgtccgtca cccctggaca gccggcctcc     120
atctcctgca agtctagtca gagcctcctg catactgatg gaacgaccta tttgtattgg     180
tacctgcaga agccaggcca gcctccacag ctcctgatct atgaagtttc caaccggttc     240
tctggagtgc cagataggtt cagtggcagc gggtcaggga cagatttcac actgaaaatc     300
agccgggtgg aggctgagga tgttggggtt tattactgca tgcaaaatat acagcttccg     360
tggacgttcg gccaagggac caaggtggaa atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgttag     720
tga                                                                  723
```

<210> SEQ ID NO 30
<211> LENGTH: 239
<212> TYPE: PRT
<213> ORGANISM: Homo sapiens

<400> SEQUENCE: 30

Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu His Thr Asp Gly Thr Thr Tyr Leu Tyr Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Asn Ile Gln Leu Pro Trp Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 31
<211> LENGTH: 723
<212> TYPE: DNA
<213> ORGANISM: Homo sapiens

<400> SEQUENCE: 31
atgaggctcc ctgctcagct cctggggctg ctaatgctct ggataccctgg atccagtgca        60
gatattgtga tgacccagac tccactctct ctgtccgtca cccctggaca gccggcctcc       120
atctcctgca agtctagtca gagcctcctg catactgatg gaacgaccta tttgtattgg       180
tacctgcaga agccaggcca gcctccacag ctcctgatct atgaagtttc caaccggttc       240
tctggagtgc cagataggtt cagtggcagc gggtcaggga cagatttcac actgaaaatc       300
agccgggtgg aggctgagga tgttggggatt tattactgca tgcaaagtat acagcttccg       360
tggacgttcg gccaagggac caaggtggaa atcaaacgaa ctgtggctgc accatctgtc       420
ttcatcttcc cgccatctga tgagcagttg aaatctggaa ctgcctctgt tgtgtgcctg       480
ctgaataact tctatcccag agaggccaaa gtacagtgga aggtggataa cgccctccaa       540
tcgggtaact cccaggagag tgtcacagag caggacagca aggacagcac ctacagcctc       600
agcagcaccc tgacgctgag caaagcagac tacgagaaac acaaagtcta cgcctgcgaa       660
gtcacccatc agggcctgag ctcgcccgtc acaaagagct tcaacagggg agagtgttag       720
tga                                                                     723

```
<210> SEQ ID NO 32
<211> LENGTH: 239
<212> TYPE: PRT
<213> ORGANISM: Homo sapiens

<400> SEQUENCE: 32

Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu His Thr Asp Gly Thr Thr Tyr Leu Tyr Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Ile Tyr Tyr
            100                 105                 110

Cys Met Gln Ser Ile Gln Leu Pro Trp Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 33
<211> LENGTH: 723
<212> TYPE: DNA
<213> ORGANISM: Homo sapiens

<400> SEQUENCE: 33
atgaggctcc ctgctcagct cctggggctg ctaatgctct ggatacctgg atccagtgca      60
gatattgtga tgacccagac tccactctct ctgtccgtca cccctggaca gccggcctcc     120
atctcctgca agtctagtca gagcctcctg catactgatg gaacgaccta tttgtattgg     180
tacctgcaga agccaggcca gcctccacag ctcctgatct atgaagtttc caaccggttc     240
tctggagtgc cagataggtt cagtggcagc gggtcaggga cagatttcac actgaaaatc     300
agccgggtgg aggctgagga tgttggggtt tattactgca tgcaaagtat acagcttccg     360
tggacgttcg gccaagggac caaggtggaa atcaaacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
```

```
agcagcaccc tgacgctgag caaagcagac tacgagaaac acaaagtcta cgcctgcgaa    660
gtcacccatc agggcctgag ctcgcccgtc acaagagct tcaacagggg agagtgttag      720
tga                                                                  723
```

<210> SEQ ID NO 34
<211> LENGTH: 239
<212> TYPE: PRT
<213> ORGANISM: Homo sapiens

<400> SEQUENCE: 34

```
Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu His Thr Asp Gly Thr Thr Tyr Leu Tyr Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ser Ile Gln Leu Pro Trp Thr Phe Gly Gln Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 35
<211> LENGTH: 1374
<212> TYPE: DNA
<213> ORGANISM: Homo sapiens

<400> SEQUENCE: 35

```
atggagtttg ggctgagctg ggttttcctc gttgctcttt taagaggtgt ccagtgtcag    60
gtgcagctgg tggagtctgg gggaggcgtg gtccagcctg gaggtccct gagactctcc    120 tgtgcagcgt ctggattcac cttcagtagc tatggcatgc actgggtccg ccaggctcca    180
ggcaaggggc tggagtgggt ggcagttata tggtatgatg gaagtaatga atactatgca    240
gactccgtga agggccgatt caccatctcc agagacaatt ccaagaacac gctgtatctg    300
caaatgaaca gcctgagagc cgaggacacg gctgtgtatt actgtgcgtt tgactactgg    360
ggccagggaa ccctggtcac cgtctcctca gcttccacca agggcccatc cgtcttcccc    420
```

```
ctggcgccct gctccaggag cacctccgag agcacagccg ccctgggctg cctggtcaag    480
gactacttcc ccgaaccggt gacggtgtcg tggaactcag gcgccctgac cagcggcgtg    540
cacaccttcc cggctgtcct acagtcctca ggactctact ccctcagcag cgtggtgacc    600
gtgccctcca gcagcttggg cacgaagacc tacacctgca acgtagatca caagcccagc    660
aacaccaagg tggacaagag agttgagtcc aaatatggtc ccccatgccc atcatgccca    720
gcacctgagt tcctgggggg accatcagtc ttcctgttcc cccaaaaacc caaggacact    780
ctcatgatct cccggacccc tgaggtcacg tgcgtggtgg tggacgtgag ccaggaagac    840
cccgaggtcc agttcaactg gtacgtggat ggcgtggagg tgcataatgc caagacaaag    900
ccgcgggagg agcagttcaa cagcacgtac cgtgtggtca gcgtcctcac cgtcctgcac    960
caggactggc tgaacggcaa ggagtacaag tgcaaggtct ccaacaaagg cctcccgtcc   1020
tccatcgaga aaaccatctc caaagccaaa gggcagcccc gagagccaca ggtgtacacc   1080
ctgcccccat cccaggagga gatgaccaag aaccaggtca gcctgacctg cctggtcaaa   1140
ggcttctacc ccagcgacat cgccgtggag tgggagagca atgggcagcc ggagaacaac   1200
tacaagacca cgcctcccgt gctggactcc gacggctcct tcttcctcta cagcaggcta   1260
accgtggaca agagcaggtg gcaggagggg aatgtcttct catgctccgt gatgcatgag   1320
gctctgcaca accactacac acagaagagc ctctccctgt ctctgggtaa atga         1374
```

<210> SEQ ID NO 36
<211> LENGTH: 457
<212> TYPE: PRT
<213> ORGANISM: Homo sapiens

<400> SEQUENCE: 36

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Glu Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Phe Asp Tyr Trp Gly Gln Gly Thr Leu Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205
```

-continued

| | | | | | | | | | | | | | | |
|---|---|---|---|---|---|---|---|---|---|---|---|---|---|---|
|Lys|Thr|Tyr|Thr|Cys|Asn|Val|Asp|His|Lys|Pro|Ser|Asn|Thr|Lys|Val|
| |210| | | |215| | | |220| | | | | | |

| | | | | | | | | | | | | | | |
|---|---|---|---|---|---|---|---|---|---|---|---|---|---|---|
|Asp|Lys|Arg|Val|Glu|Ser|Lys|Tyr|Gly|Pro|Pro|Cys|Pro|Ser|Cys|Pro|
|225| | | | |230| | | | |235| | | | |240|

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
        435                 440                 445

Lys Ser Leu Ser Leu Ser Leu Gly Lys
    450                 455

<210> SEQ ID NO 37
<211> LENGTH: 717
<212> TYPE: DNA
<213> ORGANISM: Homo sapiens

<400> SEQUENCE: 37

```
atggacatga gggtccctgc tcagctcctg gggctcctgc tgctctggct ctcagtcgca      60
ggtgccagat gtgacatcca gatgacccag tctccatcct ccctgtctgc atctgtagga    120
gacagagtca ccatcacttg ccaggcgagt caggacatta gcaactattt aaattggtat    180
cagcagaaac cagggaaagc ccctaagctc ctgatctacg atgcatccaa tttggaaaca    240
ggggtcccat caaggttcag tggaagtgga tctgggacag attttacttt caccatcagc    300
agcctgcagc ctgaagatat tgcaacatat tcctgtcaac actctgataa tctcatcacc    360
ttcggccagg ggacacgact ggagattaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaggc agactacgag aaacacaaag tctacgcctg cgaagtcacc    660
catcagggcc tgagctcgcc cgtcacaaag agcttcaaca ggggagagtg ttagtga      717
```

-continued

```
<210> SEQ ID NO 38
<211> LENGTH: 237
<212> TYPE: PRT
<213> ORGANISM: Homo sapiens

<400> SEQUENCE: 38

Met Asp Met Arg Val Pro Ala Gln Leu Leu Gly Leu Leu Leu Leu Trp
1               5                   10                  15

Leu Ser Val Ala Gly Ala Arg Cys Asp Ile Gln Met Thr Gln Ser Pro
            20                  25                  30

Ser Ser Leu Ser Ala Ser Val Gly Asp Arg Val Thr Ile Thr Cys Gln
        35                  40                  45

Ala Ser Gln Asp Ile Ser Asn Tyr Leu Asn Trp Tyr Gln Gln Lys Pro
    50                  55                  60

Gly Lys Ala Pro Lys Leu Leu Ile Tyr Asp Ala Ser Asn Leu Glu Thr
65                  70                  75                  80

Gly Val Pro Ser Arg Phe Ser Gly Ser Gly Ser Gly Thr Asp Phe Thr
                85                  90                  95

Phe Thr Ile Ser Ser Leu Gln Pro Glu Asp Ile Ala Thr Tyr Ser Cys
            100                 105                 110

Gln His Ser Asp Asn Leu Ile Thr Phe Gly Gln Gly Thr Arg Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 39
<211> LENGTH: 30
<212> TYPE: PRT
<213> ORGANISM: Homo sapiens

<400> SEQUENCE: 39

Ser Gly Phe Thr Phe Ser Ser Asp Gly Met His Trp Val Arg Gln Glu
1               5                   10                  15

Trp Val Ala Ile Ile Trp Tyr Asp Gly Ser Asn Lys Tyr Tyr
            20                  25                  30

<210> SEQ ID NO 40
<211> LENGTH: 15
<212> TYPE: PRT
<213> ORGANISM: Homo sapiens

<400> SEQUENCE: 40

Glu Trp Val Ala Ile Ile Trp Tyr Asp Gly Ser Asn Lys Tyr Tyr
1               5                   10                  15
```

```
<210> SEQ ID NO 41
<211> LENGTH: 15
<212> TYPE: PRT
<213> ORGANISM: Homo sapiens

<400> SEQUENCE: 41

Arg Ala Ser Gln Arg Ile Gly Ser Ser Leu His Trp Tyr Gln Gln
1               5                   10                  15

<210> SEQ ID NO 42
<211> LENGTH: 15
<212> TYPE: PRT
<213> ORGANISM: Homo sapiens

<400> SEQUENCE: 42

Ala Val Ile Ser Asn Asp Gly Asn Asn Lys Tyr Tyr Ala Asp Ser
1               5                   10                  15

<210> SEQ ID NO 43
<211> LENGTH: 15
<212> TYPE: PRT
<213> ORGANISM: Homo sapiens

<400> SEQUENCE: 43

Ile Ser Ser Tyr Leu Asn Trp Phe Gln Gln Lys Pro Gly Lys Ala
1               5                   10                  15

<210> SEQ ID NO 44
<211> LENGTH: 15
<212> TYPE: PRT
<213> ORGANISM: Homo sapiens

<400> SEQUENCE: 44

Tyr Leu Asn Trp Phe Gln Gln Lys Pro Gly Lys Ala Pro Lys Leu
1               5                   10                  15

<210> SEQ ID NO 45
<211> LENGTH: 15
<212> TYPE: PRT
<213> ORGANISM: Homo sapiens

<400> SEQUENCE: 45

Ala Pro Lys Leu Leu Ile Tyr Ala Ala Ser Gly Leu Lys Arg Gly
1               5                   10                  15

<210> SEQ ID NO 46
<211> LENGTH: 15
<212> TYPE: PRT
<213> ORGANISM: Homo sapiens

<400> SEQUENCE: 46

Leu Leu Ile Tyr Ala Ala Ser Gly Leu Lys Arg Gly Val Pro Ser
1               5                   10                  15

<210> SEQ ID NO 47
<211> LENGTH: 15
<212> TYPE: PRT
<213> ORGANISM: Homo sapiens

<400> SEQUENCE: 47

Ser Gly Leu Lys Arg Gly Val Pro Ser Arg Phe Ser Gly Ser Gly
1               5                   10                  15
```

```
<210> SEQ ID NO 48
<211> LENGTH: 15
<212> TYPE: PRT
<213> ORGANISM: Homo sapiens

<400> SEQUENCE: 48

Gln Pro Glu Asp Phe Ala Thr Tyr Tyr Cys His Gln Ser Tyr Ser
1               5                   10                  15

<210> SEQ ID NO 49
<211> LENGTH: 15
<212> TYPE: PRT
<213> ORGANISM: Homo sapiens

<400> SEQUENCE: 49

Asp Phe Ala Thr Tyr Tyr Cys His Gln Ser Tyr Ser Leu Pro Phe
1               5                   10                  15

<210> SEQ ID NO 50
<211> LENGTH: 15
<212> TYPE: PRT
<213> ORGANISM: Homo sapiens

<400> SEQUENCE: 50

Cys His Gln Ser Tyr Ser Leu Pro Phe Thr Phe Gly Pro Gly Thr
1               5                   10                  15

<210> SEQ ID NO 51
<211> LENGTH: 15
<212> TYPE: PRT
<213> ORGANISM: Homo sapiens

<400> SEQUENCE: 51

Ser Tyr Ser Leu Pro Phe Thr Phe Gly Pro Gly Thr Lys Val Asp
1               5                   10                  15

<210> SEQ ID NO 52
<211> LENGTH: 15
<212> TYPE: PRT
<213> ORGANISM: Homo sapiens

<400> SEQUENCE: 52

Gly Arg Ile Tyr Thr Ser Gly Gly Thr Asn Ser Asn Pro Ser Leu
1               5                   10                  15

<210> SEQ ID NO 53
<211> LENGTH: 15
<212> TYPE: PRT
<213> ORGANISM: Homo sapiens

<400> SEQUENCE: 53

Arg Asp Arg Ile Thr Ile Ile Arg Gly Leu Ile Pro Ser Phe Phe
1               5                   10                  15

<210> SEQ ID NO 54
<211> LENGTH: 15
<212> TYPE: PRT
<213> ORGANISM: Homo sapiens

<400> SEQUENCE: 54

Ile Thr Ile Ile Arg Gly Leu Ile Pro Ser Phe Phe Asp Tyr Trp
1               5                   10                  15
```

```
<210> SEQ ID NO 55
<211> LENGTH: 15
<212> TYPE: PRT
<213> ORGANISM: Homo sapiens

<400> SEQUENCE: 55

Leu Ile Pro Ser Phe Phe Asp Tyr Trp Gly Gln Gly Thr Leu Val
1               5                   10                  15

<210> SEQ ID NO 56
<211> LENGTH: 15
<212> TYPE: PRT
<213> ORGANISM: Homo sapiens

<400> SEQUENCE: 56

Pro Pro Lys Leu Leu Ile Tyr Trp Ala Ser Ile Arg Glu Tyr Gly
1               5                   10                  15

<210> SEQ ID NO 57
<211> LENGTH: 15
<212> TYPE: PRT
<213> ORGANISM: Homo sapiens

<400> SEQUENCE: 57

Ala Glu Asp Val Ala Val Tyr Phe Cys Gln Gln Tyr Tyr Ser Ile
1               5                   10                  15

<210> SEQ ID NO 58
<211> LENGTH: 15
<212> TYPE: PRT
<213> ORGANISM: Homo sapiens

<400> SEQUENCE: 58

Val Ala Val Tyr Phe Cys Gln Gln Tyr Tyr Ser Ile Pro Pro Leu
1               5                   10                  15

<210> SEQ ID NO 59
<211> LENGTH: 15
<212> TYPE: PRT
<213> ORGANISM: Homo sapiens

<400> SEQUENCE: 59

Tyr Phe Cys Gln Gln Tyr Tyr Ser Ile Pro Pro Leu Thr Phe Gly
1               5                   10                  15

<210> SEQ ID NO 60
<211> LENGTH: 15
<212> TYPE: PRT
<213> ORGANISM: Homo sapiens

<400> SEQUENCE: 60

Tyr Ser Ile Pro Pro Leu Thr Phe Gly Gly Gly Thr Lys Val Glu
1               5                   10                  15

<210> SEQ ID NO 61
<211> LENGTH: 15
<212> TYPE: PRT
<213> ORGANISM: Homo sapiens

<400> SEQUENCE: 61

Ala Val Tyr Tyr Cys Ala Arg Asp Gly Tyr Ser Ser Gln Trp Ser
1               5                   10                  15
```

```
<210> SEQ ID NO 62
<211> LENGTH: 15
<212> TYPE: PRT
<213> ORGANISM: Homo sapiens

<400> SEQUENCE: 62

Arg Asp Gly Tyr Ser Ser Gly Trp Ser Tyr Tyr Tyr Tyr Tyr Gly
1               5                   10                  15

<210> SEQ ID NO 63
<211> LENGTH: 15
<212> TYPE: PRT
<213> ORGANISM: Homo sapiens

<400> SEQUENCE: 63

Tyr Ser Ser Gly Trp Ser Tyr Tyr Tyr Tyr Gly Met Asp Val
1               5                   10                  15

<210> SEQ ID NO 64
<211> LENGTH: 15
<212> TYPE: PRT
<213> ORGANISM: Homo sapiens

<400> SEQUENCE: 64

Gly Trp Ser Tyr Tyr Tyr Tyr Gly Met Asp Val Trp Gly Gln
1               5                   10                  15

<210> SEQ ID NO 65
<211> LENGTH: 15
<212> TYPE: PRT
<213> ORGANISM: Homo sapiens

<400> SEQUENCE: 65

Ile Ser Cys Lys Ser Ser Gln Ser Leu Leu Leu Ser Asp Gly Lys
1               5                   10                  15

<210> SEQ ID NO 66
<211> LENGTH: 15
<212> TYPE: PRT
<213> ORGANISM: Homo sapiens

<400> SEQUENCE: 66

Glu Ala Glu Asp Val Gly Val Tyr Ser Cys Met Gln Ser Ile Gln
1               5                   10                  15

<210> SEQ ID NO 67
<211> LENGTH: 15
<212> TYPE: PRT
<213> ORGANISM: Homo sapiens

<400> SEQUENCE: 67

Val Tyr Ser Cys Met Gln Ser Ile Gln Leu Met Ser Ser Phe Gly
1               5                   10                  15

<210> SEQ ID NO 68
<211> LENGTH: 15
<212> TYPE: PRT
<213> ORGANISM: Homo sapiens

<400> SEQUENCE: 68

Ser Ile Gln Leu Met Ser Ser Phe Gly Gln Gly Thr Lys Leu Glu
1               5                   10                  15
```

```
<210> SEQ ID NO 69
<211> LENGTH: 15
<212> TYPE: PRT
<213> ORGANISM: Homo sapiens

<400> SEQUENCE: 69

Ser Val Tyr Ser Gly Asn Thr Asn Tyr Ala Gln Lys Val Gln Gly
1               5                   10                  15

<210> SEQ ID NO 70
<211> LENGTH: 15
<212> TYPE: PRT
<213> ORGANISM: Homo sapiens

<400> SEQUENCE: 70

Ala Val Tyr Tyr Cys Ala Arg Glu Gly Ser Ser Ser Ser Gly Asp
1               5                   10                  15

<210> SEQ ID NO 71
<211> LENGTH: 15
<212> TYPE: PRT
<213> ORGANISM: Homo sapiens

<400> SEQUENCE: 71

Ser Gly Asp Tyr Tyr Tyr Gly Met Asp Val Trp Gly Gln Gly Thr
1               5                   10                  15

<210> SEQ ID NO 72
<211> LENGTH: 15
<212> TYPE: PRT
<213> ORGANISM: Homo sapiens

<400> SEQUENCE: 72

Val Glu Ala Glu Asp Val Gly Ile Tyr Tyr Cys Met Gln Asn Ile
1               5                   10                  15

<210> SEQ ID NO 73
<211> LENGTH: 15
<212> TYPE: PRT
<213> ORGANISM: Homo sapiens

<400> SEQUENCE: 73

Glu Asp Val Gly Ile Tyr Tyr Cys Met Gln Asn Ile Gln Leu Pro
1               5                   10                  15

<210> SEQ ID NO 74
<211> LENGTH: 15
<212> TYPE: PRT
<213> ORGANISM: Homo sapiens

<400> SEQUENCE: 74

Gly Ile Tyr Tyr Cys Met Gln Asn Ile Gln Leu Pro Trp Thr Phe
1               5                   10                  15

<210> SEQ ID NO 75
<211> LENGTH: 15
<212> TYPE: PRT
<213> ORGANISM: Homo sapiens

<400> SEQUENCE: 75

Val Ala Val Ile Trp Tyr Asp Gly Ser Asn Glu Tyr Tyr Ala Asp
1               5                   10                  15
```

<210> SEQ ID NO 76
<211> LENGTH: 15
<212> TYPE: PRT
<213> ORGANISM: Homo sapiens

<400> SEQUENCE: 76

Ile Trp Tyr Asp Gly Ser Asn Glu Tyr Tyr Ala Asp Ser Val Lys
1               5                   10                  15

<210> SEQ ID NO 77
<211> LENGTH: 15
<212> TYPE: PRT
<213> ORGANISM: Homo sapiens

<400> SEQUENCE: 77

Ala Glu Asp Thr Ala Val Tyr Tyr Cys Ala Arg Gly Ala Tyr His
1               5                   10                  15

<210> SEQ ID NO 78
<211> LENGTH: 15
<212> TYPE: PRT
<213> ORGANISM: Homo sapiens

<400> SEQUENCE: 78

Thr Ala Val Tyr Tyr Cys Ala Arg Gly Ala Tyr His Phe Ala Tyr
1               5                   10                  15

<210> SEQ ID NO 79
<211> LENGTH: 15
<212> TYPE: PRT
<213> ORGANISM: Homo sapiens

<400> SEQUENCE: 79

Ala Arg Gly Ala Tyr His Phe Ala Tyr Trp Gly Gln Gly Thr Leu
1               5                   10                  15

<210> SEQ ID NO 80
<211> LENGTH: 15
<212> TYPE: PRT
<213> ORGANISM: Homo sapiens

<400> SEQUENCE: 80

Ser Leu Gln Pro Glu Asp Ile Ala Thr Tyr Ser Cys Gln His Ser
1               5                   10                  15

<210> SEQ ID NO 81
<211> LENGTH: 15
<212> TYPE: PRT
<213> ORGANISM: Homo sapiens

<400> SEQUENCE: 81

Pro Glu Asp Ile Ala Thr Tyr Ser Cys Gln His Ser Asp Asn Leu
1               5                   10                  15

<210> SEQ ID NO 82
<211> LENGTH: 15
<212> TYPE: PRT
<213> ORGANISM: Homo sapiens

<400> SEQUENCE: 82

Ile Ala Thr Tyr Ser Cys Gln His Ser Asp Asn Leu Thr Phe Gly
1               5                   10                  15

-continued

```
<210> SEQ ID NO 83
<211> LENGTH: 15
<212> TYPE: PRT
<213> ORGANISM: Homo sapiens

<400> SEQUENCE: 83

Tyr Ser Cys Gln His Ser Asp Asn Leu Thr Phe Gly Gln Gly Thr
1               5                   10                  15

<210> SEQ ID NO 84
<211> LENGTH: 32
<212> TYPE: PRT
<213> ORGANISM: Homo sapiens

<400> SEQUENCE: 84

Gly Gly Cys Thr Gly Ala Gly Gly Ala Thr Gly Thr Gly Thr Gly Gly
1               5                   10                  15

Gly Thr Thr Thr Ala Thr Ala Thr Ala Cys Thr Gly Cys Ala Thr Gly Cys
                20                  25                  30

<210> SEQ ID NO 85
<211> LENGTH: 32
<212> TYPE: PRT
<213> ORGANISM: Homo sapiens

<400> SEQUENCE: 85

Gly Cys Ala Thr Gly Cys Ala Gly Thr Ala Thr Ala Thr Ala Ala Cys
1               5                   10                  15

Cys Cys Cys Ala Ala Cys Ala Thr Cys Cys Thr Cys Ala Gly Cys Cys
                20                  25                  30

<210> SEQ ID NO 86
<211> LENGTH: 30
<212> TYPE: PRT
<213> ORGANISM: Homo sapiens

<400> SEQUENCE: 86

Cys Thr Gly Cys Ala Thr Gly Cys Ala Ala Gly Thr Ala Thr Ala
1               5                   10                  15

Cys Ala Gly Cys Thr Thr Cys Cys Gly Thr Gly Gly Ala Cys
                20                  25                  30

<210> SEQ ID NO 87
<211> LENGTH: 30
<212> TYPE: PRT
<213> ORGANISM: Homo sapiens

<400> SEQUENCE: 87

Gly Thr Cys Cys Ala Cys Gly Gly Ala Ala Gly Cys Thr Gly Thr Ala
1               5                   10                  15

Thr Ala Cys Thr Thr Thr Gly Cys Ala Thr Gly Cys Ala Gly
                20                  25                  30

<210> SEQ ID NO 88
<211> LENGTH: 43
<212> TYPE: PRT
<213> ORGANISM: Homo sapiens

<400> SEQUENCE: 88

Gly Gly Ala Thr Gly Thr Thr Gly Gly Gly Thr Thr Thr Ala Thr
1               5                   10                  15
```

```
Thr Ala Cys Thr Gly Cys Ala Thr Gly Cys Ala Ala Gly Thr Ala
            20                  25                  30

Thr Ala Cys Ala Gly Cys Thr Thr Cys Cys Gly
        35                  40

<210> SEQ ID NO 89
<211> LENGTH: 43
<212> TYPE: PRT
<213> ORGANISM: Homo sapiens

<400> SEQUENCE: 89

Cys Gly Gly Ala Ala Gly Cys Thr Gly Thr Ala Thr Ala Cys Thr Thr
1               5                   10                  15

Thr Gly Cys Ala Thr Gly Cys Ala Gly Thr Ala Ala Thr Ala Ala Ala
            20                  25                  30

Cys Cys Cys Cys Ala Ala Cys Ala Thr Cys Cys
        35                  40

<210> SEQ ID NO 90
<211> LENGTH: 30
<212> TYPE: PRT
<213> ORGANISM: Homo sapiens

<400> SEQUENCE: 90

Cys Thr Ala Thr Gly Cys Ala Cys Ala Gly Ala Ala Gly Cys Thr Thr
1               5                   10                  15

Cys Ala Gly Gly Gly Cys Ala Gly Ala Gly Thr Cys Ala Cys
            20                  25                  30

<210> SEQ ID NO 91
<211> LENGTH: 30
<212> TYPE: PRT
<213> ORGANISM: Homo sapiens

<400> SEQUENCE: 91

Gly Thr Gly Ala Cys Thr Cys Thr Gly Cys Cys Cys Thr Gly Ala Ala
1               5                   10                  15

Gly Cys Thr Thr Cys Thr Gly Thr Gly Cys Ala Thr Ala Gly
            20                  25                  30

<210> SEQ ID NO 92
<211> LENGTH: 543
<212> TYPE: PRT
<213> ORGANISM: Homo sapiens

<400> SEQUENCE: 92

Met Asp Phe Gly Leu Ala Leu Leu Leu Ala Gly Leu Leu Gly Leu Leu
1               5                   10                  15

Leu Gly Gln Ser Leu Gln Val Lys Pro Leu Gln Val Glu Pro Pro Glu
            20                  25                  30

Pro Val Val Ala Val Ala Leu Gly Ala Ser Arg Gln Leu Thr Cys Arg
        35                  40                  45

Leu Ala Cys Ala Asp Arg Gly Ala Ser Val Gln Trp Arg Gly Leu Asp
    50                  55                  60

Thr Ser Leu Gly Ala Val Gln Ser Asp Thr Gly Arg Ser Val Leu Thr
65                  70                  75                  80

Val Arg Asn Ala Ser Leu Ser Ala Ala Gly Thr Arg Val Cys Val Gly
                85                  90                  95
```

-continued

```
Ser Cys Gly Gly Arg Thr Phe Gln His Thr Val Gln Leu Leu Val Tyr
            100                 105                 110

Ala Phe Pro Asp Gln Leu Thr Val Ser Pro Ala Ala Leu Val Pro Gly
            115                 120                 125

Asp Pro Glu Val Ala Cys Thr Ala His Lys Val Thr Pro Val Asp Pro
            130                 135                 140

Asn Ala Leu Ser Phe Ser Leu Leu Val Gly Gln Glu Leu Glu Gly
145                 150                 155                 160

Ala Gln Ala Leu Gly Pro Glu Val Gln Glu Glu Glu Glu Pro Gln
                165                 170                 175

Gly Asp Glu Asp Val Leu Phe Arg Val Thr Glu Arg Trp Arg Leu Pro
            180                 185                 190

Pro Leu Gly Thr Pro Val Pro Pro Ala Leu Tyr Cys Gln Ala Thr Met
            195                 200                 205

Arg Leu Pro Gly Leu Glu Leu Ser His Arg Gln Ala Ile Pro Val Leu
            210                 215                 220

His Ser Pro Thr Ser Pro Glu Pro Asp Thr Thr Ser Pro Glu Ser
225                 230                 235                 240

Pro Asp Thr Thr Ser Pro Glu Ser Pro Asp Thr Thr Ser Gln Glu Pro
                245                 250                 255

Pro Asp Thr Thr Ser Gln Glu Pro Pro Asp Thr Thr Ser Gln Glu Pro
            260                 265                 270

Pro Asp Thr Thr Ser Pro Glu Pro Pro Asp Lys Thr Ser Pro Glu Pro
            275                 280                 285

Ala Pro Gln Gln Gly Ser Thr His Thr Pro Arg Ser Pro Gly Ser Thr
            290                 295                 300

Arg Thr Arg Arg Pro Glu Ile Gln Pro Lys Ser Cys Asp Lys Thr His
305                 310                 315                 320

Thr Cys Pro Pro Cys Pro Ala Pro Glu Leu Leu Gly Gly Pro Ser Val
                325                 330                 335

Phe Leu Phe Pro Pro Lys Pro Lys Asp Thr Leu Met Ile Ser Arg Thr
            340                 345                 350

Pro Glu Val Thr Cys Val Val Val Asp Val Ser His Glu Asp Pro Glu
            355                 360                 365

Val Lys Phe Asn Trp Tyr Val Asp Gly Val Glu Val His Asn Ala Lys
            370                 375                 380

Thr Lys Pro Arg Glu Glu Gln Tyr Asn Ser Thr Tyr Arg Val Val Ser
385                 390                 395                 400

Val Leu Thr Val Leu His Gln Asp Trp Leu Asn Gly Lys Glu Tyr Lys
                405                 410                 415

Cys Lys Val Ser Asn Lys Ala Leu Pro Ala Pro Ile Glu Lys Thr Ile
            420                 425                 430

Ser Lys Ala Lys Gly Gln Pro Arg Glu Pro Gln Val Tyr Thr Leu Pro
            435                 440                 445

Pro Ser Arg Asp Glu Leu Thr Lys Asn Gln Val Ser Leu Thr Cys Leu
            450                 455                 460

Val Lys Gly Phe Tyr Pro Ser Asp Ile Ala Val Glu Trp Glu Ser Asn
465                 470                 475                 480

Gly Gln Pro Glu Asn Asn Tyr Lys Ala Thr Pro Pro Val Leu Asp Ser
                485                 490                 495

Asp Gly Ser Phe Phe Leu Tyr Ser Lys Leu Thr Val Asp Lys Ser Arg
            500                 505                 510
```

-continued

```
Trp Gln Gln Gly Asn Val Phe Ser Cys Ser Val Met His Glu Ala Leu
        515                 520                 525

His Asn His Tyr Thr Gln Lys Ser Leu Ser Leu Ser Pro Gly Lys
530                 535                 540
```